US011813089B2

(12) United States Patent
Yi et al.

(10) Patent No.: US 11,813,089 B2
(45) Date of Patent: Nov. 14, 2023

(54) FEEDBACK DEVICE AND METHOD FOR PROVIDING THERMAL FEEDBACK USING THE SAME

(71) Applicant: TEGWAY CO., LTD., Daejeon (KR)

(72) Inventors: Kyoungsoo Yi, Daejeon (KR); Ockkyun Oh, Daejeon (KR)

(73) Assignee: TEGWAY CO., LTD., Daejeon (KR)

( * ) Notice: Subject to any disclaimer, the term of this patent is extended or adjusted under 35 U.S.C. 154(b) by 0 days.

(21) Appl. No.: 17/529,895

(22) Filed: Nov. 18, 2021

(65) Prior Publication Data

US 2022/0071566 A1  Mar. 10, 2022

Related U.S. Application Data

(63) Continuation of application No. 16/919,090, filed on Jul. 1, 2020, now Pat. No. 11,207,032, which is a
(Continued)

(30) Foreign Application Priority Data

Nov. 24, 2016 (KR) .......................... 10-2016-0157732
Nov. 24, 2016 (KR) .......................... 10-2016-0157733
(Continued)

(51) Int. Cl.
*F25B 29/00* (2006.01)
*A61B 5/00* (2006.01)
(Continued)

(52) U.S. Cl.
CPC .............. *A61B 5/7271* (2013.01); *A61B 5/01* (2013.01); *A61B 5/015* (2013.01);
(Continued)

(58) Field of Classification Search
CPC ......... A61B 5/7271; A61B 5/01; A61B 5/015; A61B 18/1477; F25B 21/02;
(Continued)

(56) References Cited

U.S. PATENT DOCUMENTS 5,709,219 A * 1/1998 Chen ...................... A63F 13/285
600/595
5,803,810 A * 9/1998 Norton ................... A63F 13/428
250/221
(Continued)

FOREIGN PATENT DOCUMENTS

EP    2 128 907 A1   12/2009
EP    2 511 793 A2   10/2012
(Continued)

OTHER PUBLICATIONS

International Search Report in application No. PCT/KR2017/010430 dated May 29, 2018.
(Continued)

*Primary Examiner* — Naomi J Small
(74) *Attorney, Agent, or Firm* — Maschoff Brennan

(57) ABSTRACT

A method for providing a thermal feedback, performed by a feedback device. The feedback device outputs the thermal feedback, by transmitting a heat generated by a thermoelectric element, to a user via a contact surface contacting with a body part of the user. The method may include obtaining a feedback start message including a type of the thermal feedback, and when the type of the thermal feedback is a thermal grill feedback, outputting the thermal grill feedback by performing a thermal grill operation in which a heat generating operation and a heat absorbing operation is combined. The outputting of the thermal grill feedback may include applying a forward power to the thermoelectric element to perform the heat generating operation, applying a reverse power of which a current direction is opposite to
(Continued)

the forward power to the thermoelectric element to perform the heat absorbing operation, and repeating the applying the forward power and the applying the reverse power alternatively.

18 Claims, 67 Drawing Sheets

Related U.S. Application Data continuation of application No. 15/633,501, filed on Jun. 26, 2017, now Pat. No. 10,736,576.

(60) Provisional application No. 62/415,437, filed on Oct. 31, 2016.

(30) Foreign Application Priority Data

| Nov. 24, 2016 | (KR) | 10-2016-0157734 |
|---|---|---|
| Nov. 24, 2016 | (KR) | 10-2016-0157735 |
| Nov. 24, 2016 | (KR) | 10-2016-0157736 |
| Nov. 24, 2016 | (KR) | 10-2016-0157737 |

(51) Int. Cl.

| G06F 3/01 | (2006.01) |
|---|---|
| H05B 1/02 | (2006.01) |
| A61B 5/01 | (2006.01) |
| A61B 18/14 | (2006.01) |
| F25B 21/02 | (2006.01) |
| G05D 23/19 | (2006.01) |
| G05D 23/20 | (2006.01) |

(52) U.S. Cl.
CPC .......... *A61B 18/1477* (2013.01); *F25B 21/02* (2013.01); *G05D 23/192* (2013.01); *G05D 23/20* (2013.01); *G06F 3/011* (2013.01); *G06F 3/016* (2013.01); *H05B 1/0227* (2013.01); *F25B 2321/0212* (2013.01); *Y02B 30/70* (2013.01)

(58) Field of Classification Search
CPC .......... F25B 2321/0212; G05D 23/192; G05D 23/20; G06F 3/011; G06F 3/016; H05B 1/0227; Y02B 30/70
USPC ........................................................ 165/259
See application file for complete search history.

(56) References Cited

U.S. PATENT DOCUMENTS

| 5,952,728 | A | 9/1999 | Imanishi et al. | |
|---|---|---|---|---|
| 6,353,623 | B1* | 3/2002 | Munks | H01S 5/0687 |
| | | | | 372/38.07 |
| 6,362,740 | B1 | 3/2002 | Jung | |
| 6,496,200 | B1 | 12/2002 | Snibbe et al. | |
| 8,016,673 | B2 | 9/2011 | Takatsuka | |
| 3,550,905 | A1 | 10/2013 | Mikkailov | |
| 8,902,159 | B1 | 12/2014 | Matthews et al. | |
| 9,672,702 | B2 | 6/2017 | Coish et al. | |
| 10,101,810 | B2 | 10/2018 | Li et al. | |
| 2005/0091989 | A1 | 5/2005 | Eija et al. | |
| 2008/0238937 | A1 | 10/2008 | Muraki | |
| 2009/0131165 | A1 | 5/2009 | Buchner et al. | |
| 2009/0149928 | A1 | 6/2009 | Relin | |
| 2009/0233710 | A1 | 9/2009 | Roberts | |
| 2010/0154856 | A1 | 6/2010 | Hiroyama et al. | |
| 2012/0198616 | A1 | 8/2012 | Makansi et al. | |
| 2012/0258800 | A1* | 10/2012 | Mikhailov | A63F 13/285 |
| | | | | 463/36 |
| 2013/0021234 | A1 | 1/2013 | Umminger et al. | |
| 2014/0022162 | A1 | 1/2014 | Yu et al. | |
| 2014/0165607 | A1 | 6/2014 | Alexander | |
| 2014/0192247 | A1 | 7/2014 | Cheong et al. | |
| 2014/0194726 | A1 | 7/2014 | Mishelevich et al. | |
| 2014/0338713 | A1 | 11/2014 | Nakanuma | |
| 2014/0364212 | A1* | 12/2014 | Osman | A63F 13/212 |
| | | | | 463/31 |
| 2016/0056360 | A1 | 2/2016 | Cho et al. | |
| 2016/0098095 | A1 | 4/2016 | Gonzalez-Banos et al. | |
| 2016/0133151 | A1 | 5/2016 | O'Dowd et al. | |
| 2016/0153508 | A1* | 6/2016 | Battlogg | A61F 2/38 |
| | | | | 188/267.2 |
| 2016/0238040 | A1 | 8/2016 | Gallo et al. | |
| 2016/0246370 | A1 | 8/2016 | Osman | |
| 2016/0312505 | A1* | 10/2016 | Wuerth | H02J 50/10 |
| 2017/0354190 | A1 | 12/2017 | Cauchy | |
| 2017/0365764 | A1 | 12/2017 | Shingai et al. | |
| 2018/0095534 | A1* | 4/2018 | Omote | G02B 27/017 |
| 2018/0098635 | A1 | 4/2018 | Jeon et al. | |
| 2019/0063797 | A1 | 2/2019 | Yi et al. | |
| 2019/0381314 | A1 | 12/2019 | Howard | |
| 2020/0046936 | A1 | 2/2020 | Nofzinger et al. | |
| 2020/0060905 | A1 | 2/2020 | Bogie et al. | |

FOREIGN PATENT DOCUMENTS

| JP | 2003-308009 A | 10/2003 |
|---|---|---|
| JP | 2005-077066 A | 3/2005 |
| JP | 2005-234881 A | 9/2005 |
| JP | 2008-227178 A1 | 9/2008 |
| JP | 2012-217861 A | 11/2012 |
| JP | 2013-175627 A | 9/2013 |
| KR | 10-2007-0066931 A | 6/2007 |
| KR | 10-2010-0051386 A | 5/2010 |
| KR | 10-1056950 B1 | 8/2011 |
| KR | 10-2013-0137417 A | 12/2013 |
| KR | 10-2014-0105045 A | 9/2014 |
| KR | 10-1493792 B1 | 2/2015 |
| KR | 10-1493797 B1 | 2/2015 |
| KR | 10-2015-0035634 A | 4/2015 |
| KR | 10-2016-0033585 A | 3/2016 |
| KR | 10-2016-0036383 A | 4/2016 |
| KR | 10-2016-0117944 A | 10/2016 |
| KR | 10-2016-0124388 A | 10/2016 |
| KR | 10-2017-0089441 A | 8/2017 |
| WO | 2009/007952 A2 | 1/2009 |

OTHER PUBLICATIONS

U.S. Office Action in U.S. Appl. No. 15/633,341 dated Jun. 13, 2019.
U.S. Notice of Allowance in U.S. Appl. No. 15/858,351 dated Jun. 25, 2019.
U.S. Notice of Allowance in U.S. Appl. No. 16/310,432 dated Apr. 21, 2020.
U.S. Office Action issued in corresponding U.S. Appl. No. 15/633,501, dated Jun. 27, 2019.
U.S. Office Action in U.S. Appl. No. 16/221,509 dated Jul. 31, 2020.
EP Search Report in Application No. 17863485.3 dated Oct. 6, 2020.
U.S. Office Action in U.S. Appl. No. 16/221,509 dated Nov. 25, 2020.
International Search Report in Application No. PCT/KR2017/011865 dated Feb. 13, 2018.
Written Opinion in Application No. PCT/KR2017/011865 dated Feb. 13, 2018.
International Search Report in Application No. PCT/KR2017/011866 dated Mar. 7, 2018.
Written Opinion in Application No. PCT/KR2017/011866 dated Mar. 7, 2018.
International Search Report in Application No. PCT/KR2017/011867 dated Mar. 19, 2018.
Written Opinion in Application No. PCT/KR2017/011867 dated Mar. 19, 2018.
U.S. Notice of Allowance in U.S. Appl. No. 15/633,341 dated Oct. 8, 2019.

(56) References Cited

OTHER PUBLICATIONS

U.S. Final Office Action in U.S. Appl. No. 15/633,501 dated Dec. 31, 2019.
U.S. Notice of Allowance in U.S. Appl. No. 16/310,430 dated Jan. 8, 2021.
KR Office Action in Application No. 10-2017-0062594 dated Jan. 27, 2021.
U.S. Notice of Allowance in U.S. Appl. No. 16/736,678 dated Apr. 2, 2021.
U.S. Notice of Allowance in U.S. Appl. No. 15/633,501 dated Apr. 2, 2020.
U.S. Notice of Allowance in U.S. Appl. No. 16/310,430 dated Jun. 26, 2020.
KR Office Action dated Jun. 27, 2023 as received in Application No. 10-2016-0157735.
KR Office Action dated Jun. 27, 2023 as received in Application No. 10-2016-0157736.

* cited by examiner $V1+/V1-=V2+/V2-=V3+/V3-=V4+/V4-=V5+/V5-=-1$
$|\Delta T1+|>|\Delta T1-|, |\Delta T2+|>|\Delta T2-|, |\Delta T3+|>|\Delta T3-|, |\Delta T4+|>|\Delta T4-|, |\Delta T5+|>|\Delta T5-|$

| level | forward power | sat. temp. of hot feedback | reverse power | sat. temp. of cold feedback |
|---|---|---|---|---|
| 1 | V1+ | ΔT1+ | V1+ | ΔT1−=−ΔT1+ |
| 2 | V2+ | ΔT2+=2ΔT1+ | V2+ | ΔT2−=−2ΔT1+ |
| 3 | V3+ | ΔT3+=3ΔT1+ | V3+ | ΔT3−=−3ΔT1+ |
| 4 | V4+ | ΔT4+=4ΔT1+ | V4+ | ΔT4−=−4ΔT1+ |
| 5 | V5+ | ΔT5+=5ΔT1+ | V5+ | ΔT5−=−5ΔT1+ |

| neutral ratio | a voltage applied to the first thermoelectric couple group | a voltage applied to the second thermoelectric couple group |
|---|---|---|
| 2 | V1+, V2+ | V2−, V4− |
| 2.5 | V2+ | V5− |
| 3 | V1+ | V3− |
| 4 | V1+ | V4− |
| 5 | V1+ | V5− |

*Fig. 32*

FEEDBACK DEVICE AND METHOD FOR PROVIDING THERMAL FEEDBACK USING THE SAME

CROSS-REFERENCE TO RELATED APPLICATION

This application claims the benefit of U.S. Provisional Application No. 62/415,437, filed on Oct. 21, 2016, the disclosure of which is incorporated by reference in is entirety.

This application also claims foreign priority benefits of the filing date of Korean Application Serial No. 10-2016-0157732, 10-2016-0157733, 10-2016-0157734, 10-2016-0157735, 10-2016-0157736 and 10-2016-0157737, filed on Nov. 24, 2016, and which are incorporated hereby by reference in their entirety.

TECHNICAL FIELD

The present disclosure relates generally to a feedback device and a method for providing a thermal feedback using the feedback device. In particular, the present disclosure relates to a feedback device and a method for providing a thermal grill feedback, in addition to a hot feedback and a cold feedback, as the thermal feedback, and to a feedback device and a method for preventing a thermal inversion illusion which occurs at the termination of the thermal feedback.

BACKGROUND

At the Consumer Electronics Show (CES) in 2016, virtual reality was introduced as one of the most promising future technologies. The development of technologies such as virtual reality (VR) or augmented reality (AR) have increased the demand for devices and methods that enhance user experience (UX). For example, there is interest in methods that enhance user's immersion in the contents by stimulating multiple human senses. VR and AR are normally confined mainly to visual and auditory senses. However, efforts are under way to include various human senses such as olfactory and tactile sense.

Thermoelectric elements (TEs) are electrical devices that generate or absorb heat using the Peltier effect. TEs may be used to provide a thermal feedback to a user. However, the incorporation of the thermoelectric elements in VR or AR applications has been limited because it is difficult to fabricate conventional thermoelectric elements using flat substrates. Thus, it is challenging to have TEs that make tight contact with a body part of a user.

In recent years, however, the Assignee of the present Application has successfully developed flexible thermoelectric elements (FTEs), e.g., as disclosed in Korean Application Serial No. 10-2015-0154087 filed on Nov. 3, 2015. It is expected that the thermal feedback can be effectively delivered to users by overcoming the problems of the conventional thermoelectric elements.

SUMMARY

The following sets forth a simplified summary of selected aspects, embodiments, and examples of the present disclosure for providing a basic understanding of the disclosure. However, the summary does not constitute an extensive overview of all the aspects, embodiments, and examples of the disclosure. Neither is the summary intended to identify critical aspects or delineate the scope of the disclosure. The sole purpose of the summary is to present selected aspects, embodiments, and examples of the disclosure in a concise form as an introduction to the more detailed description of the aspects, embodiments, and examples of the disclosure that follow the summary.

One aspect of the present disclosure is directed to a method for providing a thermal feedback, performed by a feedback device. The method may include applying an operating power to a thermoelectric element to start a thermoelectric operation for outputting the thermal feedback; stopping the application of the operating power to terminate the thermoelectric operation; and when the application of the operating power is stopped, applying a buffering power to the thermoelectric element to reduce a temperature returning speed of a contact surface. The feedback device may include a heat outputting module which is provided as the thermoelectric element and performs the thermoelectric operation including at least one of a heat generating operation and a heat absorbing operation and the contact surface which is configured to contact with a body of the user and transmit a heat generated by the thermoelectric operation.

Another aspect of the present disclosure is directed to a feedback device for providing a thermal feedback. The device may include a heat outputting module, which includes a thermoelectric element performing a thermoelectric operation including at least one of a heat generating operation and a heat absorbing operation; a power terminal supplying an operating power for the thermoelectric operation to the thermoelectric element; and a contact surface which is provided on one side of the thermoelectric element and is configured to contact with a body part of a user. The heat outputting module outputs the thermal feedback by transmitting, via the contact surface, a heat generated due to the thermoelectric operation to the user; and a feedback controller is configured to: apply the operating power to the power terminal to start the thermoelectric operation for outputting the thermal feedback; stop the application of the operating power to terminate the thermoelectric operation; and when the application of the operating power is stopped, apply a buffering power to the power terminal to reduce a temperature returning speed of the contact surface.

Yet another aspect of the present disclosure is directed to a method for providing a thermal feedback, performed by a feedback device. The method includes applying an operating power to an operating group to start a thermoelectric operation for outputting the thermal feedback, the operating group corresponding to at least one of a plurality of thermoelectric couple groups; stopping the application of the operating power for the operating group to terminate the thermoelectric operation to end the thermal feedback; and performing, prior to the stopping, a buffering operation to reduce a temperature returning speed of a contact surface so that a thermal inversion illusion is prevented. The buffering operation may include stopping the application of the operating power for a first portion of the operating group and maintaining the application of the operating power for a second portion of the operating group, the first portion being different from the second portion of the operating group; and the feedback device includes: a thermoelectric couple array that may include the plurality of thermoelectric couple groups and performs the thermoelectric operation including at least one of a heat generating operation and a heat absorbing operation; and the contact surface which is configured to contact with a body of the user and transmit a heat generated by the thermoelectric operation.

Another aspect of the present disclosure is directed to a feedback device for providing a thermal feedback. The device includes a heat outputting module, which includes a thermoelectric element which is provided as a thermoelectric couple array having a plurality of thermoelectric couple groups and performing a thermoelectric operation including at least one of a heat generating operation and a heat absorbing operation; and a power terminal supplying an operating power for the thermoelectric operation to the thermoelectric element, and a contact surface which is provided on one side of the thermoelectric element and is configured to contact with a body part of a user. The heat outputting module outputs the thermal feedback by transmitting, via the contact surface, a heat generated due to the thermoelectric operation to the user; and a feedback controller configured to: apply the operating power to an operating group corresponding to at least a part of the plurality of the thermoelectric couple groups to start the thermoelectric operation for outputting the thermal feedback; stop the application of the operating power for all the operating group to terminate the thermoelectric operation to end the thermal feedback; and perform a buffering operation to reduce a temperature returning speed of the contact surface, wherein the feedback controller performs the buffering operation, prior to stopping of the application of the operating power for all the operating group, by stopping the application of the operating power for a part of the operating group and maintaining the application of the operating power for a remainder of the operating group.

Yet another aspect of the present invention is directed to a gaming controller including a casing having a grip portion gripped by a user and forming an exterior of the gaming controller; an input module receiving a user input according to a manipulation of the user; a communication module communicating with the content reproduction device; a heat outputting module, which includes a thermoelectric element performing a thermoelectric operation, a power terminal applying a power to the thermoelectric element; and a contact surface which is disposed on the grip portion and configured to contact with the user. The heat outputting module outputs the thermal feedback by transmitting, via the contact surface, a heat generated by the thermoelectric operation to the user; and a controller configured to: obtain, via the input module, the user input; send, via the communication module, the user input to the content reproduction device; receive, via the communication module, a feedback information from the content reproduction device; select, from a group of predetermined voltage values, an operating voltage value based on an intensity of the feedback included in the feedback information; generate an operating power having the operating voltage value; apply the operating power to the heat outputting module so that the heat outputting module outputs the thermal feedback; stop the application of the operating power so that the heat outputting module stops outputting the thermal feedback; select, from the group of predetermined voltage values, a buffering voltage value, the buffering voltage value being lower than the operating voltage value; generate a buffering power having the buffering voltage value, and apply the buffering power to the heat outputting module to reduce a temperature returning speed of the contact surface.

One aspect of the present disclosure is directed to a feedback device that provides a thermal feedback to a user and a method of providing the thermal feedback using the feedback device.

Another aspect of the present disclosure is directed to a feedback device that provides a thermal feedback including, in addition to a hot sensation and a cold sensation, a pain sensation using the hot sensation and the cold sensation, and a method of providing the thermal feedback using the feedback device.

Yet another aspect of the present disclosure is directed to a feedback device capable of outputting a multi-level thermal feedback by adjusting the intensity of heat generating operation and a heat absorbing operation, and a method of providing the thermal feedback using the feedback device.

Another aspect of the present disclosure is directed to a feedback device for outputting a thermal grill feedback by using an operating power control, an operating area control, an operating time control, and the like, and a method of providing the thermal feedback using the feedback device.

Another aspect of the present disclosure is directed to a feedback device that prevents damage on the user's skin due to a thermal feedback and a method of providing the thermal feedback using the feedback device.

Another aspect of the present disclosure is directed to a feedback device that prevents a thermal inversion illusion and a method of providing a thermal feedback using the same.

Another aspect of the present disclosure is directed to a feedback device that prevents a thermal inversion illusion using a proper buffering operation according to a type of a thermal feedback including a hot feedback and a cold feedback, and a method for providing the thermal feedback using the feedback device.

One aspect of the present disclosure is directed to a method for providing a thermal feedback, performed by a feedback device, wherein the feedback device includes a heat outputting module which is provided as a thermoelectric element and performs a thermoelectric operation including at least one of a heat generating operation and a heat absorbing operation and a contact surface which is configured to contact with a body of a user and transmit a heat generated by the thermoelectric operation, the method comprising: applying an operating power to the thermoelectric element to start the thermoelectric operation for outputting the thermal feedback; stopping the application of the operating power to terminate the thermoelectric operation; and when the application of the operating power is stopped, applying a buffering power to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a feedback device for providing a thermal feedback, the device may include: a heat outputting module including a thermoelectric element performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: apply the operating power to the power terminal to start the thermoelectric operation for outputting the thermal feedback, stop the application of the operating power to terminate the thermoelectric operation, and when the application of the operating power is stopped, apply a buffering power to the power terminal to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a method for providing a thermal feedback, performed by a feedback device, wherein the feedback device includes a thermoelectric couple array that includes a plurality of thermoelectric couple groups and performs a thermoelectric operation including at least one of a heat generating operation and a heat absorbing operation and a contact surface which is configured to contact with a body of a user and transmit a heat generated by the thermoelectric operation, the method may include: applying an operating power to an operating group corresponding to at least a part of the plurality of the thermoelectric couple groups to start the thermoelectric operation for outputting the thermal feedback; stopping the application of the operating power for all the operating group to terminate the thermoelectric operation so that the thermal feedback ends; and performing, prior to the stopping, a buffering operation to reduce a temperature returning speed of the contact surface so that a thermal inversion illusion is prevented, wherein the buffering operation includes stopping the application of the operating power for a part of the operating group and maintaining the application of the operating power for a remainder of the operating group, and wherein the thermal inversion illusion is defined as an illusionary sensation felt by the user as a sensation opposite to the outputted thermal feedback during returning a temperature of the contact surface to an initial temperature due to the termination of the thermoelectric operation.

Yet another aspect of the present disclosure is directed to a feedback device for providing a thermal feedback, the device may include: a heat outputting module including a thermoelectric element which is provided as a thermoelectric couple array having a plurality of thermoelectric couple groups and performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: apply an operating power to an operating group corresponding to at least a part of the plurality of the thermoelectric couple groups to start the thermoelectric operation for outputting the thermal feedback, stop the application of the operating power for all the operating group to terminate the thermoelectric operation so that the thermal feedback ends, and perform a buffering operation to reduce a temperature returning speed of the contact surface so that a thermal inversion illusion is prevented, wherein the feedback controller performs the buffering operation, prior to stopping of the application of the operating power for all the operating group, by stopping the application of the operating power for a part of the operating group and maintaining the application of the operating power for a remainder of the operating group, and wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a gaming controller, wherein the gaming controller is used as an input interface, of a content reproduction device reproducing a multimedia content, receiving a user input related to the multimedia content, and as an output interface, of the content reproduction device, providing a thermal experience related to the multimedia content by outputting a thermal feedback, the gaming controller may include: a casing having a grip portion gripped by a user and forming an exterior of the gaming controller; an input module receiving the user input according to a manipulation of the user; a communication module communicating with the content reproduction device; a heat outputting module including a thermoelectric element performing a thermoelectric operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: obtain, via the input module, the user input, send, via the communication module, the user input to the content reproduction device, receive, via the communication module, a feedback information from the content reproduction device, select one from predetermined voltage values as an operating voltage value based on an intensity of the feedback included in the feedback information, generate an operating power having the operating voltage value, apply the operating power to the heat outputting module so that the heat outputting module outputs the thermal feedback, stop the application of the operating power so that the heat outputting module stops outputting the thermal feedback, select one less than the operating voltage value from the predetermined voltage values as a buffering voltage, generate a buffering power having the buffering voltage value, and apply the buffering power to the heat outputting module to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a method for providing a thermal feedback, performed by a feedback device, wherein the feedback device includes a heat outputting module which is provided as a thermoelectric element and performs a thermoelectric operation including at least one of a heat generating operation and a heat absorbing operation and a contact surface which is configured to contact with a body of a user and transmit a heat generated by the thermoelectric operation, the method may include: obtaining an information on a type of the thermal feedback including a hot feedback and a cold feedback; applying an operating power according to the type of the thermal feedback to the thermoelectric element to start outputting of the thermal feedback; stopping the application of the operating power to terminate the outputting of the thermal feedback; generating a buffering power based on the type of the thermal feedback; and when the application of the operating power is stopped, applying the buffering power to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a method for providing a thermal feedback, performed by a feedback device, wherein the feedback device includes a heat outputting module which is provided as a thermoelectric element and performs a thermoelectric operation including at least one of a heat generating operation and a heat absorbing operation and a contact surface which is configured to contact with a body of a user and transmit a heat generated by the thermoelectric operation, the method may include: obtaining an information on a type of the thermal feedback including a hot feedback and a cold feedback; applying an operating power according to the type of the thermal feedback to the thermoelectric element to start outputting of the thermal feedback; stopping the application of the operating power to terminate the outputting of the thermal feedback; obtaining a buffering duration which is set differently based on the type of the thermal feedback; and when the application of the operating power is stopped, applying a buffering power for the buffering duration to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a method for providing a thermal feedback, performed by a feedback device, wherein the feedback device includes a thermoelectric couple array that includes a plurality of thermoelectric couple groups and performs a thermoelectric operation including a heat generating operation and a heat absorbing operation and a contact surface which is configured to contact with a body of a user and transmit a heat generated by the thermoelectric operation, the method may include: obtaining an information on a type of the thermal feedback including a hot feedback and a cold feedback; applying an operating power according to the type of the thermal feedback to an operating group to start outputting of the thermal feedback, the operating group including at least part of the plurality of the thermoelectric couple groups; stopping the application of the operating power to terminate the outputting of the thermal feedback; determining a buffering group based on the type of the thermoelectric operation, the buffering group including at least part of the plurality of the thermoelectric couple groups, wherein the number of the thermoelectric couple groups included in the buffering group is smaller than the number of the thermoelectric couple groups included in the operating group; and when the application of the operating power is stopped, applying a buffering power to the buffering group to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a method for providing a thermal feedback, performed by a feedback device, wherein the feedback device includes a thermoelectric couple array that includes a plurality of thermoelectric couple groups and performs a thermoelectric operation including a heat generating operation and a heat absorbing operation and a contact surface which is configured to contact with a body of a user and transmit a heat generated by the thermoelectric operation, the method may include: obtaining an information on a type of the thermal feedback including a hot feedback and a cold feedback; applying an operating power according to the type of the thermal feedback to an operating group to start outputting of the thermal feedback, the operating group including at least part of the plurality of the thermoelectric couple groups; stopping the application of the operating power to terminate the outputting of the thermal feedback; and performing a buffering operation to reduce a temperature returning speed of the contact surface upon the stopping of the application of the operating power so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation, and wherein the buffering operation is performed, before the application of the operating power related to all of the operating group is stopped, by maintaining the application of the operating power to a part of the operating group and stopping the application of the operating power to the rest of the operating group.

Another aspect of the present disclosure is directed to a feedback device for providing a thermal feedback, the device may include: a heat outputting module including a thermoelectric element performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: obtain an information on a type of the thermal feedback including a hot feedback and a cold feedback, apply an operating power according to the type of the thermal feedback to the thermoelectric element to start outputting of the thermal feedback, stop the application of the operating power to terminate the outputting of the thermal feedback, generate a buffering power based on the type of the thermal feedback, and when the application of the operating power is stopped, apply the buffering power to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a feedback device for providing a thermal feedback, the device may include: a heat outputting module including a thermoelectric element performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: obtain an information on a type of the thermal feedback including a hot feedback and a cold feedback, apply an operating power according to the type of the thermal feedback to the thermoelectric element to start outputting of the thermal feedback, stop the application of the operating power to terminate the outputting of the thermal feedback, obtain a buffering duration which is set differently based on the type of the thermal feedback, and when the application of the operating power is stopped, apply a buffering power for the buffering duration to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to a feedback device for providing a thermal feedback, the device may include: a heat outputting module including a thermoelectric couple array that includes a plurality of the thermoelectric couple groups and performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: obtain an information on a type of the thermal feedback including a hot feedback and a cold feedback, apply an operating power according to the type of the thermal feedback to an operating group to start outputting of the thermal feedback, the operating group including at least part of the plurality of the thermoelectric couple groups, stop the application of the operating power to terminate the outputting of the thermal feedback, determine a buffering group based on the type of the thermoelectric operation, the buffering group including at least part of the plurality of the thermoelectric couple groups, wherein the number of the thermoelectric couple groups included in the buffering group is smaller than the number of the thermoelectric couple groups included in the operating group, and when the application of the operating power is stopped, apply a buffering power to the buffering group to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to feedback device for providing a thermal feedback, the device may include: a heat outputting module including a thermoelectric couple array that includes a plurality of the thermoelectric couple groups and performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: obtain an information on a type of the thermal feedback including a hot feedback and a cold feedback, apply an operating power according to the type of the thermal feedback to an operating group to start outputting of the thermal feedback, the operating group including at least part of the plurality of the thermoelectric couple groups, stop the application of the operating power to terminate the outputting of the thermal feedback; and perform a buffering operation to reduce a temperature returning speed of the contact surface upon the stopping of the application of the operating power so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation, and wherein the buffering operation is performed, before the application of the operating power related to all of the operating group is stopped, by maintaining the application of the operating power to a part of the operating group and stopping the application of the operating power to the rest of the operating group.

Another aspect of the present disclosure is directed to method for providing a thermal feedback including a hot feedback, a cold feedback and a thermal grill feedback, performed by a feedback device, wherein the feedback device includes a thermoelectric couple array that includes a plurality of thermoelectric couple groups and performs a thermoelectric operation including a heat generating operation, a heat absorbing operation and a thermal grill operation in which the heat generating operation and the heat absorbing operation is combined and a contact surface which is configured to contact with a body of a user and transmit a heat generated by the thermoelectric operation, the method may include: applying a forward power to a first group of the plurality of the thermoelectric couple groups to perform the heat generating operation and a reverse power to a second group of the plurality of the thermoelectric couple groups to perform the heat absorbing operation so that the thermoelectric couple array performs the thermal grill operation and starts outputting of the thermal grill feedback; and stopping the application of the forward power and the application of the reverse power, wherein the application of the forward power and the application of the reverse power are stopped at different time points.

Another aspect of the present disclosure is directed to feedback device for providing a thermal feedback, the device may include: a heat outputting module including a thermoelectric element provided as a thermoelectric couple array that includes a first thermoelectric couple group performing a heat generating operation and a second thermoelectric couple group performing a heat absorbing operation, a power terminal supplying a power to the thermoelectric element, and a contact surface which is provided on one side of the thermoelectric element and is configured to contact with a body part of a user, wherein the heat outputting module outputs the thermal grill feedback by transmitting, via the contact surface, a hot heat according to the heat generating operation and a cold heat according to the heat absorbing operation to the user; and a feedback controller configured to: apply a forward power to a first thermoelectric couple group and a reverse power to a second thermoelectric couple group so that the thermoelectric element performs the thermal grill operation and starts outputting of the thermal grill feedback, and stop the application of the forward power and the application of the reverse power, wherein the application of the forward power and the application of the reverse power are stopped at different time points.

Another aspect of the present disclosure is directed to method for providing a thermal feedback including a hot feedback, a cold feedback and a thermal grill feedback, performed by a feedback device, wherein the feedback device includes a thermoelectric couple array that includes a plurality of thermoelectric couple groups and performs a thermoelectric operation including a heat generating operation, a heat absorbing operation and a thermal grill operation in which the heat generating operation and the heat absorbing operation is combined and a contact surface which is configured to contact with a body of a user and transmit a heat generated by the thermoelectric operation, the method may include: applying a forward power to a first group of the plurality of the thermoelectric couple groups to perform the heat generating operation and a reverse power to a second group of the plurality of the thermoelectric couple groups to perform the heat absorbing operation so that the thermoelectric couple array performs the thermal grill operation and starts outputting of the thermal grill feedback; stopping the application of the forward power and the application of the reverse power in order to terminate outputting of the thermal grill feedback; and applying a compensation power to at least one of the first group and the second group so that the contact surface returns to an initial temperature.

Another aspect of the present disclosure is directed to feedback device for providing a thermal feedback, the device may include: a heat outputting module including a thermoelectric element provided as a thermoelectric couple array that includes a first thermoelectric couple group performing a heat generating operation and a second thermoelectric couple group performing a heat absorbing operation, a power terminal supplying a power to the thermoelectric element, and a contact surface which is provided on one side of the thermoelectric element and is configured to contact with a body part of a user, wherein the heat outputting module outputs the thermal grill feedback by transmitting, via the contact surface, a hot heat according to the heat generating operation and a cold heat according to the heat absorbing operation to the user; and a feedback controller configured to: apply a forward power to the first thermoelectric couple group to perform the heat generating operation and a reverse power to a second thermoelectric couple group to perform the heat absorbing operation so that the thermoelectric couple array performs the thermal grill operation and starts outputting of the thermal grill feedback, stop the application of the forward power and the reverse power in order to terminate outputting of the thermal grill feedback, and apply a compensation power to at least one of the first thermoelectric couple group and the second thermoelectric couple group so that the contact surface returns to an initial temperature.

Another aspect of the present disclosure is directed to method for providing a thermal feedback, performed by a feedback device, wherein the feedback device includes a heat outputting module which is provided as a thermoelectric element and performs a thermoelectric operation including at least one of a heat generating operation and a heat absorbing operation and a contact surface which is configured to contact with a body of a user and transmit a heat generated by the thermoelectric operation, the method comprising: obtaining a start message requesting outputting the thermal feedback; applying, upon the obtaining the start message, an operating power to the thermoelectric element to start outputting the thermal feedback which corresponds to the start message; stopping the application of the operating power to terminate the thermoelectric operation; when the application of the operating power is stopped, performing a buffering operation reducing a temperature returning speed of the contact surface for preventing a thermal inversion illusion due to the termination of the thermoelectric operation, wherein the thermal inversion illusion is defined as an illusionary sensation felt by the user as a sensation opposite to the outputted thermal feedback during returning a temperature of the contact surface to an initial temperature due to the termination of the thermoelectric operation; and when a new start message is obtained during performing the buffering operation, stopping the buffering operation and applying the operating power to the thermoelectric element to start outputting the thermal feedback which corresponds to the new start message.

Another aspect of the present disclosure is directed to feedback device for providing a thermal feedback, the device may include: a communication module communicating with a content reproduction device executing a multimedia content including a game and an experience application; a heat outputting module including a thermoelectric element performing a thermoelectric operation including at least one of a heat generating operation and a heat absorbing operation, a power terminal supplying a power to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user so that a thermal experience related to the multimedia is provided to the user; and a feedback controller configured to: receive, via the communication module, a start message requesting outputting the thermal feedback, apply, upon the receipt of the start message, an operating power to the thermoelectric element to start outputting the thermal feedback which corresponds to the start message, stop the application of the operating power to terminate the thermoelectric operation, when the application of the operating power is stopped, perform a buffering operation reducing a temperature returning speed of the contact surface for preventing a thermal inversion illusion due to the termination of the thermoelectric operation, wherein the thermal inversion illusion is defined as an illusionary sensation felt by the user as a sensation opposite to the outputted thermal feedback during returning a temperature of the contact surface to an initial temperature due to the termination of the thermoelectric operation, and when a new start message is received during performing the buffering operation, stop the buffering operation and apply the operating power to the thermoelectric element to start outputting the thermal feedback which corresponds to the new start message.

Another aspect of the present disclosure is directed to method for providing a thermal feedback, performed by a feedback device, wherein the feedback device outputs the thermal feedback by transmitting a heat generated by a thermoelectric element, to a user via a contact surface contacting with a body part of the user, the method may include: obtaining a feedback start message including a type of the thermal feedback; and when the type of the thermal feedback is a thermal grill feedback, outputting the thermal grill feedback by performing a thermal grill operation in which a heat generating operation and a heat absorbing operation is combined, wherein the outputting includes applying a forward power to the thermoelectric element to perform the heat generating operation, applying a reverse power of which a current direction is opposite to the forward power to the thermoelectric element to perform the heat absorbing operation, and the application of the forward power and the application of the reverse power is repeated alternatively.

Another aspect of the present disclosure is directed to feedback device for providing a thermal feedback, the device may include: a communication module communicating with an external device; a heat outputting module including a thermoelectric element performing a heat generating operation and a heat absorbing operation, a power terminal supplying a power to the thermoelectric element and a contact surface which is provided on one side of the thermoelectric element and is configured to contact with a body part of a user, wherein the heat outputting module outputs the thermal feedback by transmitting, via the contact surface, a heat generated due to the heat generating operation or the heat absorbing operation; and a feedback controller configured to: receive, via the communication module, a feedback start message including a type of the thermal feedback, when the type of the thermal feedback is a thermal grill feedback, and output the thermal grill feedback by performing a thermal grill operation in which the heat generating operation and the heat absorbing operation is combined, wherein the feedback controller applies a forward power to the thermoelectric element to perform the heat generating operation and a reverse power of which a current direction is opposite to the forward power to the thermoelectric element to perform the heat absorbing operation and repeats the application of the forward power and the application of the reverse power alternatively so that the heat outputting module outputs the thermal grill feedback.

Another aspect of the present disclosure is directed to method for providing a thermal feedback, performed by a feedback device, wherein the feedback device includes a heat outputting module which is provided as a thermoelectric couple array including a plurality of thermoelectric couple groups and performs a thermoelectric operation, and a contact surface which is configured to contact with a body of a user and transmit a heat generated by the thermoelectric couple array, the method may include: applying a forward power for a heat generating operation and a reverse power for a heat absorbing operation, alternatively to a first group of the plurality of the thermoelectric couple groups; applying the forward power and the reverse power alternatively to a second group of the plurality of the thermoelectric couple groups, wherein the application of the forward power to the second group is performed when the application of the reverse power to the first group is performed and the application of the reverse power to the second group is performed when the application of the forward power to the first group is performed; and outputting a thermal grill feedback by the thermoelectric couple array performing the heat generating operation and the heat absorbing operation.

Another aspect of the present disclosure is directed to feedback device for providing a thermal feedback, the device may include: a communication module communicating with an external device; a heat outputting module including a thermoelectric element provided as a thermoelectric couple array that includes a first thermoelectric couple group and a second thermoelectric couple group, a power terminal supplying a power to the thermoelectric element, and a contact surface which is provided on one side of the thermoelectric element and is configured to contact with a body part of a user, wherein the heat outputting module outputs the thermal feedback by transmitting, via the contact surface, a heat generated from the thermoelectric element to the user; and a feedback controller configured to: receive, via the communication module, a start message requesting outputting the thermal feedback, apply a forward power for a heat generating operation and a reverse power for a heat absorbing operation, alternatively to the first thermoelectric group, apply the forward power and the reverse power alternatively to the second thermoelectric group, and control the thermoelectric couple array to output a thermal grill feedback by applying the forward power to the first thermoelectric couple group and the reverse power to the second thermoelectric couple group simultaneously and applying the reverse power to the first thermoelectric couple group and the forward power to the second thermoelectric couple group simultaneously.

Another aspect of the present disclosure is directed to method for providing a thermal feedback, performed by a feedback device, wherein the feedback device includes a heat outputting module which is provided as a thermoelectric couple array including a plurality of thermoelectric couple groups and performs a thermoelectric operation, and a contact surface which is configured to contact with a body of a user and transmit a heat generated by the thermoelectric couple array, the method may include: applying a forward power for a heat generating operation to a first portion of the thermoelectric couple groups; applying a reverse power for a heat absorbing operation to a second portion of the thermoelectric couple groups when the forward power is applied to the first portion of the thermoelectric couple groups; and outputting a thermal grill feedback by the thermoelectric couple array performing the heat generating operation and the heat absorbing operation simultaneously, wherein a product of an area ratio of the second portion to the first portion another portion to the portion and a ratio of a temperature drop amount due to the heat absorbing operation to a temperature rise amount due to the heat generating operation is set to be more than 1.5 and less than 5.0.

Another aspect of the present disclosure is directed to feedback device for providing a thermal feedback, the device may include: a communication module communicating with an external device; a heat outputting module including a thermoelectric element provided as a thermoelectric couple array that includes a plurality of a thermoelectric couple groups, a power terminal supplying a power to the thermoelectric element, and a contact surface which is provided on one side of the thermoelectric element and is configured to contact with a body part of a user, wherein the heat outputting module outputs the thermal feedback by transmitting, via the contact surface, a heat generated from the thermoelectric element to the user; and a feedback controller configured to: receive, via the communication module, a start message requesting outputting the thermal feedback, and control the thermoelectric couple array to perform a heat generating operation and a heat absorbing operation together for outputting a thermal grill feedback by applying a forward power for the heat generating operation to a first portion of the thermoelectric couple groups and applying a reverse power for the heat absorbing operation to a second portion of the thermoelectric couple groups when the forward power is applied to the first portion, wherein a product of an area ratio of the second portion to the first portion another portion to the portion and a ratio of a temperature drop amount due to the heat absorbing operation to a temperature rise amount due to the heat generating operation is set to be more than 1.5 and less than 5.0.

Another aspect of the present disclosure is directed to gaming controller for outputting a thermal feedback, wherein the gaming controller cooperates with a content reproduction device executing a multimedia content including a game and an experience application, receives a user input related to the multimedia content, and provides a thermal experience related to the multimedia content by outputting the thermal feedback, the gaming controller may include: a casing having a grip portion gripped by a user and forming an exterior of the gaming controller; an input module receiving the user input according to a manipulation of the user; a communication module communicating with the content reproduction device; a heat outputting module including a thermoelectric element, that is provided as a thermoelectric couple array including a plurality of a thermoelectric couple groups and performs a thermoelectric operation including a heat generating operation and a heat absorbing operation, a power terminal supplying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: obtain, via the input module, the user input, send, via the communication module, the user input to the content reproduction device, receive, via the communication module, a feedback type information and a feedback intensity information from the content reproduction device, when the feedback type information indicates a hot feedback, apply, to the thermoelectric element, a first power of which a current direction is a forward direction, when the feedback type information indicates a cold feedback, apply, to the thermoelectric element, a second power of which a current direction is a reverse direction, and when the feedback type information indicates a thermal grill feedback and the feedback intensity information indicates a third intensity, apply a third power to one portion of the thermoelectric couple array and a fourth power to another portion of the thermoelectric couple array, wherein a current direction of the third power is the forward direction and a current direction of the fourth power is the reverse direction, wherein the third power has a voltage magnitude corresponding to a first intensity of the hot feedback and the fourth power has a voltage magnitude correspond to a second intensity of the cold feedback, and wherein the first intensity is smaller than the second intensity.

BRIEF DESCRIPTION OF THE DRAWINGS

The foregoing and other aspects, embodiments, examples, modes, types, and kinds of the present disclosure will be apparent to those skilled in the art to which the present disclosure relates based on the detailed descriptions that follow with reference to the accompanying drawings, wherein the same reference numerals are used in the several figures to refer to the same parts, elements and components and in which:

FIG. 32 is a table of operating voltages for providing the neutral grill feedback by an operating power control manner according to an embodiment of the present disclosure.

DETAILED DESCRIPTION

Figure 1:
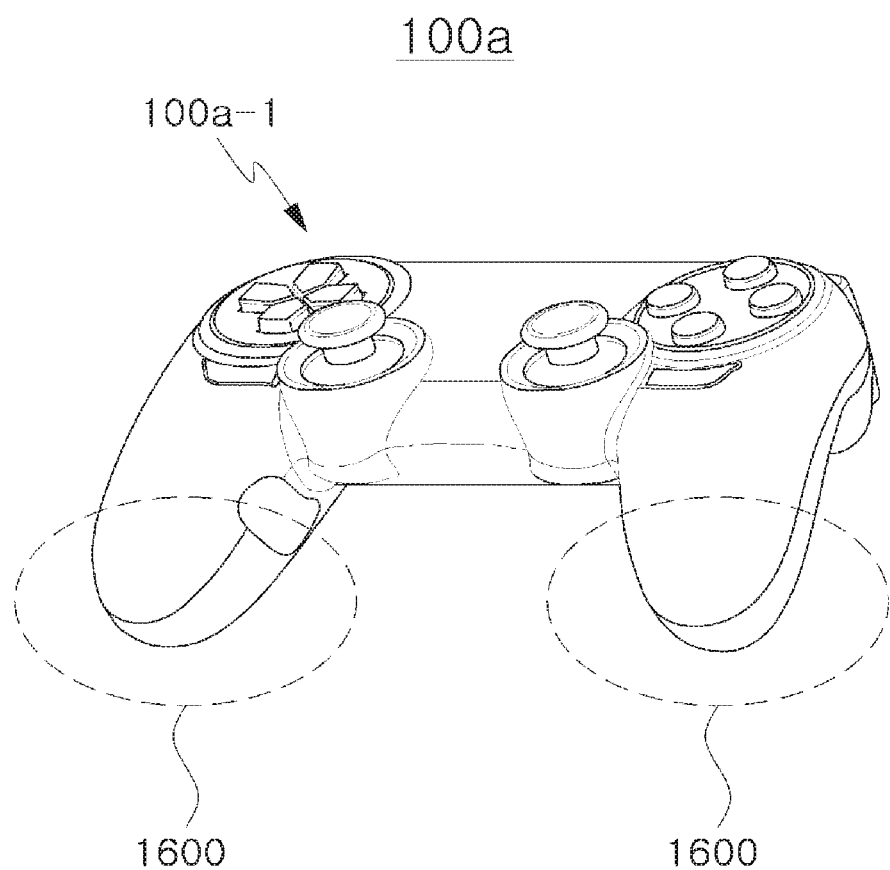
FIG. 1 illustrates a gaming controller as an implementation example of the feedback device according to an embodiment of the present disclosure.
Figure 2:
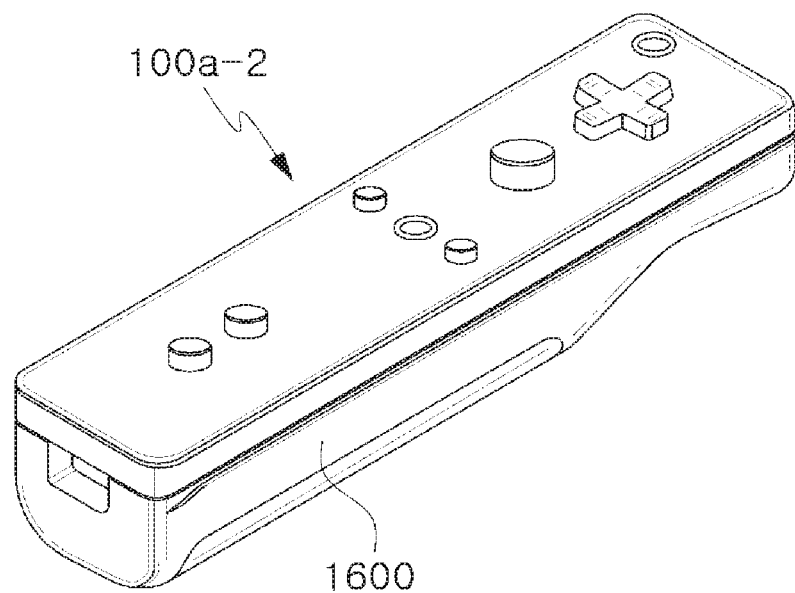
FIG. 2 illustrates another gaming controller as an implementation example of the feedback device according to an embodiment of the present disclosure.

It is to be understood that both the foregoing general description and the following detailed description are exemplary and explanatory and are not intended to limit the disclosure to the particular form disclosed, and should be interpreted to include modifications or variations that do not depart from the spirit of the present disclosure.

The terms used in the present specification should be interpreted based on the meaning of the term, in the context in which the term is used throughout the specification.

The drawings attached hereto are intended to illustrate the present disclosure, and the shapes shown in the drawings may be exaggerated to facilitate understanding of the present disclosure, and the present disclosure is thus not limited to the drawings.

In the following description, a detailed description of configurations or functions relating to the present disclosure that are known to those of ordinary skill may be omitted.

One aspect of the present disclosure is directed to method for providing a thermal feedback, performed by a feedback device, wherein the feedback device comprises a heat outputting module which is provided as a thermoelectric element and performs a thermoelectric operation including at least one of a heat generating operation and a heat absorbing operation and a contact surface which is configured to contact with a body of a user and transmit a heat generated by the thermoelectric operation, the method may include: applying an operating power to the thermoelectric element to start the thermoelectric operation for outputting the thermal feedback; stopping the application of the operating power to terminate the thermoelectric operation; and when the application of the operating power is stopped, applying a buffering power to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

The thermal inversion illusion may be felt by the user as if the temperature of the contact surface is opposite to a saturation temperature of the thermoelectric operation with respect to the initial temperature, even though the temperature of the contact surface is in fact in a same direction as the saturation temperature.

The buffering power may have a same current direction with the operating power.

The buffering power may have a smaller voltage magnitude than the operating power or the buffering power may have a smaller current magnitude than the operating power.

The method may further comprise: decreasing at least one of the voltage magnitude and the current magnitude of the buffering power during the application of the buffering power.

The buffering power may be provided as a form of a pulse width modulation (PWM) signal.

When the operating power is provided as a form of a PWM signal, a duty rate of the buffering power may be smaller than a duty rate of the operating power.

The method may further comprise: decreasing the duty rate of the buffering power during the application of the buffering power.

The thermoelectric element may be provided as a thermoelectric couple array including a plurality of thermoelectric couple groups and the buffering power may be applied to a part of the plurality of the thermoelectric couple group.

The number of the thermoelectric couple groups to which the buffering power is applied may be smaller than the number of the thermoelectric couple groups to which the operating power is applied.

The method may further comprise: reducing the number of the thermoelectric couple groups to which the buffering power is applied during the application of the buffering power.

Applying the buffering power may include applying the buffering power when a predetermined time has passed after the application of the operating power is stopped.

The feedback device may be configured to adjust an intensity of the thermal feedback and the applying the buffering power may be performed only when the intensity of the outputted thermal feedback is greater than the predetermined intensity.

The feedback device may be configured to adjust an intensity of the thermal feedback, and the method may further comprise: obtaining an information on the intensity of the thermal feedback; generating the operating power corresponding to the intensity of the thermal feedback based on the obtained information; and determining whether or not the applying the buffering power is performed based on whether or not the intensity of the thermal feedback is greater than a predetermined intensity.

Another aspect of the present disclosure is directed to feedback device for providing a thermal feedback, the device may include: a heat outputting module including a thermoelectric element performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: apply the operating power to the power terminal to start the thermoelectric operation for outputting the thermal feedback, stop the application of the operating power to terminate the thermoelectric operation, and when the application of the operating power is stopped, apply a buffering power to the power terminal to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

The thermal inversion illusion may be felt by the user as if the temperature of the contact surface is opposite to a saturation temperature of the thermoelectric operation with respect to the initial temperature even during the temperature of the contact surface being in a same direction with the saturation temperature.

The buffering power may have a same current direction with the operating power.

The buffering power may have a smaller voltage magnitude than the operating power or the buffering power may have a smaller current magnitude than the operating power.

The feedback controller may decrease at least one of the voltage magnitude and the current magnitude of the buffering power during the application of the buffering power.

The feedback controller may apply the buffering power as a form of a PWM signal.

When the operating power is provided as a form of a PWM signal, a duty rate of the buffering power may be smaller than a duty rate of the operating power.

The feedback controller may reduce the duty rate of the buffering power during the application of the buffering power.

The thermoelectric element may be provided as a thermoelectric couple array including a plurality of thermoelectric couple groups and the feedback device may apply the buffering power to a part of the plurality of the thermoelectric couple groups when applying the buffering power.

The number of the thermoelectric couple groups to which the buffering power is applied may be smaller than the number of the thermoelectric couple groups to which the operating power is applied.

Herein the feedback controller may reduce the number of the thermoelectric couple groups to which the buffering power is applied during the application of the buffering power.

The feedback controller may apply the buffering power when a predetermined time has passed after stopping the application of the operating power.

The heat outputting module may be configured to adjust an intensity of the thermal feedback and the feedback controller may apply the buffering power only when the intensity of the outputted thermal feedback is greater than the predetermined intensity.

The feedback controller may obtain an information on an intensity of the thermal feedback, generate the operating power corresponding to the intensity of the thermal feedback based on the obtained information, and determine whether to apply the buffering power based on whether the intensity of the thermal feedback is greater than a predetermined intensity.

Another aspect of the present disclosure is directed to method for providing a thermal feedback, performed by a feedback device, wherein the feedback device comprises a thermoelectric couple array that includes a plurality of thermoelectric couple groups and performs a thermoelectric operation including at least one of a heat generating operation and a heat absorbing operation and a contact surface which is configured to contact with a body of a user and transmit a heat generated by the thermoelectric operation, the method may include: applying an operating power to an operating group corresponding to at least a part of the plurality of the thermoelectric couple groups to start the thermoelectric operation for outputting the thermal feedback; stopping the application of the operating power for all the operating group to terminate the thermoelectric operation so that the thermal feedback ends; and performing, prior to the stopping, a buffering operation to reduce a temperature returning speed of the contact surface so that a thermal inversion illusion is prevented, wherein the buffering operation includes stopping the application of the operating power for a part of the operating group and maintaining the application of the operating power for a remainder of the operating group, and wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to feedback device for providing a thermal feedback, the device may include: a heat outputting module including a thermoelectric element which is provided as a thermoelectric couple array having a plurality of thermoelectric couple groups and performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: apply an operating power to an operating group corresponding to at least a part of the plurality of the thermoelectric couple groups to start the thermoelectric operation for outputting the thermal feedback, stop the application of the operating power for all the operating group to terminate the thermoelectric operation so that the thermal feedback ends, and perform a buffering operation to reduce a temperature returning speed of the contact surface so that a thermal inversion illusion is prevented, wherein the feedback controller performs the buffering operation, prior to stopping of the application of the operating power for all the operating group, by stopping the application of the operating power for a part of the operating group and maintaining the application of the operating power for a remainder of the operating group, and wherein the thermal inversion illusion is defined as an illusionary sensation felt by the user as a sensation opposite to the outputted thermal feedback during returning a temperature of the contact surface to an initial temperature due to the termination of the thermoelectric operation.

Another aspect of the present disclosure is directed to gaming controller, wherein the gaming controller is used as an input interface, of a content reproduction device reproducing a multimedia content, receiving a user input related to the multimedia content, and as an output interface, of the content reproduction device, providing a thermal experience related to the multimedia content by outputting a thermal feedback, the gaming controller may include: a casing having a grip portion gripped by a user and forming an exterior of the gaming controller; an input module receiving the user input according to a manipulation of the user; a communication module communicating with the content reproduction device; a heat outputting module including a thermoelectric element performing a thermoelectric operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: obtain, via the input module, the user input, send, via the communication module, the user input to the content reproduction device, receive, via the communication module, a feedback information from the content reproduction device, select one from predetermined voltage values as an operating voltage value based on an intensity of the feedback included in the feedback information, generate an operating power having the operating voltage value, apply the operating power to the heat outputting module so that the heat outputting module outputs the thermal feedback, stop the application of the operating power so that the heat outputting module stops outputting the thermal feedback, select one less than the operating voltage value from the predetermined voltage values as a buffering voltage, generate a buffering power having the buffering voltage value, and apply the buffering power to the heat outputting module to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

The controller may determine whether a current direction of the operating power based on whether a type of the thermal feedback is a hot feedback or a cold feedback, and determine a current direction of the buffering power to be same with the current direction of the operating power.

The intensity of the thermal feedback may include a first intensity and a second intensity greater than the first intensity and the predetermined voltage values may include a first voltage value and a second voltage value greater than the first voltage value. The controller may set the operating voltage value to the first voltage value when the intensity of the thermal feedback indicated by the feedback information is the first intensity and set the operating voltage value to the second voltage value when the intensity of the thermal feedback indicated by the feedback information is the second intensity. The controller may select the first voltage value as the voltage value of the buffering power when the application of the operating power having the second voltage value is stopped.

The controller may apply the buffering power only when the voltage value of the operating power is greater than the first voltage value.

The intensity of the thermal feedback further may include a third intensity greater than the second intensity and the predetermined voltage values may further include a third voltage value greater than the second voltage value. The controller may set the operating voltage value to the third voltage value when the intensity of the thermal feedback indicated by the feedback information is the third intensity. The controller may select the first voltage value as the voltage value of the buffering power when the application of the operating power having the third voltage value is stopped.

The intensity of the thermal feedback may further include a third intensity greater than the second intensity and the predetermined voltage values may further include a third voltage value greater than the second voltage value. The controller may set the operating voltage value to the third voltage value when the intensity of the thermal feedback indicated by the feedback information is the third intensity. The controller may select the first voltage value and the second voltage value as the voltage value of the buffering power when the application of the operating power having the third voltage value is stopped. The controller may apply the buffering power having the second voltage value when the application of the operating power is terminated and change the voltage value of the buffering power to the first voltage value when a predetermined time has passed from the termination of the application of the operating power.

Another aspect of the present disclosure is directed to method for providing a thermal feedback, performed by a feedback device, wherein the feedback device comprises a heat outputting module which is provided as a thermoelectric element and performs a thermoelectric operation including at least one of a heat generating operation and a heat absorbing operation and a contact surface which is configured to contact with a body of a user and transmit a heat generated by the thermoelectric operation, the method may include: obtaining an information on a type of the thermal feedback including a hot feedback and a cold feedback; applying an operating power according to the type of the thermal feedback to the thermoelectric element to start outputting of the thermal feedback; stopping the application of the operating power to terminate the outputting of the thermal feedback; generating a buffering power based on the type of the thermal feedback; and when the application of the operating power is stopped, applying the buffering power to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

A voltage magnitude of the buffering power may be smaller than a voltage magnitude of the operating power and set differently based on the type of the thermal feedback.

The generating may include generating the buffering power having a first voltage when the thermal feedback is the hot feedback and generating the buffering power having a second voltage of which a voltage magnitude is greater than a voltage magnitude of the first voltage.

The generating may include generating the buffering power having a first voltage when the thermal feedback is the hot feedback and generating the buffering power having a second voltage of which a voltage magnitude is smaller than a voltage magnitude of the first voltage.

A voltage magnitude of the buffering power may be smaller than a voltage magnitude of the operating power and a current direction of the buffering power may be set differently based on the type of the thermal feedback.

The generating may include generating the buffering power having a first current when the thermal feedback is the hot feedback and generating the buffering power having a second current of which a current magnitude is greater than a current magnitude of the first current.

The generating may include generating the buffering power having a first current when the thermal feedback is the hot feedback and generating the buffering power having a second current of which a current magnitude is smaller than a current magnitude of the first current.

A voltage magnitude ratio of the buffering power to the operating power may be smaller than 1 and set differently based on the type of the thermal feedback.

The applying may include applying the operating power having a first voltage when the thermal feedback is the hot feedback and applying the operating power having a second voltage when the thermal feedback is the cold feedback. The generating may include generating the buffering power having a third voltage when the thermal feedback is the hot feedback and generating the buffering power having a fourth voltage when the thermal feedback is the cold feedback. A ratio of the third voltage to the first voltage may be greater than a ratio of the fourth voltage to the second voltage.

The applying may include applying the operating power having a first voltage when the thermal feedback is the hot feedback and applying the operating power having a second voltage when the thermal feedback is the cold feedback. The generating may include generating the buffering power having a third voltage when the thermal feedback is the hot feedback and generating the buffering power having a fourth voltage when the thermal feedback is the cold feedback. A ratio of the third voltage to the first voltage may be smaller than a ratio of the fourth voltage to the second voltage.

A current magnitude ratio of the buffering power to the operating power may be smaller than 1 and set differently based on the type of the thermal feedback.

The applying may include applying the operating power having a first current when the thermal feedback is the hot feedback and applying the operating power having a second current when the thermal feedback is the cold feedback. The generating may include generating the buffering power having a third current when the thermal feedback is the hot feedback and generating the buffering power having a fourth current when the thermal feedback is the cold feedback. A current magnitude ratio of the third current to the first current may be greater than a ratio of the fourth current to the second current.

The applying may include applying the operating power having a first current when the thermal feedback is the hot feedback and applying the operating power having a second current when the thermal feedback is the cold feedback. The generating may include generating the buffering power having a third current when the thermal feedback is the hot feedback and generating the buffering power having a fourth current when the thermal feedback is the cold feedback. A current magnitude ratio of the third current to the first current may be smaller than a ratio of the fourth current to the second current.

Another aspect of the present disclosure is directed to method for providing a thermal feedback, performed by a feedback device, wherein the feedback device comprises a heat outputting module which is provided as a thermoelectric element and performs a thermoelectric operation including at least one of a heat generating operation and a heat absorbing operation and a contact surface which is configured to contact with a body of a user and transmit a heat generated by the thermoelectric operation, the method may include: obtaining an information on a type of the thermal feedback including a hot feedback and a cold feedback; applying an operating power according to the type of the thermal feedback to the thermoelectric element to start outputting of the thermal feedback; stopping the application of the operating power to terminate the outputting of the thermal feedback; obtaining a buffering duration which is set differently based on the type of the thermal feedback; and when the application of the operating power is stopped, applying a buffering power for the buffering duration to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

The applying may include applying the buffering power for a first duration when the thermal feedback is the hot feedback and applying the buffering power for a second duration which is greater than the first duration when the thermal feedback is the cold feedback.

The applying may include applying the buffering power for a first duration when the thermal feedback is the hot feedback and applying the buffering power for a second duration which is smaller than the first duration when the thermal feedback is the cold feedback.

Another aspect of the present disclosure is directed to method for providing a thermal feedback, performed by a feedback device, wherein the feedback device comprises a thermoelectric couple array that includes a plurality of thermoelectric couple groups and performs a thermoelectric operation including a heat generating operation and a heat absorbing operation and a contact surface which is configured to contact with a body of a user and transmit a heat generated by the thermoelectric operation, the method may include: obtaining an information on a type of the thermal feedback including a hot feedback and a cold feedback; applying an operating power according to the type of the thermal feedback to an operating group to start outputting of the thermal feedback, the operating group including at least part of the plurality of the thermoelectric couple groups; stopping the application of the operating power to terminate the outputting of the thermal feedback; determining a buffering group based on the type of the thermoelectric operation, the buffering group including at least part of the plurality of the thermoelectric couple groups, wherein the number of the thermoelectric couple groups included in the buffering group is smaller than the number of the thermoelectric couple groups included in the operating group; and when the application of the operating power is stopped, applying a buffering power to the buffering group to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

The buffering group may include a first number of the thermoelectric couple groups when the thermal feedback is the hot feedback and the buffering group may include a second number of the thermoelectric couple groups, the second number being greater than the first number.

The buffering group may include a first number of the thermoelectric couple groups when the thermal feedback is the hot feedback and the buffering group may include a second number of the thermoelectric couple groups, the second number being smaller than the first number.

Another aspect of the present disclosure is directed to method for providing a thermal feedback, performed by a feedback device, wherein the feedback device comprises a thermoelectric couple array that includes a plurality of thermoelectric couple groups and performs a thermoelectric operation including a heat generating operation and a heat absorbing operation and a contact surface which is configured to contact with a body of a user and transmit a heat generated by the thermoelectric operation, the method may include: obtaining an information on a type of the thermal feedback including a hot feedback and a cold feedback; applying an operating power according to the type of the thermal feedback to an operating group to start outputting of the thermal feedback, the operating group including at least part of the plurality of the thermoelectric couple groups; stopping the application of the operating power to terminate the outputting of the thermal feedback; and performing a buffering operation to reduce a temperature returning speed of the contact surface upon the stopping of the application of the operating power so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation, and wherein the buffering operation is performed, before the application of the operating power related to all of the operating group is stopped, by maintaining the application of the operating power to a part of the operating group and stopping the application of the operating power to the rest of the operating group.

Another aspect of the present disclosure is directed to feedback device for providing a thermal feedback, the device may include: a heat outputting module including a thermoelectric element performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: obtain an information on a type of the thermal feedback including a hot feedback and a cold feedback, apply an operating power according to the type of the thermal feedback to the thermoelectric element to start outputting of the thermal feedback, stop the application of the operating power to terminate the outputting of the thermal feedback, generate a buffering power based on the type of the thermal feedback, and when the application of the operating power is stopped, apply the buffering power to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

A voltage magnitude of the buffering power may be smaller than a voltage magnitude of the operating power and set differently based on the type of the thermal feedback.

The buffering power may have a first voltage when the thermal feedback is the hot feedback and the buffering power may have a second voltage of which a voltage magnitude is greater than a voltage magnitude of the first voltage when the thermal feedback is the cold feedback.

The buffering power may have a first voltage when the thermal feedback is the hot feedback and the buffering power may have a second voltage of which a voltage magnitude is smaller than a voltage magnitude of the first voltage when the thermal feedback is the cold feedback.

A voltage magnitude of the buffering power may be smaller than a voltage magnitude of the operating power and a current direction of the buffering power may be set differently based on the type of the thermal feedback.

The buffering power may have a first current when the thermal feedback is the hot feedback and the buffering power may have a second current of which a current magnitude is greater than a current magnitude of the first current when the thermal feedback is the cold feedback.

The buffering power may have a first current when the thermal feedback is the hot feedback and the buffering power may have a second current of which a current magnitude is smaller than a current magnitude of the first current when the thermal feedback is the cold feedback.

A voltage magnitude ratio of the buffering power to the operating power may be smaller than 1 and set differently based on the type of the thermal feedback.

The operating power may have a first voltage when the thermal feedback is the hot feedback and the operating power may have a second voltage when the thermal feedback is the cold feedback. The buffering power may have a third voltage when the thermal feedback is the hot feedback and the buffering power may have a fourth voltage when the thermal feedback is the cold feedback. A ratio of the third voltage to the first voltage may be greater than a ratio of the fourth voltage to the second voltage.

The operating power may have a first voltage when the thermal feedback is the hot feedback and the operating power may have a second voltage when the thermal feedback is the cold feedback. The buffering power may have a third voltage when the thermal feedback is the hot feedback and the buffering power may have a fourth voltage when the thermal feedback is the cold feedback. A ratio of the third voltage to the first voltage may be smaller than a ratio of the fourth voltage to the second voltage.

A current magnitude ratio of the buffering power to the operating power may be smaller than 1 and set differently based on the type of the thermal feedback.

The operating power may have a first current when the thermal feedback is the hot feedback and the operating power may have a second current when the thermal feedback is the cold feedback. The buffering power may have a third current when the thermal feedback is the hot feedback and the buffering power may have a fourth current when the thermal feedback is the cold feedback. A current magnitude ratio of the third current to the first current may be greater than a ratio of the fourth current to the second current.

The operating power may have a first current when the thermal feedback is the hot feedback and the operating power may have a second current when the thermal feedback is the cold feedback. The buffering power may have a third current when the thermal feedback is the hot feedback and the buffering power may have a fourth current when the thermal feedback is the cold feedback. A current magnitude ratio of the third current to the first current may be smaller than a ratio of the fourth current to the second current.

Another aspect of the present disclosure is directed to feedback device for providing a thermal feedback, the device may include: a heat outputting module including a thermoelectric element performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: obtain an information on a type of the thermal feedback including a hot feedback and a cold feedback, apply an operating power according to the type of the thermal feedback to the thermoelectric element to start outputting of the thermal feedback, stop the application of the operating power to terminate the outputting of the thermal feedback, obtain a buffering duration which is set differently based on the type of the thermal feedback, and when the application of the operating power is stopped, apply a buffering power for the buffering duration to the thermoelectric element to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

The buffering duration may be a first duration when the thermal feedback is the hot feedback and the buffering duration may be a second duration which is greater than the first duration when the thermal feedback is the cold feedback.

The buffering duration may be a first duration when the thermal feedback is the hot feedback and the buffering duration may be a second duration which is smaller than the first duration when the thermal feedback is the cold feedback.

Another aspect of the present disclosure is directed to feedback device for providing a thermal feedback, the device may include: a heat outputting module including a thermoelectric couple array that includes a plurality of the thermoelectric couple groups and performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: obtain an information on a type of the thermal feedback including a hot feedback and a cold feedback, apply an operating power according to the type of the thermal feedback to an operating group to start outputting of the thermal feedback, the operating group including at least part of the plurality of the thermoelectric couple groups, stop the application of the operating power to terminate the outputting of the thermal feedback, determine a buffering group based on the type of the thermoelectric operation, the buffering group including at least part of the plurality of the thermoelectric couple groups, wherein the number of the thermoelectric couple groups included in the buffering group is smaller than the number of the thermoelectric couple groups included in the operating group, and when the application of the operating power is stopped, apply a buffering power to the buffering group to reduce a temperature returning speed of the contact surface so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation.

The buffering group may include a first number of the thermoelectric couple groups when the thermal feedback is the hot feedback and the buffering group may include a second number of the thermoelectric couple groups, the second number being greater than the first number.

The buffering group may include a first number of the thermoelectric couple groups when the thermal feedback is the hot feedback and the buffering group may include a second number of the thermoelectric couple groups, the second number being smaller than the first number.

Another aspect of the present disclosure is directed to feedback device for providing a thermal feedback, the device may include: a heat outputting module including a thermoelectric couple array that includes a plurality of the thermoelectric couple groups and performing a thermoelectric operation including at least one of a heat generating operation and a heat absorbing operation, a power terminal supplying an operating power for the thermoelectric operation to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: obtain an information on a type of the thermal feedback including a hot feedback and a cold feedback, apply an operating power according to the type of the thermal feedback to an operating group to start outputting of the thermal feedback, the operating group including at least part of the plurality of the thermoelectric couple groups, stop the application of the operating power to terminate the outputting of the thermal feedback; and perform a buffering operation to reduce a temperature returning speed of the contact surface upon the stopping of the application of the operating power so that a thermal inversion illusion is prevented, wherein the thermal inversion illusion is defined as an illusionary sensation felt by the user as a sensation opposite to the outputted thermal feedback during returning a temperature of the contact surface to an initial temperature due to the termination of the thermoelectric operation, and wherein the buffering operation is performed, before the application of the operating power related to all of the operating group is stopped, by maintaining the application of the operating power to a part of the operating group and stopping the application of the operating power to the rest of the operating group.

Another aspect of the present disclosure is directed to method for providing a thermal feedback including a hot feedback, a cold feedback and a thermal grill feedback, performed by a feedback device, wherein the feedback device comprises a thermoelectric couple array that includes a plurality of thermoelectric couple groups and performs a thermoelectric operation including a heat generating operation, a heat absorbing operation and a thermal grill operation in which the heat generating operation and the heat absorbing operation is combined and a contact surface which is configured to contact with a body of a user and transmit a heat generated by the thermoelectric operation, the method may include: applying a forward power to a first group of the plurality of the thermoelectric couple groups to perform the heat generating operation and a reverse power to a second group of the plurality of the thermoelectric couple groups to perform the heat absorbing operation so that the thermoelectric couple array performs the thermal grill operation and starts outputting of the thermal grill feedback; and stopping the application of the forward power and the application of the reverse power, wherein the application of the forward power and the application of the reverse power are stopped at different time points.

A first portion of the contact surface and a second portion of the contact surface may return to a thermal equilibrium state at a substantially same time by stopping the application of the forward power and the reverse power at the different time points. The first portion may be adjacent to the first group performing the heat generating operation and a second portion may be adjacent to the second group performing the heat absorbing operation.

A voltage magnitude or a current magnitude of the reverse power may be greater than a voltage magnitude or a current magnitude of the forward power so that a temperature rise amount of the first group according to the heat generating operation may be smaller than a temperature drop amount of the second group according to the heat absorbing operation and the user may be prevented from feeling a hot sensation or a cold sensation when the thermal grill feedback is provided to the user. The application of the reverse power may be stopped before the application of the forward voltage is stopped so that the first group of which the temperature rise amount may be smaller than the temperature drop amount of the second group and the second group may return to the thermal equilibrium state at an initial temperature.

The application of the forward power may be stopped before the application of the reverse power is stopped to prevent the contact surface from reaching the thermal equilibrium state at a temperature higher than an initial temperature due to a waste heat of the thermoelectric operation.

Another aspect of the present disclosure is directed to feedback device for providing a thermal feedback, the device may include: a heat outputting module including a thermoelectric element provided as a thermoelectric couple array that includes a first thermoelectric couple group performing a heat generating operation and a second thermoelectric couple group performing a heat absorbing operation, a power terminal supplying a power to the thermoelectric element, and a contact surface which is provided on one side of the thermoelectric element and is configured to contact with a body part of a user, wherein the heat outputting module outputs the thermal grill feedback by transmitting, via the contact surface, a hot heat according to the heat generating operation and a cold heat according to the heat absorbing operation to the user; and a feedback controller configured to: apply a forward power to a first thermoelectric couple group and a reverse power to a second thermoelectric couple group so that the thermoelectric element performs the thermal grill operation and starts outputting of the thermal grill feedback, and stop the application of the forward power and the application of the reverse power, wherein the application of the forward power and the application of the reverse power are stopped at different time points.

The feedback controller may adjust a first time point related to stopping of the application of the forward power and a second time point related to stopping of the application of the reverse power differently so that a first portion of the contact surface and a second portion of the contact surface may reach a thermal equilibrium state at a substantially same time. The first portion may be adjacent to the first thermoelectric couple group performing the heat generating operation and a second portion may be adjacent to the second thermoelectric couple group performing the heat absorbing operation.

The feedback controller may adjust the reverse power to have a voltage magnitude or a current magnitude greater than the forward power so that a temperature rise amount of the first thermoelectric couple group according to the heat generating operation may be smaller than a temperature drop amount of the second thermoelectric group according to the heat absorbing operation and the user may be prevented from feeling a hot sensation or a cold sensation when the thermal grill feedback is provided to the user, and stop the application of the reverse power before stopping the application of the forward voltage so that the first thermoelectric couple group of which the temperature rise amount may be greater than the temperature drop amount of the second thermoelectric couple group and the second group may return to the thermal equilibrium state at an initial temperature.

The feedback controller may prevent the contact surface from reaching the thermal equilibrium state at a temperature higher than an initial temperature due to a waste heat of the thermoelectric operation, by stopping the application of the forward power before stopping the application of the reverse power.

Another aspect of the present disclosure is directed to method for providing a thermal feedback including a hot feedback, a cold feedback and a thermal grill feedback, performed by a feedback device, wherein the feedback device comprises a thermoelectric couple array that includes a plurality of thermoelectric couple groups and performs a thermoelectric operation including a heat generating operation, a heat absorbing operation and a thermal grill operation in which the heat generating operation and the heat absorbing operation is combined and a contact surface which is configured to contact with a body of a user and transmit a heat generated by the thermoelectric operation, the method may include: applying a forward power to a first group of the plurality of the thermoelectric couple groups to perform the heat generating operation and a reverse power to a second group of the plurality of the thermoelectric couple groups to perform the heat absorbing operation so that the thermoelectric couple array performs the thermal grill operation and starts outputting of the thermal grill feedback; stopping the application of the forward power and the application of the reverse power in order to terminate outputting of the thermal grill feedback; and applying a compensation power to at least one of the first group and the second group so that the contact surface returns to an initial temperature.

The application of the forward power and the application of the reverse power may be stopped at substantially a same time, e.g., within a certain number of clock cycles.

A voltage magnitude or a current magnitude of the reverse power may be greater than a voltage magnitude or a current magnitude of the forward power so that a temperature rise amount of the first group according to the heat generating operation may be smaller than a temperature drop amount of the second group according to the heat absorbing operation and the user may be prevented from feeling a hot sensation or a cold sensation when the thermal grill feedback is provided to the user. The compensation power may have a same current direction with the forward power so that the first group of which the temperature rise amount may be smaller than the temperature drop amount of the second group and the second group may reach the thermal equilibrium state at an initial temperature.

A voltage magnitude or a current magnitude of the reverse power may be greater than a voltage magnitude or a current magnitude of the forward power so that a temperature rise amount of the first group according to the heat generating operation may be smaller than a temperature drop amount of the second group according to the heat absorbing operation and the user may be prevented from feeling a hot sensation or a cold sensation when the thermal grill feedback is provided to the user. The applying the compensation power may include applying a first compensation power to the first group and applying a second compensation power to the second group of which a current direction is opposite to the first compensation power. One having a same current direction with the forward power among the first compensation power and the second compensation power may have at least of a voltage magnitude, a current magnitude and an application duration greater than the other of the first compensation power and the second compensation power.

The compensation power may have a same current direction with the reverse power to prevent the contact surface from reaching the thermal equilibrium state at a temperature higher than an initial temperature due to a waste heat of the thermoelectric operation.

The applying the compensation power may include applying a first compensation power to the first group and applying a second compensation power to the second group of which a current direction is opposite to a current direction of the first compensation power. One having a same current direction with the reverse power among the first compensation power and the second compensation power may have at least of a voltage magnitude, a current magnitude and an application duration greater than the other of the first compensation power and the second compensation power.

Another aspect of the present disclosure is directed to feedback device for providing a thermal feedback, the device may include: a heat outputting module including a thermoelectric element provided as a thermoelectric couple array that includes a first thermoelectric couple group performing a heat generating operation and a second thermoelectric couple group performing a heat absorbing operation, a power terminal supplying a power to the thermoelectric element, and a contact surface which is provided on one side of the thermoelectric element and is configured to contact with a body part of a user, wherein the heat outputting module outputs the thermal grill feedback by transmitting, via the contact surface, a hot heat according to the heat generating operation and a cold heat according to the heat absorbing operation to the user; and a feedback controller configured to: apply a forward power to the first thermoelectric couple group to perform the heat generating operation and a reverse power to a second thermoelectric couple group to perform the heat absorbing operation so that the thermoelectric couple array performs the thermal grill operation and starts outputting of the thermal grill feedback, stop the application of the forward power and the reverse power in order to terminate outputting of the thermal grill feedback, and apply a compensation power to at least one of the first thermoelectric couple group and the second thermoelectric couple group so that the contact surface returns to an initial temperature.

The feedback controller may stop the application of the forward power and the application of the reverse power at substantially a same time, e.g., within a certain number of clock cycles.

The feedback controller may adjust the reverse power to have a voltage magnitude or a current magnitude greater than the forward power so that a temperature rise amount of the first thermoelectric couple group according to the heat generating operation may be smaller than a temperature drop amount of the second thermoelectric couple group according to the heat absorbing operation and the user may be prevented from feeling a hot sensation or a cold sensation when the thermal grill feedback is provided to the user. The feedback controller may adjust the compensation power to have a same current direction with the forward power so that the first thermoelectric couple group of which the temperature rise amount may be smaller than the temperature drop amount of the second thermoelectric couple group and the second thermoelectric couple group may reach the thermal equilibrium state at an initial temperature.

The feedback controller may adjust the reverse power to have a voltage magnitude or a current magnitude greater than the forward power so that a temperature rise amount of the first thermoelectric couple group according to the heat generating operation may be smaller than a temperature drop amount of the second thermoelectric couple group according to the heat absorbing operation and the user may be prevented from feeling a hot sensation or a cold sensation when the thermal grill feedback is provided to the user. The feedback controller may apply a first compensation power to the first thermoelectric couple group and a second compensation power of which a current direction is opposite to the first compensation power. One having a same current direction with the forward power among the first compensation power and the second compensation power may have at least of a voltage magnitude, a current magnitude and an application duration greater than the other of the first compensation power and the second compensation power.

The feedback controller may apply the compensation power having a same current direction with the reverse power to prevent the contact surface from reaching the thermal equilibrium state at a temperature higher than an initial temperature due to a waste heat of the thermoelectric operation.

The feedback controller may apply a first compensation power to the first thermoelectric couple group and a second compensation power to the second thermoelectric couple group of which a current direction is opposite to a current direction of the first compensation power. One having a same current direction with the reverse power among the first compensation power and the second compensation power may have at least of a voltage magnitude, a current magnitude and an application duration greater than the other of the first compensation power and the second compensation power.

Another aspect of the present disclosure is directed to method for providing a thermal feedback, performed by a feedback device, wherein the feedback device comprises a heat outputting module which is provided as a thermoelectric element and performs a thermoelectric operation including at least one of a heat generating operation and a heat absorbing operation and a contact surface which is configured to contact with a body of a user and transmit a heat generated by the thermoelectric operation, the method may include: obtaining a start message requesting outputting the thermal feedback; applying, upon the obtaining the start message, an operating power to the thermoelectric element to start outputting the thermal feedback which corresponds to the start message; stopping the application of the operating power to terminate the thermoelectric operation; when the application of the operating power is stopped, performing a buffering operation reducing a temperature returning speed of the contact surface for preventing a thermal inversion illusion due to the termination of the thermoelectric operation, wherein the thermal inversion illusion is defined as an illusionary sensation felt by the user as a sensation opposite to the outputted thermal feedback during returning a temperature of the contact surface to an initial temperature due to the termination of the thermoelectric operation; and when a new start message is obtained during performing the buffering operation, stopping the buffering operation and applying the operating power to the thermoelectric element to start outputting the thermal feedback which corresponds to the new start message.

The start message may include a providing duration of the thermal feedback, and the stopping the application of the operating power may be performed after the operating power is applied for the providing duration.

Here, the method may further comprise: obtaining an end message requesting terminating the thermal feedback, and the stopping the application of the operating power may performed upon the obtaining the end message.

The stopping the application of the operating power may be performed after the operating power is applied for a predetermined duration.

The buffering operation may be performed by reducing a voltage magnitude or a current magnitude of the operating power.

The thermoelectric element may be provided as a thermoelectric couple array which includes a plurality of thermoelectric couple groups which are controlled individually, and the buffering operation may be performed by reducing the number of the thermoelectric couple groups to which the operating power is applied.

Another aspect of the present disclosure is directed to feedback device for providing a thermal feedback, the device may include: a communication module communicating with a content reproduction device executing a multimedia content including a game and an experience application; a heat outputting module including a thermoelectric element performing a thermoelectric operation including at least one of a heat generating operation and a heat absorbing operation, a power terminal supplying a power to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user so that a thermal experience related to the multimedia is provided to the user; and a feedback controller configured to: receive, via the communication module, a start message requesting outputting the thermal feedback, apply, upon the receipt of the start message, an operating power to the thermoelectric element to start outputting the thermal feedback which corresponds to the start message, stop the application of the operating power to terminate the thermoelectric operation, when the application of the operating power is stopped, perform a buffering operation reducing a temperature returning speed of the contact surface for preventing a thermal inversion illusion due to the termination of the thermoelectric operation, wherein the thermal inversion illusion is defined as an illusionary sensation felt by the user as a sensation opposite to the outputted thermal feedback during returning a temperature of the contact surface to an initial temperature due to the termination of the thermoelectric operation, and when a new start message is received during performing the buffering operation, stop the buffering operation and apply the operating power to the thermoelectric element to start outputting the thermal feedback which corresponds to the new start message.

The start message may include a providing duration of the thermal feedback, and the feedback controller may stop the application of the operating power after applying the operating power for the providing duration.

The feedback controller may receive, via the communication module, an end message requesting terminating the thermal feedback, and stop the application of the operating power upon the receipt of the end message.

The feedback controller may stop the application of the operating power after applying the operating power for a predetermined duration.

The feedback controller may perform the buffering operation by reducing a voltage magnitude or a current magnitude of the operating power.

The thermoelectric element may be provided as a thermoelectric couple array which includes a plurality of thermoelectric couple groups which are controlled individually. The feedback device may perform the buffering operation by reducing the number of the thermoelectric couple groups to which the operating power is applied.

Another aspect of the present disclosure is directed to method for providing a thermal feedback, performed by a feedback device, wherein the feedback device outputs the thermal feedback by transmitting a heat generated by a thermoelectric element, to a user via a contact surface contacting with a body part of the user, the method may include: obtaining a feedback start message including a type of the thermal feedback; and when the type of the thermal feedback is a thermal grill feedback, outputting the thermal grill feedback by performing a thermal grill operation in which a heat generating operation and a heat absorbing operation is combined, wherein the outputting includes applying a forward power to the thermoelectric element to perform the heat generating operation, applying a reverse power of which a current direction is opposite to the forward power to the thermoelectric element to perform the heat absorbing operation, and the application of the forward power and the application of the reverse power is repeated alternatively.

Each of an application duration of the forward voltage and an application duration of the reverse voltage may be smaller than a perception time in which the user may feel a hot sensation according to the heat generating operation or a cold sensation according to the heat absorbing operation.

An application duration of the forward power may be smaller than an application duration of the reverse power to prevent the user from feeling a hot sensation or a cold sensation when the thermal grill feedback is provided to the user.

A ratio of the application duration of the reverse power to the application duration of the forward power may be more than 1.5 and less than 5.0.

An application duration of the forward power and an application duration of the reverse power may be set to be same and a voltage magnitude or a current magnitude of the forward power may be set to be smaller than a voltage magnitude or a current magnitude of the reverse power in order to adjust a temperature rise amount of the contact surface according to the application of the forward power to be smaller than a temperature drop amount of the contact surface according to the application of the reverse power.

A voltage magnitude of at least one of the forward power and the reverse power be set to adjust a ratio of the temperature drop amount to the temperature rise amount to be more than 1.5 and less than 5.0.

A product of a ratio of an application duration of the reverse power to an application duration of the forward power and a ratio of a temperature drop amount to the temperature rise amount may be more than 1.5 and less than 5.0.

Another aspect of the present disclosure is directed to feedback device for providing a thermal feedback, the device may include: a communication module communicating with an external device; a heat outputting module including a thermoelectric element performing a heat generating operation and a heat absorbing operation, a power terminal supplying a power to the thermoelectric element and a contact surface which is provided on one side of the thermoelectric element and is configured to contact with a body part of a user, wherein the heat outputting module outputs the thermal feedback by transmitting, via the contact surface, a heat generated due to the heat generating operation or the heat absorbing operation; and a feedback controller configured to: receive, via the communication module, a feedback start message including a type of the thermal feedback, when the type of the thermal feedback may be a thermal grill feedback, and output the thermal grill feedback by performing a thermal grill operation in which the heat generating operation and the heat absorbing operation is combined, wherein the feedback controller applies a forward power to the thermoelectric element to perform the heat generating operation and a reverse power of which a current direction is opposite to the forward power to the thermoelectric element to perform the heat absorbing operation and repeats the application of the forward power and the application of the reverse power alternatively so that the heat outputting module outputs the thermal grill feedback.

Each of an application duration of the forward voltage and an application duration of the reverse voltage may be smaller than a perception time in which the user may feel a hot sensation according to the heat generating operation or a cold sensation according to the heat absorbing operation.

The feedback controller may adjust an application duration of the forward power to be smaller than an application duration of the reverse power to prevent the user from feeling a hot sensation or a cold sensation when the thermal grill feedback is provided to the user.

A ratio of the application duration of the reverse power to the application duration of the forward power may be more than 1.5 and less than 5.0.

The feedback controller may adjust an application duration of the forward power and an application duration of the reverse power to be same, and set the forward power to have a voltage magnitude or a current magnitude smaller than the reverse power to adjust a temperature rise amount of the contact surface according to the application of the forward power to be smaller than a temperature drop amount of the contact surface according to the application of the reverse power.

The feedback controller may set a voltage magnitude of at least one of the forward power and the reverse power to adjust a ratio of the temperature drop amount to the temperature rise amount to be more than 1.5 and less than 5.0.

A product of a ratio of an application duration of the reverse power to an application duration of the forward power and a ratio of a temperature drop amount to the temperature rise amount may be more than 1.5 and less than 5.0.

Another aspect of the present disclosure is directed to method for providing a thermal feedback, performed by a feedback device, wherein the feedback device comprises a heat outputting module which is provided as a thermoelectric couple array including a plurality of thermoelectric couple groups and performs a thermoelectric operation, and a contact surface which is configured to contact with a body of a user and transmit a heat generated by the thermoelectric couple array, the method may include: applying a forward power for a heat generating operation and a reverse power for a heat absorbing operation, alternatively to a first group of the plurality of the thermoelectric couple groups; applying the forward power and the reverse power alternatively to a second group of the plurality of the thermoelectric couple groups, wherein the application of the forward power to the second group is performed when the application of the reverse power to the first group is performed and the application of the reverse power to the second group is performed when the application of the forward power to the first group is performed; and outputting a thermal grill feedback by the thermoelectric couple array performing the heat generating operation and the heat absorbing operation.

An alternating cycle of the forward power and the reverse power may be greater than a delay time from the start of the application of the forward power and the reverse power until the contact surface reaches a temperature at which the user senses the thermal feedback.

An application duration of the forward power and an application duration of the reverse power may be set to be same, a voltage magnitude or a current magnitude of the forward power may be set to be smaller than a voltage magnitude or a current magnitude of the reverse power in order to adjust a temperature rise amount of the contact surface according to the application of the forward power to be smaller than a temperature drop amount of the contact surface according to the application of the reverse power.

A voltage magnitude of at least one of the forward power and the reverse power may be set to adjust a ratio of the temperature drop amount to the temperature rise amount to be more than 1.5 and less than 5.0.

Another aspect of the present disclosure is directed to feedback device for providing a thermal feedback, the device may include: a communication module communicating with an external device; a heat outputting module including a thermoelectric element provided as a thermoelectric couple array that includes a first thermoelectric couple group and a second thermoelectric couple group, a power terminal supplying a power to the thermoelectric element, and a contact surface which is provided on one side of the thermoelectric element and is configured to contact with a body part of a user, wherein the heat outputting module outputs the thermal feedback by transmitting, via the contact surface, a heat generated from the thermoelectric element to the user; and a feedback controller configured to: receive, via the communication module, a start message requesting outputting the thermal feedback, apply a forward power for a heat generating operation and a reverse power for a heat absorbing operation, alternatively to the first thermoelectric group, apply the forward power and the reverse power alternatively to the second thermoelectric group, and control the thermoelectric couple array to output a thermal grill feedback by applying the forward power to the first thermoelectric couple group and the reverse power to the second thermoelectric couple group simultaneously and applying the reverse power to the first thermoelectric couple group and the forward power to the second thermoelectric couple group simultaneously.

An alternating cycle of the forward power and the reverse power may be greater than a delay time from the start of the application of the forward power and the reverse power until the contact surface reaches a temperature at which the user senses the thermal feedback.

The feedback controller may adjust an application duration of the forward power and an application duration of the reverse power to be same, and set the forward power to have a voltage magnitude or a current magnitude smaller than the reverse power to adjust a temperature rise amount of the contact surface according to the application of the forward power to be smaller than a temperature drop amount of the contact surface according to the application of the reverse power.

The feedback controller may set a voltage magnitude of at least one of the forward power and the reverse power in order to adjust a ratio of the temperature drop amount to the temperature rise amount to be more than 1.5 and less than 5.0.

Another aspect of the present disclosure is directed to method for providing a thermal feedback, performed by a feedback device, wherein the feedback device comprises a heat outputting module which is provided as a thermoelectric couple array including a plurality of thermoelectric couple groups and performs a thermoelectric operation, and a contact surface which is configured to contact with a body of a user and transmit a heat generated by the thermoelectric couple array, the method may include: applying a forward power for a heat generating operation to a first portion of the thermoelectric couple groups; applying a reverse power for a heat absorbing operation to a second portion of the thermoelectric couple groups when the forward power is applied to the first portion of the thermoelectric couple groups; and outputting a thermal grill feedback by the thermoelectric couple array performing the heat generating operation and the heat absorbing operation simultaneously, wherein a product of an area ratio of the second portion to the first portion another portion to the portion and a ratio of a temperature drop amount due to the heat absorbing operation to a temperature rise amount due to the heat generating operation is set to be more than 1.5 and less than 5.0.

Another aspect of the present disclosure is directed to feedback device for providing a thermal feedback, the device may include: a communication module communicating with an external device; a heat outputting module including a thermoelectric element provided as a thermoelectric couple array that includes a plurality of a thermoelectric couple groups, a power terminal supplying a power to the thermoelectric element, and a contact surface which is provided on one side of the thermoelectric element and is configured to contact with a body part of a user, wherein the heat outputting module outputs the thermal feedback by transmitting, via the contact surface, a heat generated from the thermoelectric element to the user; and a feedback controller configured to: receive, via the communication module, a start message requesting outputting the thermal feedback, and control the thermoelectric couple array to perform a heat generating operation and a heat absorbing operation together for outputting a thermal grill feedback by applying a forward power for the heat generating operation to a first portion of the thermoelectric couple groups and applying a reverse power for the heat absorbing operation to a second portion of the thermoelectric couple groups when the forward power is applied to the first portion, wherein a product of an area ratio of the second portion to the first portion another portion to the portion and a ratio of a temperature drop amount due to the heat absorbing operation to a temperature rise amount due to the heat generating operation is set to be more than 1.5 and less than 5.0.

Another aspect of the present disclosure is directed to gaming controller for outputting a thermal feedback, wherein the gaming controller cooperates with a content reproduction device executing a multimedia content including a game and an experience application, receives a user input related to the multimedia content, and provides a thermal experience related to the multimedia content by outputting the thermal feedback, the gaming controller may include: a casing having a grip portion gripped by a user and forming an exterior of the gaming controller; an input module receiving the user input according to a manipulation of the user; a communication module communicating with the content reproduction device; a heat outputting module including a thermoelectric element, that is provided as a thermoelectric couple array including a plurality of a thermoelectric couple groups and performs a thermoelectric operation including a heat generating operation and a heat absorbing operation, a power terminal supplying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: obtain, via the input module, the user input, send, via the communication module, the user input to the content reproduction device, receive, via the communication module, a feedback type information and a feedback intensity information from the content reproduction device, when the feedback type information indicates a hot feedback, apply, to the thermoelectric element, a first power of which a current direction is a forward direction, when the feedback type information indicates a cold feedback, apply, to the thermoelectric element, a second power of which a current direction is a reverse direction, and when the feedback type information indicates a thermal grill feedback and the feedback intensity information indicates a third intensity, apply a third power to one portion of the thermoelectric couple array and a fourth power to another portion of the thermoelectric couple array, wherein a current direction of the third power is the forward direction and a current direction of the fourth power is the reverse direction, wherein the third power has a voltage magnitude corresponding to a first intensity of the hot feedback and the fourth power has a voltage magnitude correspond to a second intensity of the cold feedback, and wherein the first intensity is smaller than the second intensity.

When the feedback type information indicates a thermal grill feedback and the feedback intensity information indicates a fourth intensity greater than the third intensity, the controller may apply a fifth power to the one portion of the thermoelectric couple array and a sixth power to another portion of the thermoelectric couple array. A current direction of the fifth power may be the forward direction and a current direction of the sixth power is the reverse direction. The fifth power may have a voltage magnitude greater corresponding to a fifth intensity greater than the first intensity of the hot feedback and the fourth power may have a voltage magnitude correspond to a sixth intensity greater than the second intensity of the cold feedback. The fifth intensity may be smaller than the sixth intensity.

The plurality of the thermoelectric couple groups may form one dimensional array. The thermoelectric couple groups included in the one portion may be disposed on a (2n)-th line of the one-dimensional array and the thermoelectric couple groups included in another portion may be disposed on a (2n+1)-th line of the one-dimensional array, where (n) is a natural number.

The plurality of the thermoelectric couple groups may form two-dimensional array. The thermoelectric couple groups included in the one portion may be separated each other, the thermoelectric couple groups included in another portion may be separated each other and the thermoelectric couple groups included in the one portion and the thermoelectric couple groups included in another portion may be adjacent to each other.

A product of a first ratio and a second ratio may be more than 1.5 and less than 5.0. The first ratio may be a ratio of a temperature drop amount due to the cold feedback having the second intensity to a temperature rise amount due to the hot feedback having the first intensity. The second ratio may be an area ratio of the one portion to another portion.

1. Feedback Device

Hereinafter, a feedback device 100 according to an embodiment of the present disclosure will be described.

The feedback device 100 provides a thermal feedback to a user. In particular, the feedback device 100 may provide thermal feedback that applies heat to the user or absorbs heat from the user, by performing a heat generating operation or a heat absorbing operation.

The feedback device 100 as a device outputting the thermal feedback can be used in a wide range of applications where the thermal feedback can provide a thermal experience associated with a reproduction of a multimedia content such as games, videos, movies, VR/AR applications. The feedback device 100 may cooperate with a content reproduction device (e.g., a game console or a PC), which plays multimedia contents commonly provided in the form of a game and an experience application. According to the development of technology, the feedback device 100 itself may also serve as the content reproduction device for executing multimedia contents.

1.1. Thermal Feedback

The thermal feedback is a kind of thermal stimulation that makes the user feel a thermal sensation by stimulating the thermal sensory organs of the user which are distributed throughout the body of the user. In the present specification, thermal feedback refers to all the thermal stimuli that may stimulate the user's thermal sensory system.

Representative examples of the thermal feedback include a hot feedback and a cold feedback. The hot feedback means the thermal feedback making the user feel a hot sensation by applying a "hot heat" or a positive heat to a hot spot on the user's skin. The cold feedback means the thermal feedback making the user feel a cold sensation by applying a "cold heat" or a negative heat to a cold spot on the user's skin.

Since the heat is a physical quantity represented by a scalar form, the expression, "apply cold heat," or "apply negative heat," may not be an exact expression from a physical point of view. For the convenience of the present description, however, "absorbing heat" may be referred to "applying cold heat" or "transferring cold heat." The term of "negative heat" may be also used instead of "cold heat."

Further, the thermal feedback in the present specification may further include a thermal grill feedback in addition to the hot feedback and the cold feedback. When the hot heat and the cold heat are given at the same time, the user perceives a pain sensation instead of recognizing the hot sensation and the cold sensation individually. This pain sensation is referred to as a so-called thermal grill illusion (TGI). That is, the thermal grill feedback means a thermal feedback which applies a combination of the hot heat and the cold heat, and can be provided by outputting the hot feedback and the cold feedback simultaneously. A more detailed explanation of the thermal grill feedback will be provided below.

1.2. Implementation Example of Feedback Device

The feedback device 100 providing the thermal feedback described above may be implemented in various forms. Hereinafter, some representative implementations of the feedback device 100 will be described.

1.2.1. Gaming Controller

One implementation example of the feedback device 100 is the gaming controller 100a.

Here, the gaming controller 100a may be an input for receiving a user manipulation in a game environment. The gaming controller 100a receives the user manipulation used, e.g., in a videogame and communicates data regarding the user manipulation to a device executing a game program, such as a game console, a computer, a tablet, a smart phone, etc. In the case of a portable game machine, the gaming controller 100a may be integrated into the portable machine itself.

Recently, the game environment has been transformed from the conventional form reflecting the user manipulation on the game screen outputted through the conventional TV or monitor into a virtual reality or an augmented reality using a head mounted display (HMD) such as Oculus's Rift™ or Microsoft's Hololens™ In such new game environments, the gaming controller 100a is expanding its role from a input devise to also function as an output device for providing various feedbacks to the user, so as to increase an immersion feeling of a game. For example, Sony's Dual Shock™ for Playstation™ is equipped with a vibration function that outputs a tactile feedback to the user.

In the present specification, the feedback device 100 implemented in the form of the gaming controller 100a may add a thermal sensation as an interactive element to the game by providing the thermal feedback to the user and induce an enhanced game immersion.

FIGS. 1 to 7 illustrate a gaming controller 100a as implementation examples of the feedback device 100 according to several embodiments of the present disclosure.

The gaming controller 100a may be provided as a controller 100a-1 similar to that shown in FIG. 1 which is held with both hands such as an input for interfacing with Sony's PlayStation™ or Microsoft's Xbox™. The gaming controller 100a may be provided as a bar type 100a-2 similar to that shown in FIG. 2 which is held on one hand such as an input for interfacing with a Nintendo's Wii™.

Figure 3:
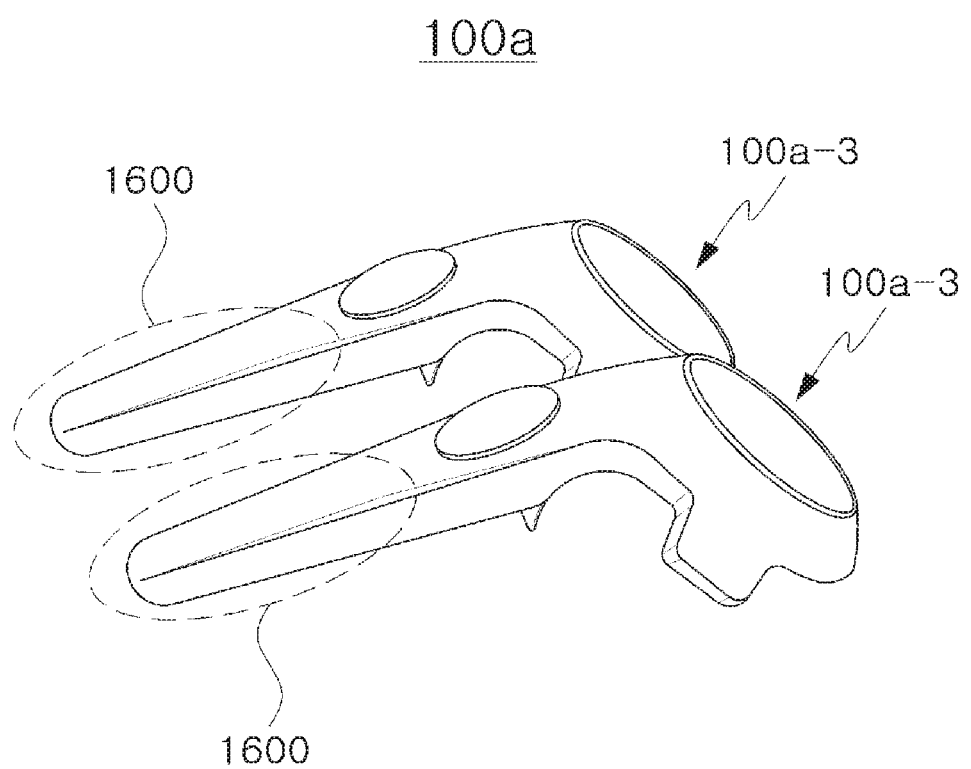
FIG. 3 illustrates another gaming controller as an implementation example of the feedback device according to an embodiment of the present disclosure.

In particular, the gaming controller 100a of the bar type is suitable for receiving user manipulation in the virtual or augmented reality environment, and the gaming controller 100a may be provided as a pair of bar type controllers 100a-3 similar to that shown in FIG. 3, such as the Move Motion™ controller used with Sony's Playstation VR™ game console or the input for the HTC's Vive™ game console wherein one of the bar type controllers is held in each hand.

Figure 4:
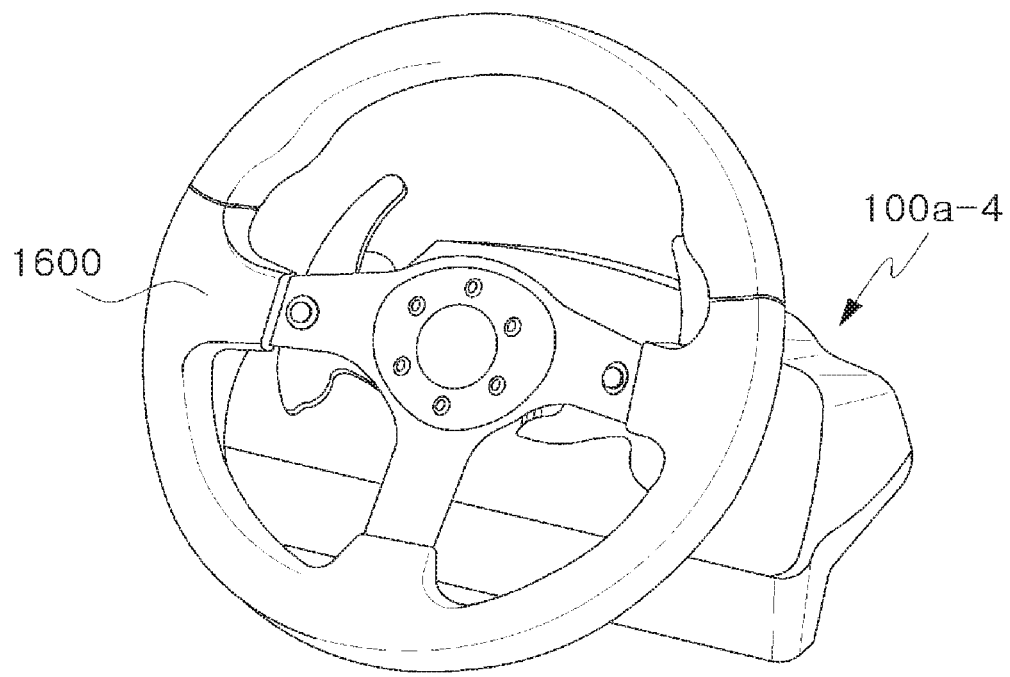
FIG. 4 illustrates another gaming controller as an implementation example of the feedback device according to an embodiment of the present disclosure.
Figure 5:
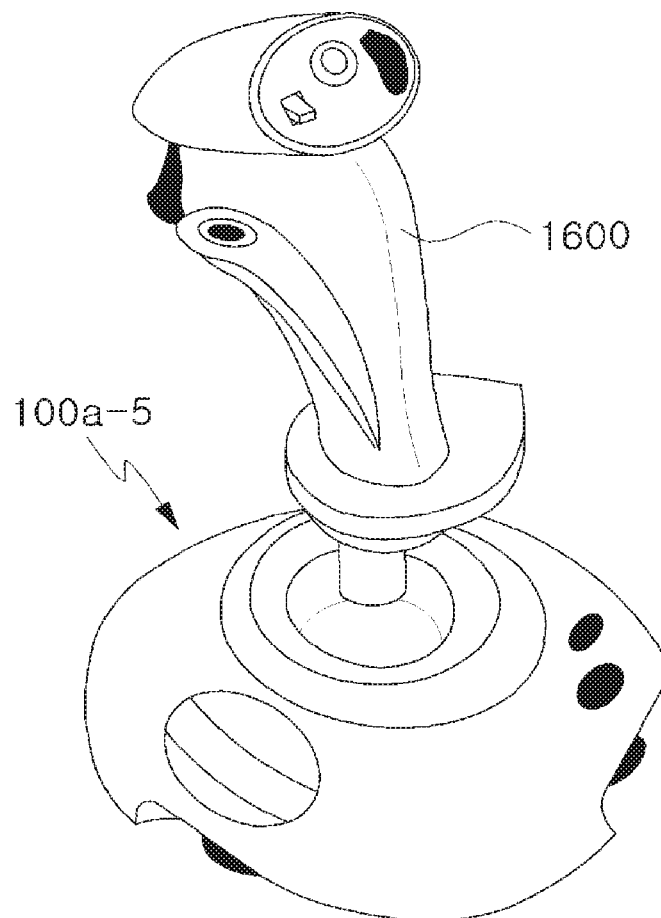
FIG. 5 illustrates another gaming controller as an implementation example of the feedback device according to an embodiment of the present disclosure.
Figure 6:
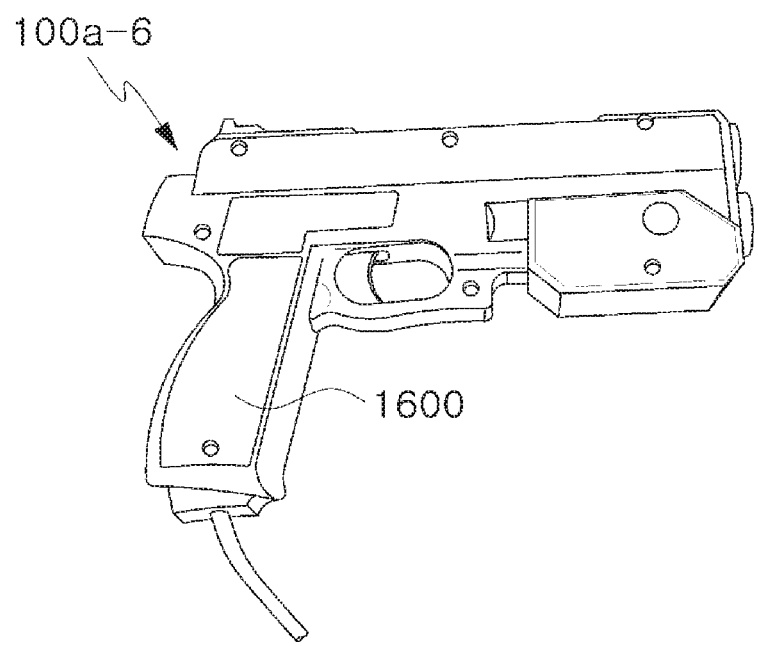
FIG. 6 illustrates another gaming controller as an implementation example of the feedback device according to an embodiment of the present disclosure.
Figure 7:
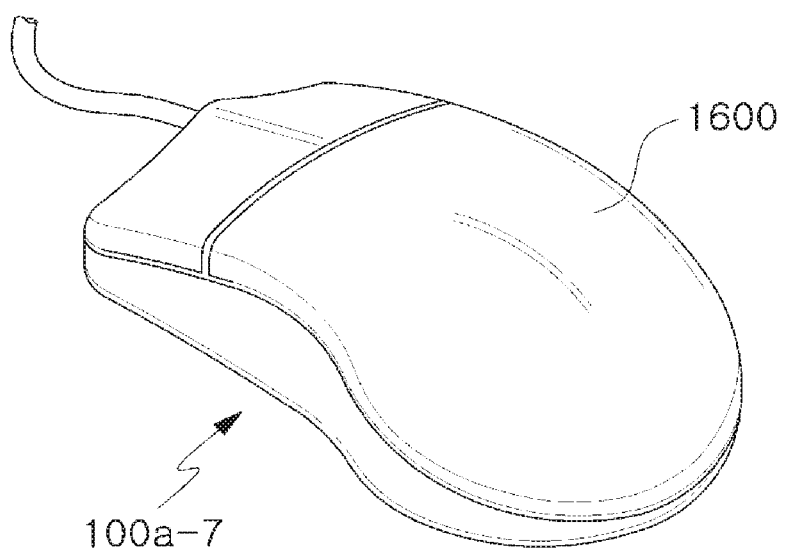
FIG. 7 illustrates another gaming controller as an implementation example of the feedback device according to an embodiment of the present disclosure.

In addition, the gaming controller 100a may include a wheel-type controller 100a-4 similar to that shown in FIG. 4 (used in a racing game), a joystick-type controller 100a-5 similar to that shown in FIG. 5 (used in a flight simulator game), a gun-type controller 100a-6 similar to that shown in FIG. 6 (used in a first-person shooter game) or a mouse type controller 100a-7 similar to that in FIG. 7 (commonly used in computer gaming environments).

The above-described gaming controller 100a may be designed to provide the thermal feedback to the user through a portion in contact with the user's body (e.g., the user's palm surface). Referring to FIGS. 1 to 7, the portion for providing the thermal feedback to the user's body, that is, a contact surface 1600 is shown for each type of the gaming controller 100a. The position of the contact surface 1600 is not limited to the drawings. The contact surface 1600 may be provided in the gaming controller 100a at a portion different from the drawing.

1.2.2. Wearable Device

Another implementation example of the feedback device 100 is as a wearable device 100b.

The wearable device 100b may be a device that is worn on the user's body and performs various functions. As the interest in human machine interface (HMI) increases with the recent trend of pursuing more convenient technology, various wearable devices 100b have been developed. A new user experience can be made possible by utilizing the thermal feedback function in the wearable device 100b.

FIGS. 8 to 14 illustrate wearable devices as implementation examples of the feedback device 100 according to certain embodiments of the present disclosure.

Figure 8:
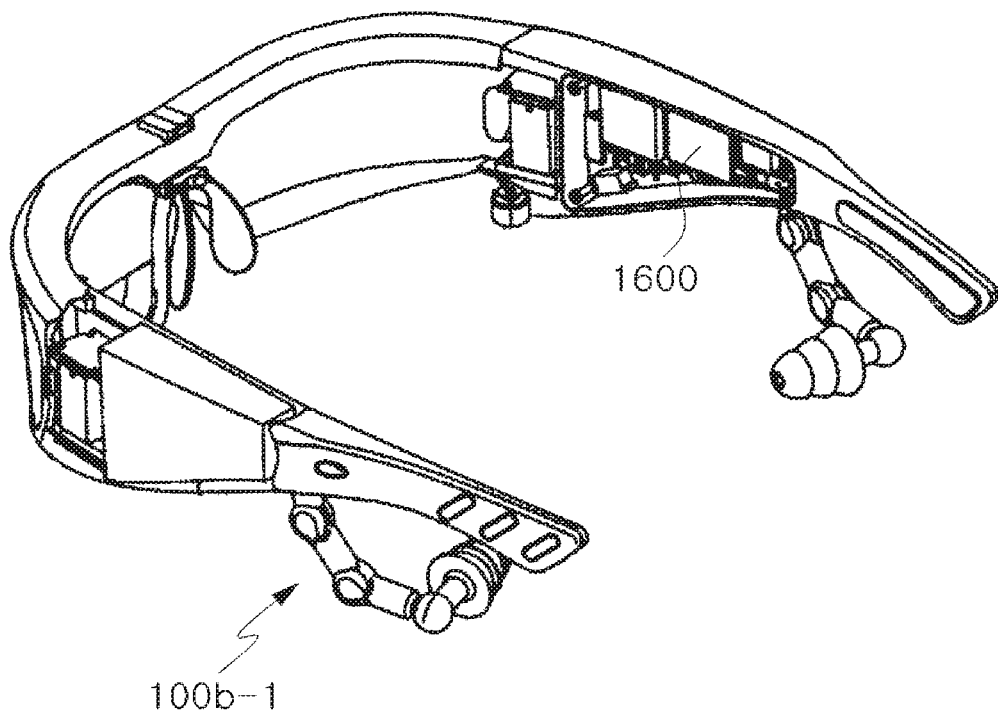
FIG. 8 illustrates a wearable device as an implementation example of the feedback device according to an embodiment of the present disclosure.
Figure 9:
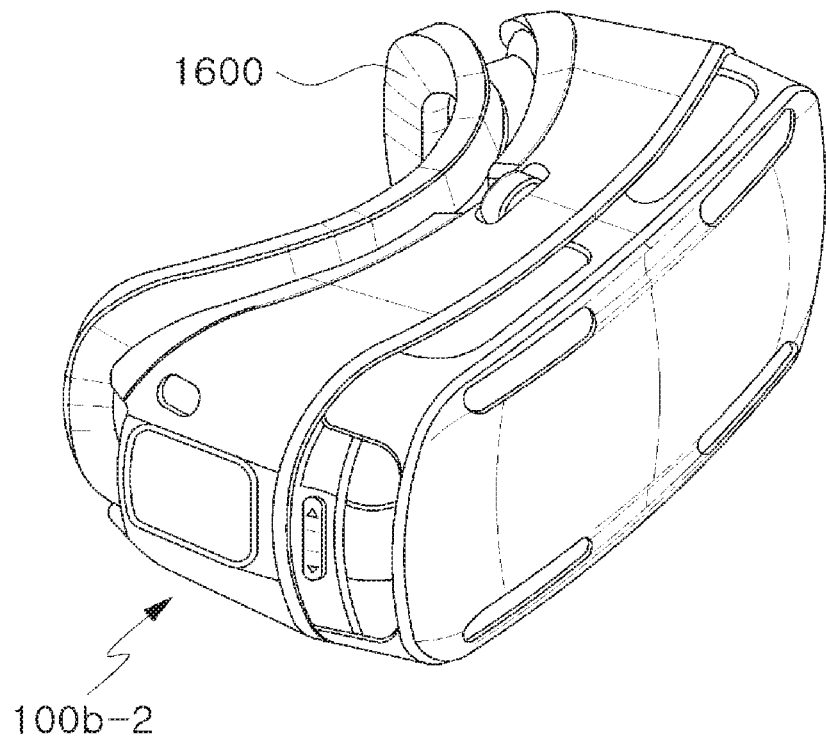
FIG. 9 illustrates another wearable device as an implementation example of the feedback device according to an embodiment of the present disclosure.
Figure 10:
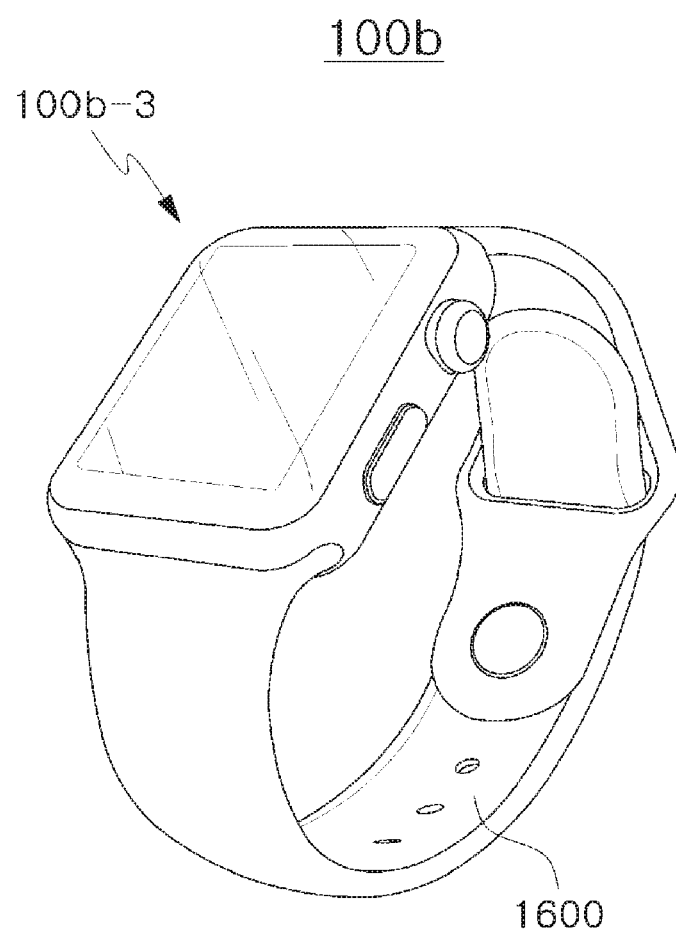
FIG. 10 illustrates another wearable device as an implementation example of the feedback device according to an embodiment of the present disclosure.
Figure 11:
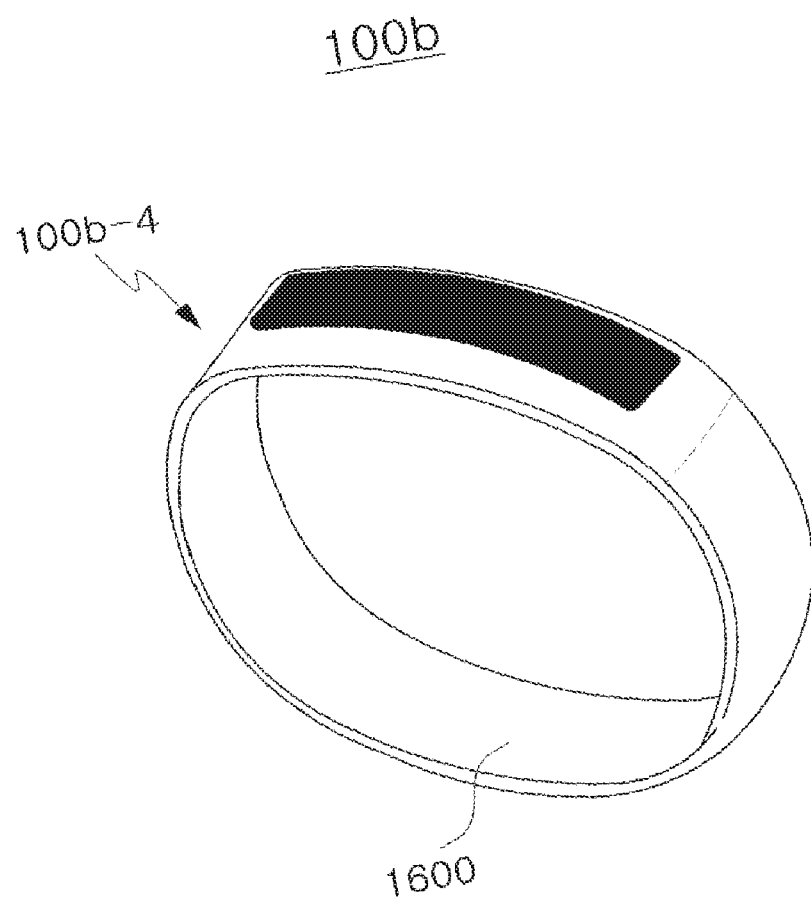
FIG. 11 illustrates another wearable device as an implementation example of the feedback device according to an embodiment of the present disclosure.
Figure 12:
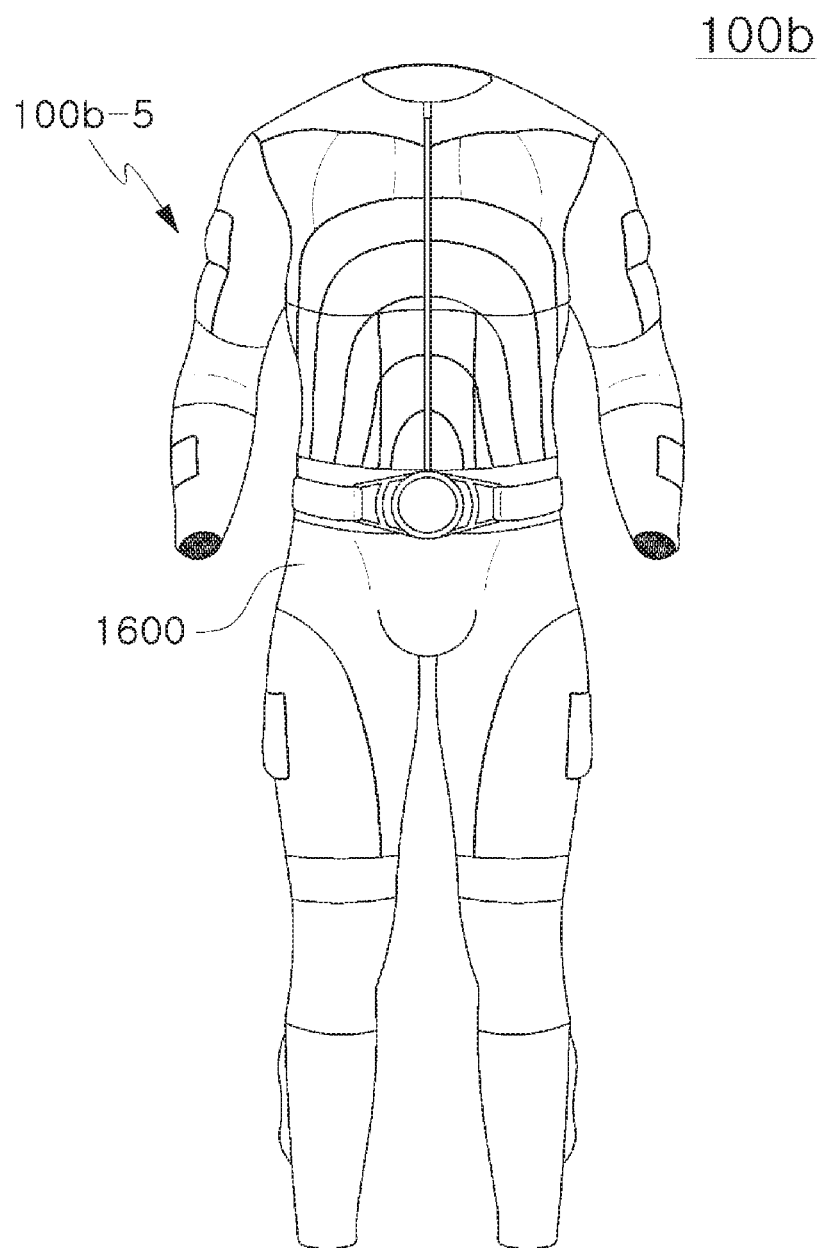
FIG. 12 illustrates another wearable device as an implementation example of the feedback device according to an embodiment of the present disclosure.
Figure 13:
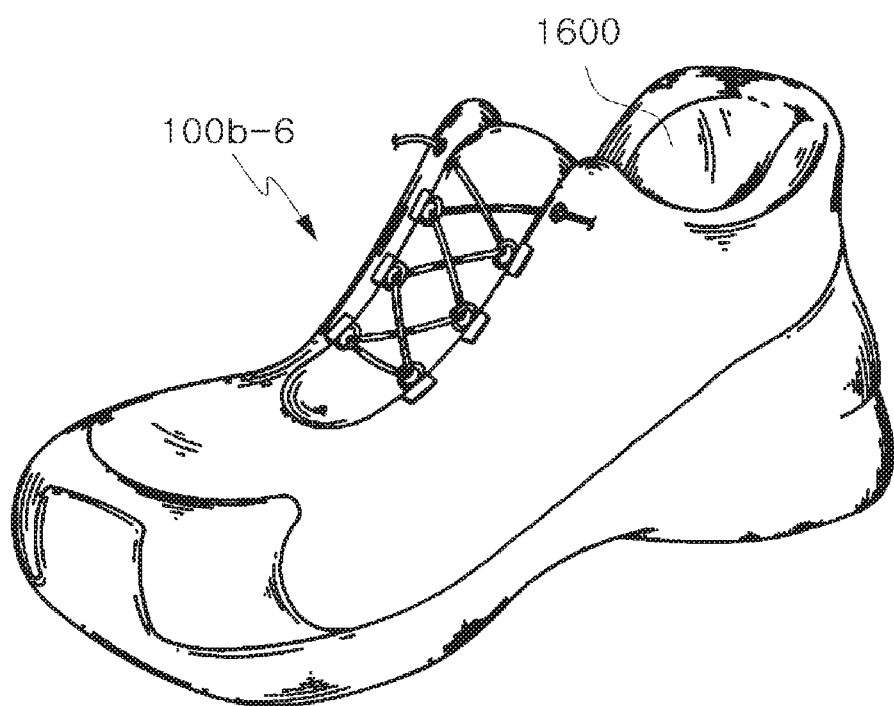
FIG. 13 illustrates another wearable device as an implementation example of the feedback device according to an embodiment of the present disclosure.
Figure 14:
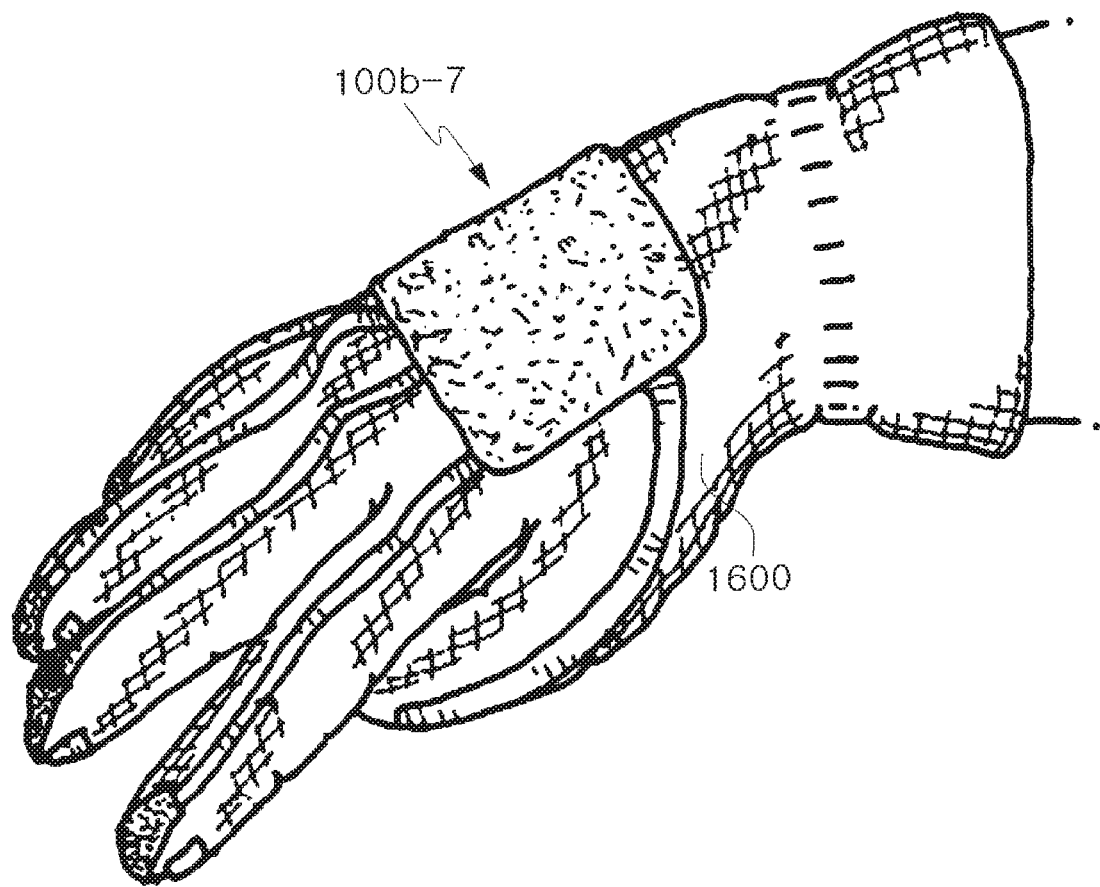
FIG. 14 illustrates another wearable device as an implementation example of the feedback device according to an embodiment of the present disclosure.

The wearable device 100b is being developed in various forms which are mounted or worn on the user's body. The wearable device 100b may be provided as a glasses-type device 100b-1 (to be worn like glasses) as shown in FIG. 8, an HMD-type device 100*b*-2 (to be worn on the head) similar to that shown in FIG. 9, a watch-type device 100*b*-3 or a band-type device 100*b*-4 (to be worn on the wrist) similar to those shown in FIGS. 10 and 11, a suit-type device 100*b*-5 (to be worn like clothes) similar to that shown in FIG. 12, a glove-type device 100*b*-6 similar to that shown in FIG. 13, and a shoe-type device 100*b*-7 (to be worn like a shoe) similar to that shown in FIG. 14.

As with the gaming controller 100*a* described above, the wearable device 100*b* can also be designed to provide the thermal feedback to the user through a portion in contact with the user's body. Referring to FIGS. 8 to 14, the portion for providing the thermal feedback to the user's body, that is, the contact surface 1600, is shown for each type of the wearable device 100*b*. The position of the contact surface 1600 is not limited by the drawings, and the contact surface 1600 may be provided at the wearable device 100*b* in a portion different from the drawing.

Although the gaming controller 100*a* and the wearable device 100*b* have been described above as the implementation examples of the feedback device 100, the implementation examples of the feedback device 100 are not limited thereto.

The feedback device 100 may be substantially implemented with any device in which the thermal feedback function can be usefully utilized. As one example, the feedback device 100 may be applied to a medical device for testing a patient's thermal sensation, or may be provided with a steering wheel of an automobile for providing a moderate heat sensation in the hands of the driver or providing a warning signal to the driver. As another example, the feedback device 100 may be used in an educational facility to provide a thermal sensation to the student to enhance the educational effect or a chair of a movie theater to provide a thermal sensation to the user in addition to the audiovisual sense to enhance the immersion in movies.

1.3. Configuration of Feedback Device

Hereinafter, the configuration of the feedback device 100 according to an embodiment of the present disclosure will be described.

Figure 15:
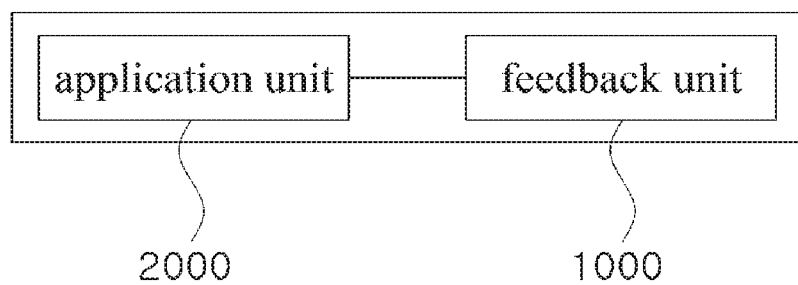
FIG. 15 is a block diagram of the configuration of the feedback device according to an embodiment of the present disclosure.

FIG. 15 is a block diagram of the configuration of the feedback device 100 according to an embodiment of the present disclosure.

Referring to FIG. 15, the feedback device 100 may include an application unit 2000 and a feedback unit 1000. The application unit 2000 is a unit for performing certain functions according to the implementation of the feedback device 100, and the feedback unit 1000 is a unit for outputting the thermal feedback.

The application unit 2000 may be suitably designed according to the implementation of the feedback device 100. For example, in the case of the feedback device 100 in form of the gaming controller 100*a* that cooperates with a game console, the application unit 2000 may include a casing of the gaming controller 100*a*, a communication module for communication with the game console, an input module for receiving a user input, and an application controller for controlling the overall operation of the gaming controller 100*a*. As another example, in the case of the feedback device 100 in form of the wearable device 100*b* of a suit type, the application unit 2000 may include a suit member constituting the suit itself, a sensing module for sensing a user's body signal, and the like.

Alternatively, though the feedback unit 1000 may be somewhat varied in its configuration depending on the implementation, the feedback device 100 may be configured for generating and/or absorbing heat, to control heat generation and/or heat absorption, and to transfer the heat to the user.

Hereinafter, the feedback unit 1000 will be described first, and then the configuration of the application unit 2000 and the manner of interoperation of the application unit 1000 and the feedback unit 2000 in some embodiments of the feedback device 100 will be described.

1.3.1. Feedback Unit

Figure 16:
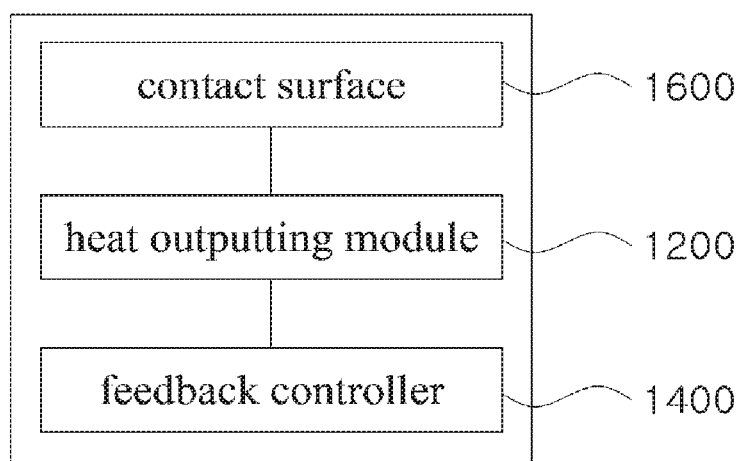
FIG. 16 is a block diagram of the configuration of the feedback unit according to an embodiment of the present disclosure.

FIG. 16 is a block diagram of the configuration of the feedback unit 1000 according to an embodiment of the present disclosure.

Referring to FIG. 16, the feedback unit 1000 may include a heat outputting module 1200, a feedback controller 1400, and a contact surface 1600. The heat outputting module 1200 selectively or simultaneously performs a heat generating operation and a heat absorbing operation under the control of the feedback controller 1400 and transfers a hot heat or a cold heat to the user via the contact surface 1600 so that the feedback device 100 may provide the thermal feedback to the user.

Hereinafter, the detailed configuration of the feedback unit 1000 will be described in more detail.

1.3.1.1. Heat Outputting Module

The heat outputting module 1200 may perform a heat generating operation and/or a heat absorbing operation. The heat outputting module 1200 may use a thermoelectric element such as a Peltier element to perform those operations.

The Peltier effect is a thermoelectric phenomenon discovered by Jean Peltier in 1834. According to the Peltier effect, when an electric current is made to flow through a junction between two conductors a heat generation occurs at the one side of the junction and a heat absorption occurs at the other side of the junction. Peltier elements are elements that produce such a Peltier effect. Peltier elements were initially made of a junction of different metals such as Bismuth and Antimony, but in recent years they have been manufactured by arranging N-P semiconductors between substrates for a higher thermal efficiency.

A Peltier element is capable of generating and absorbing heat on both sides of the element in substantially instantaneous response with application of an electric power, switching between the heat generation and the heat absorption by changing the current direction of the applied power, and adjusting an intensity of the heat generation or absorption precisely by controlling the magnitude of the voltage or the current value of the applied power. A Peltier element is suitable to be used for the heat generating operation or heat absorbing operation for the thermal feedback. In particular, with Assignee's development of the flexible thermoelectric element, it is now possible to manufacture the thermoelectric element in a form that can be easily placed in contact with the user's body, and the possibility of commercial use as the feedback device 100 is increasing.

The heat outputting module 1200 may perform the heat generating operation or the heat absorbing operation as electricity is applied to the thermoelectric element. Although the heat generation and the absorption occur at the same time in the thermoelectric elements that are physically supplied with electric power, in the present specification the heat generating operation and the heat absorbing operation of the heat outputting module 1200 is defined with reference to the contact surface 1600. More specifically, the heat generating operation is an operation that causes heat generation at the contact surface 1600 in contact with the user's body and the heat absorbing operation is an operation that causes heat absorption at the contact surface 1600. For example, the thermoelectric element may be manufactured by disposing an N-P semiconductor on a substrate such that, when an electric power is applied to the thermoelectric element, heat is generated at one side of the thermoelectric element and heat is absorbed at the other side of the thermoelectric element. We may arbitrarily define one side of the thermoelectric element facing the body of the user as the front side, and the opposite side as the rear side. Then an operation that causes the heat generation at the front side and the heat absorption at the rear side is defined as the heat generating operation, and an operation that causes the heat absorption at the front side is defined as the heat absorbing operation.

Since the thermoelectric effect is induced by the electric charge flowing in the thermoelectric element, it is possible to describe the electric energy inducing the heat generating operation or the heat absorbing operation of the heat outputting module 1200 in terms of the electric current. However, in the present description we will describe the electric energy applied to the thermoelectric element mainly in terms of the electric voltage. This is merely for the sake of the convenience of explanation and a person skilled in the arts would understand the operation of the disclosed embodiments in terms of the electric current, based on the voltage-based description. The present disclosure is therefore not limited to expression in terms of the voltage.

As described above, the heat outputting module 1200 may be implemented in various forms which include the thermoelectric element. Therefore, a more detailed description of the configuration of the heat outputting module 1200 will be described later. For example, heat outputting module 1200 may be two unique semiconductors, one n-type and one p-type, that may have different electron densities. Semiconductors in heat outputting module 1200 may be placed thermally in parallel to each other and electrically in series and then joined with a thermally conducting plate on each side. When a voltage is applied to the free ends of the two semiconductors in heat outputting module 1200 there may be a flow of DC current across the junction of the semiconductors causing a temperature difference. The side with the cooling plate absorbs heat which is then moved to the other side of the device where the heat sink is located. Thermoelectric couples are typically connected side by side and sandwiched between two ceramic plates. The cooling ability of the total unit is then proportional to the number of thermoelectric couples in it. Alternatively, or additionally, heat outputting module 1200 may include composed semiconductors, such as GaAr, and operate under nonlinear Peltier effect.

1.3.1.2. Feedback Controller

The feedback controller 1400 may control the overall operation of the feedback unit 1000. For example, the feedback controller 1400 may control the heat outputting module 1200 to perform the heat generating operation or the heat absorbing operation by applying electric energy to the thermoelectric element of the heat outputting module 1200. The feedback controller 1400 may also perform signal processing between the application unit 2000 and the feedback unit 1000.

To this end, the feedback controller 1400 performs calculations and processing of various information and controls an operation of the heat outputting module 1200 by outputting an electric signal to the heat outputting module according to the result of calculations and processing. Thus, the feedback controller 1400 may be implemented in a computer or similar hardware, software or combination thereof. The feedback controller 1400 may be provided in the form of an electronic circuit that performs a control function by processing an electrical signal. The feedback controller 1400 may alternatively be provided in the form of a program or a code for driving a microprocessor or other hardware circuit. In the following description, it can be interpreted that the operation of the feedback unit 1000 is performed by the control of the feedback controller 1400 unless otherwise specified.

1.3.1.3. Contact Surface

The contact surface 1600 directly contacts the user's body and transfers hot heat or cold heat generated by the heat outputting module 1200 to the skin of the user. Thus, the portion of the outer surface of the feedback device 100 that directly contacts the user's body may be the contact surface 1600. For example, regarding the gaming controller 100a shown in FIG. 1, a portion held by the user with both hands may be the contact surface 1600. As another example, a portion of or the entire inside surface of the suit wearable device shown in FIG. 12, may be the contact surface 1600.

In one example, the contact surface 1600 may be provided as a layer that is directly or indirectly attached to the outer surface of the heat outputting module 1200 which faces the user's body. The contact surface 1600 may be disposed between the heat outputting module 1200 and the user's skin and transfer heat between the heat outputting module 1200 and the user. For this purpose, the contact surface 1600 may be provided with a material of high thermal conductivity so that the heat transfer from the heat outputting module 1200 to the user's body is performed efficiently. The layer-type contact surface 1600 also prevents direct exposure of the heat outputting module 1200 to the outside, thereby protecting the heat outputting module 1200 from external impact.

Here, the contact surface 1600 of the layer type may have a larger area than the outer surface of the heat outputting module 1200 to secure a wider surface for the heat transfer in view of the area. For example, the contact surface 1600 may be the inner surface of the suit, even though the heat outputting module 1200 is located at some specific point in the suit-type feedback device 100.

Although the contact surface 1600 is disposed on the heat outputting module 1200 in the above description, the outer surface of the heat outputting module 1200 may itself be the contact surface 1600. Specifically, a part or all the front surface of the heat outputting module 1200 may be the contact surface 1600. In the above description, the contact surface 1600 of the feedback unit 1000 is not included in the heat outputting module 1200, but the contact surface 1600 may alternatively be configured as a component or element included in the heat outputting module 1200.

1.3.1.4. Configuration and Type of Heat Outputting Module

In the above description, it is noted that the heat outputting module 1200 may perform the heat generating operation or the heat absorbing operation using the thermoelectric element. Hereinafter, the configuration and the form of the heat outputting module 1200 will be described in more detail.

First, the configuration of the heat outputting module 1200 will be described.

The heat outputting module 1200 may include a substrate 1220, a thermoelectric element provided as a thermoelectric couple array 1240 which is disposed between the substrate 1220 and a power terminal 1260 for supplying an electric power to the thermoelectric element.

The substrate 1220 serves to support a thermoelectric couple unit 1241 and may be provided as an insulating material. For example, ceramics may be selected as the material of the substrate 1220. The substrate 1220 may be of a flat plate shape. Alternatively, the substrate may have another shape, e.g., to fit the form of the body part intended to receive the thermal feedback.

The substrate 1220 may be provided with a flexible material so it may be universally used for various types of feedback devices 100 of which the contact surfaces 1600 may be of various shapes. For example, the feedback device 100 of the gaming controller 100a type may have a grip section having a curved surface where the user grasps with the palm of the hands for holding the gaming controller 100a, and it may be important that the heat outputting module 1200 is flexible for using the heat outputting module 1200 with a curved user surface. Examples of the flexible material used for the substrate 1220 include glass fiber and flexible plastic.

The thermoelectric couple array 1240 is composed of a plurality of thermoelectric couple units 1241 disposed on the substrate 1220. Semiconductor pairs of N-type and P-type may be used as the thermoelectric couple unit 1241. Alternatively, the thermoelectric couple unit 1241 may be implemented using different pairs of metals (for example, Bismuth and Antimony).

Semiconductor pairs of the thermoelectric couple unit 1241 are electrically connected to each other at one end and electrically connected to semiconductor pairs of the adjacent thermoelectric couple unit 1241 at the other end. The electrical connection of the semiconductor pairs is made by a conductor member 1242 disposed on the substrate 1220. The conductor member 1242 may be a lead or an electrode such as copper or silver.

The electrical connection of the thermoelectric couple unit 1241 may be a serial connection. The thermoelectric couple units 1241 connected in series may form a thermoelectric couple group 1244, and at least one thermoelectric couple group 1244 may form a thermoelectric couple array 1240.

The power terminal 1260 may supply electric energy to the heat outputting module 1200. The thermoelectric couple array 1240 may generate heat or absorb heat according to the applied power and a current direction of the electric power applied to the power terminal 1260. Specifically, each thermoelectric couple group 1244 may be connected to two power terminals 1260. When the heat outputting module 1200 comprises a plurality of thermoelectric couple groups 1244, two power terminals 1260 may be arranged for each thermoelectric couple group 1244. When connected in this manner, the power value or the current direction may be individually controlled for each thermoelectric couple group 1244, so as to control whether to perform the heat generating operation or the heat absorbing operation, and the intensity of the heat generation and the heat absorption.

As will be described later, the power terminal 1260 receives the electrical signal output by the feedback controller 1400, such that the feedback controller 1400 may control the heat outputting module 1200 to perform the heat generating operation and the heat absorbing operation by adjusting the current direction or power magnitude of the electrical signal. When the heat outputting module 1200 includes a plurality of the thermoelectric couple groups 1244, the feedback controller 1400 may be configured to control each thermoelectric couple groups 1244 individually by controlling the electric signals applied to the power terminals 1260 separately.

Some exemplary arrangement of the heat outputting module 1200 will be described based on the above description of the configuration of the heat outputting module 1200.

Figure 17:
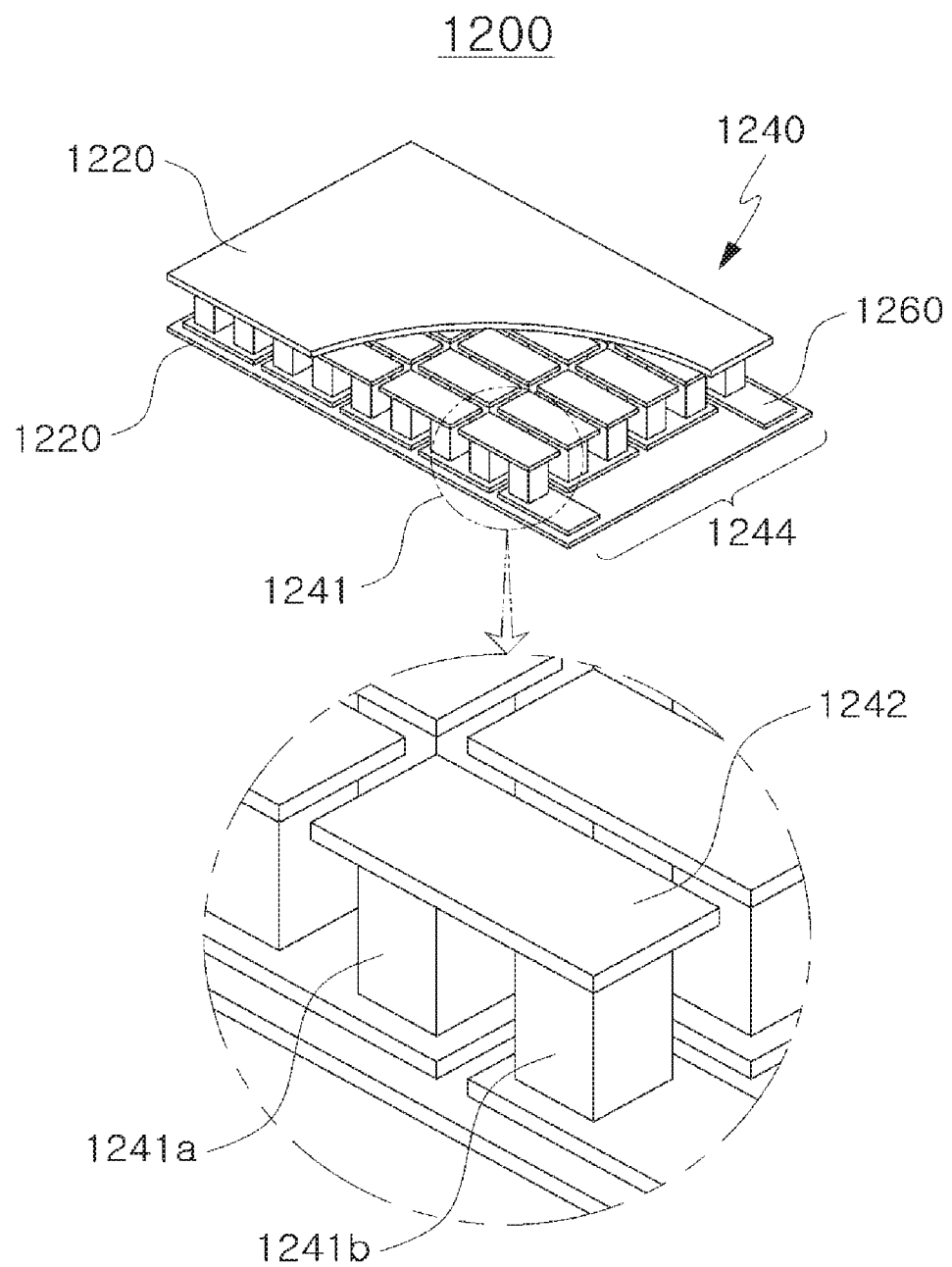
FIG. 17 illustrates an arrangement of a heat outputting module according to an embodiment of the present disclosure.

FIG. 17 illustrates an arrangement of a heat outputting module 1200 according to an embodiment of the present disclosure.

Referring to FIG. 17, one form of the heat outputting module 1200 may include a pair of substrates 1220 facing each other. The contact surface 1600 is located on the outside of one substrate 1220 so that the heat generated by the heat outputting module 1200 can be transferred to the user's body. If the substrate 1220 is flexible, the heat outputting module 1200 may also be flexible.

A plurality of the thermoelectric couple units 1241 are placed between the substrates 1220. Each thermoelectric couple unit 1241 may be composed of a semiconductor pair of an N-type semiconductor 1241a and a P-type semiconductor 1241b. In each thermoelectric couple unit 1241, the N-type semiconductor and the P-type semiconductor are electrically connected to each other by a conductor member 1242 at one end. The N-type semiconductor and the P-type semiconductor of the thermoelectric couple are electrically connected to the P-type semiconductor and the N-type semiconductor of the adjacent thermoelectric couple respectively by the conductor member 1242 at the other ends. The electrical connection between the thermoelectric couple unit 1241 is thus achieved, and the thermoelectric couple units 1241 that are connected in series may form the thermoelectric couple group 1244. In this embodiment, since all the thermoelectric couple units 1241 between the power terminals 1260 are connected in series and the entire thermoelectric couple array 1240 includes one thermoelectric couple group 1244, the heat outputting module 1200 performs the same operation over the entire area of its front surface. That is, when the power is applied to the power terminal 1260 in one direction, the heat outputting module 1200 performs the heat generating operation, and when the power is applied in the opposite direction, the heat outputting module 1200 performs the heat absorbing operation.

Figure 18:
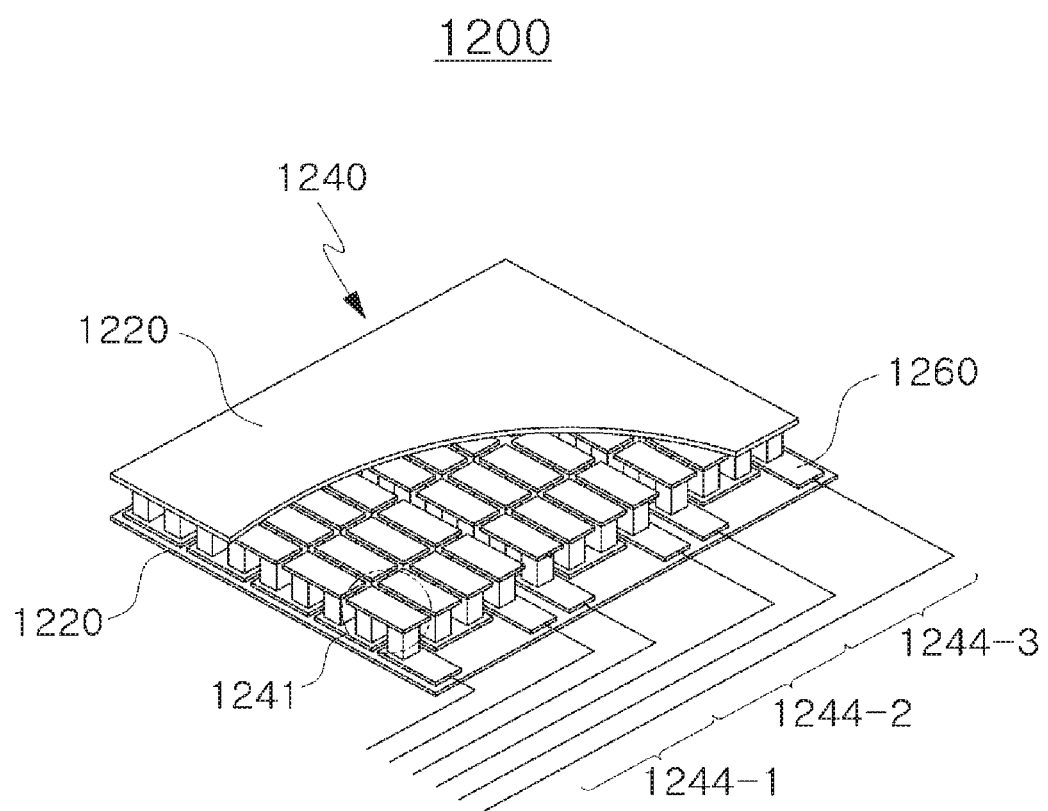
FIG. 18 illustrates another arrangement of the heat outputting module according to an embodiment of the present disclosure.

FIG. 18 illustrates another arrangement of the heat outputting module 1200 according to an embodiment of the present disclosure.

Referring to FIG. 18, another form of the heat outputting module 1200 is similar to the one described above. However, the thermoelectric couple array 1240 of this embodiment has a plurality of thermoelectric couple groups 1244. Each of the thermoelectric couple groups 1244 is connected to the power terminals 1260 respectively and may be controlled separately.

For one example, in FIG. 18, an electric power of different current directions may be applied to a first thermoelectric couple group 1244-1 and a second thermoelectric couple group 1244-2 so that the first thermoelectric couple group 1244-1 may perform the heat generating operation and the second thermoelectric couple group 1244-2 may perform the heat absorbing operation.

Hereinafter, the current direction for the heat generating operation is referred to as "forward direction" and the current direction for the heat absorbing operation is referred to as "reverse direction."

As another example, an electric power of different voltage magnitudes may be applied to the power terminal 1260 of the first thermoelectric couple group 1244-1 and the power terminal 1260 of the second thermoelectric couple group 1244-2 so that the first thermoelectric couple group 1244-1 and the second thermoelectric couple group 1244-2 may perform the heat generating or absorbing operation of different intensity from each other.

Figure 19:
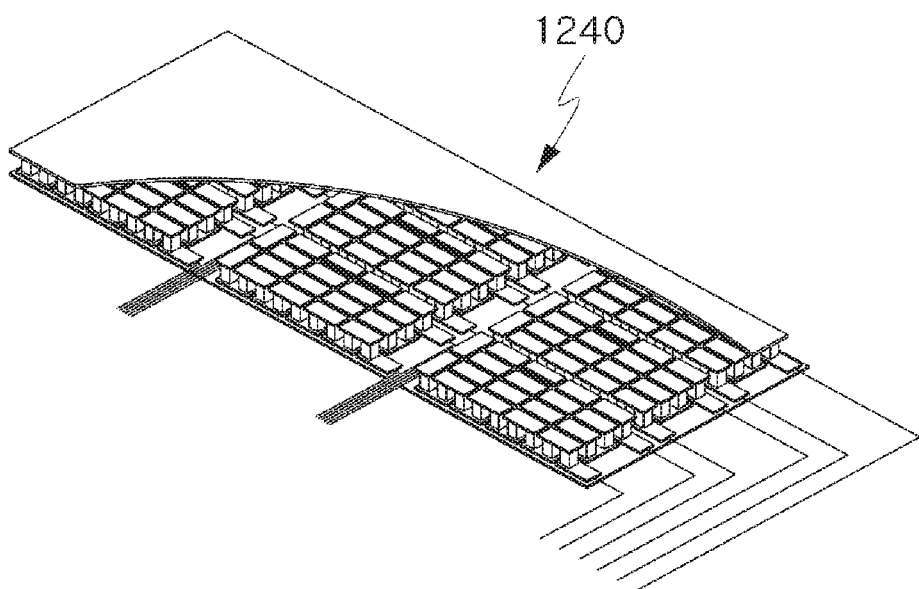
FIG. 19 illustrates another arrangement of the heat outputting module according to an embodiment of the present disclosure.

FIG. 19 illustrates yet another arrangement of the heat outputting module 1200 according to an embodiment of the present disclosure.

Referring to FIG. 18, in the thermoelectric couple array 1240 the thermoelectric couple groups 1244 are arranged one-dimensionally. However, the thermoelectric couple groups 1244 may be arranged two-dimensionally. Referring to FIG. 19, the operation for more finely divided region may be controlled using the thermoelectric couple groups 1244 arranged in a two-dimensional array, In the above-described embodiments, the heat outputting module 1200 is made by a pair of opposing substrates 1220. The heat outputting module 1200 may alternatively be made by a single substrate 1220.

Figure 20:
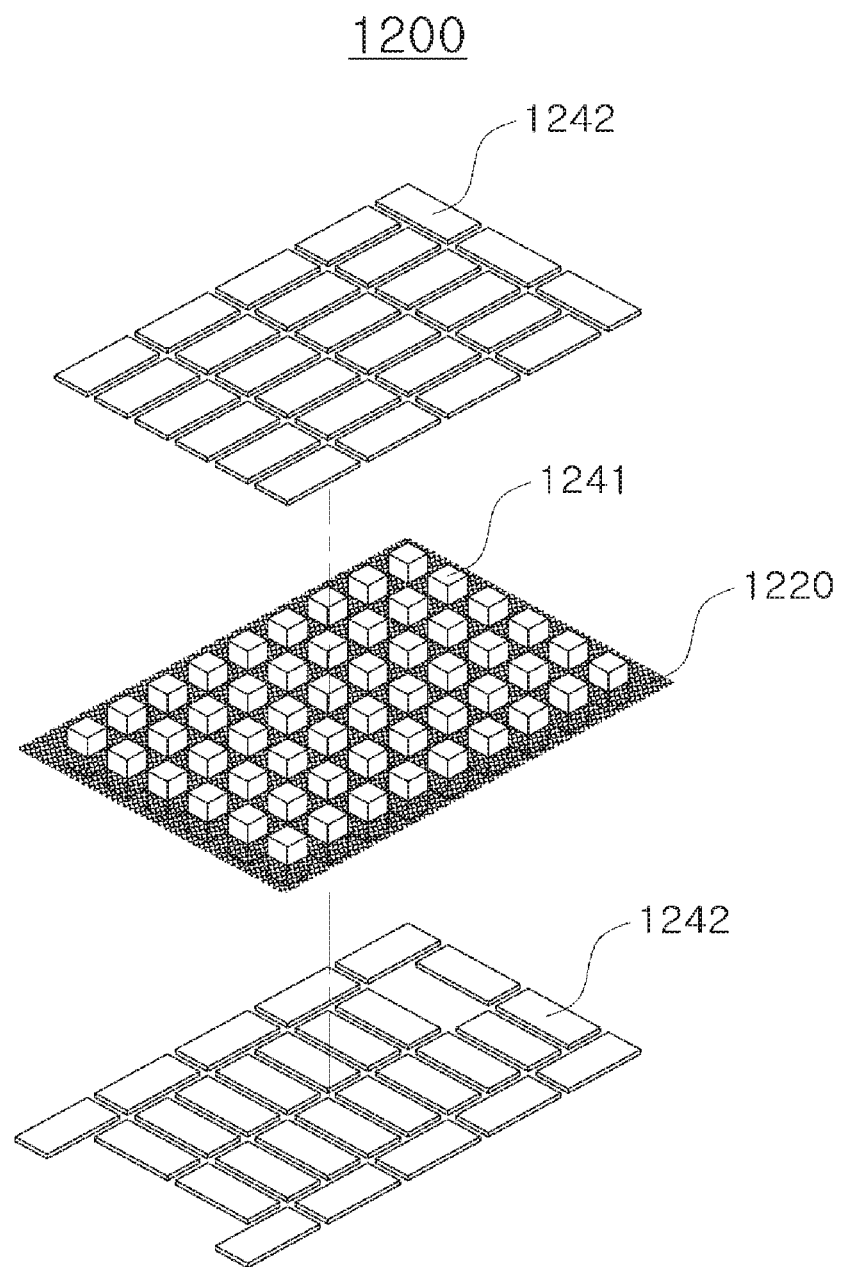
FIG. 20 illustrates another arrangement of the heat outputting module according to an embodiment of the present disclosure.

FIG. 20 illustrates still another arrangement of the heat outputting module 1200 according to an embodiment of the present disclosure.

Referring to FIG. 20, the thermoelectric couple unit 1241 and the conductor member 1242 may be disposed on the single substrate 1220 in a manner that the thermoelectric couple unit 1241 and the conductor member 1242 are attached to the single substrate 1220. Here, the single substrate 1220 may be made of a glass fiber or the like. By using the single substrate 1220 of this type, the heat outputting module 1200 may be made more flexible. Alternatively, the thermoelectric couple unit 1241 and the conductor member 1242 may be buried in a pore, gap or the like in the substrate by using a porous substrate as the single substrate 1220. In some embodiments, a urethane layer may be used as the single substrate 1220. In other embodiments, alternative forming agents or organic polymers may be used as the single substrate 1220. For example, the single substrate 1220 may include polyurethanes such as polyester and polyether.

Various aspects of the heat outputting module 1200 described above can be combined or modified within a range that is obvious to a person skilled in the art. For example, in some embodiments of the heat outputting module 1200 the contact surface 1600 which is formed on the front surface of the heat outputting module 1200 may be formed as a separate layer from the heat outputting module 1200. However, the front surface of the heat outputting module 1200 itself may be the contact surface 1600. That is, in an embodiment of the heat outputting module 1200 described above, the outer surface of one substrate 1220 may be the contact surface 1600.

1.3.2. Application Unit

The application unit 2000 of the feedback device 100 will be described below. As described above, the application unit 2000 may be designed in various forms suitable for performing its own functions according to the implementation of the feedback device 100. The feedback device 100 of the present disclosure can be provided in any form for utilizing the thermal feedback effectively, and thus it is practically impossible to describe the application unit 2000 for all implementations of the feedback device 100. Therefore, the application unit 2000 will be described with reference to the application unit 2000 of the gaming controller 100a type.

Figure 21:
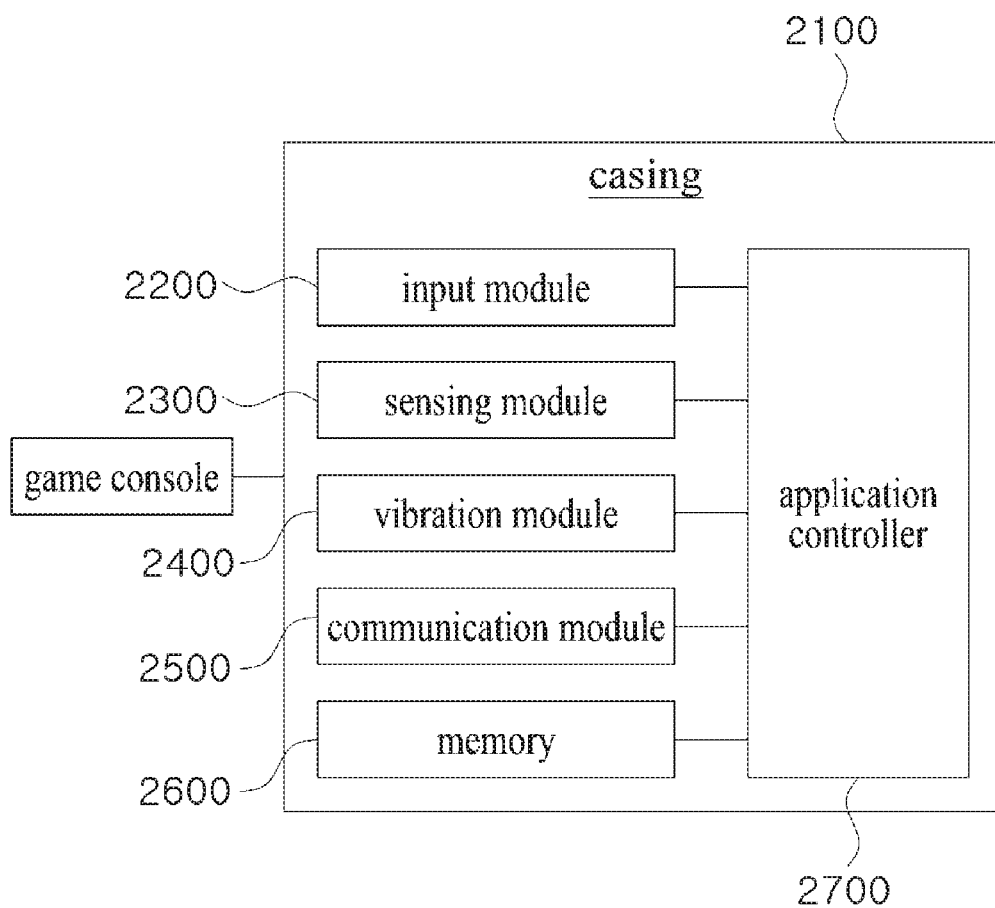
FIG. 21 is a block diagram of the configuration of an application unit according to an embodiment of the present disclosure
Figure 22:
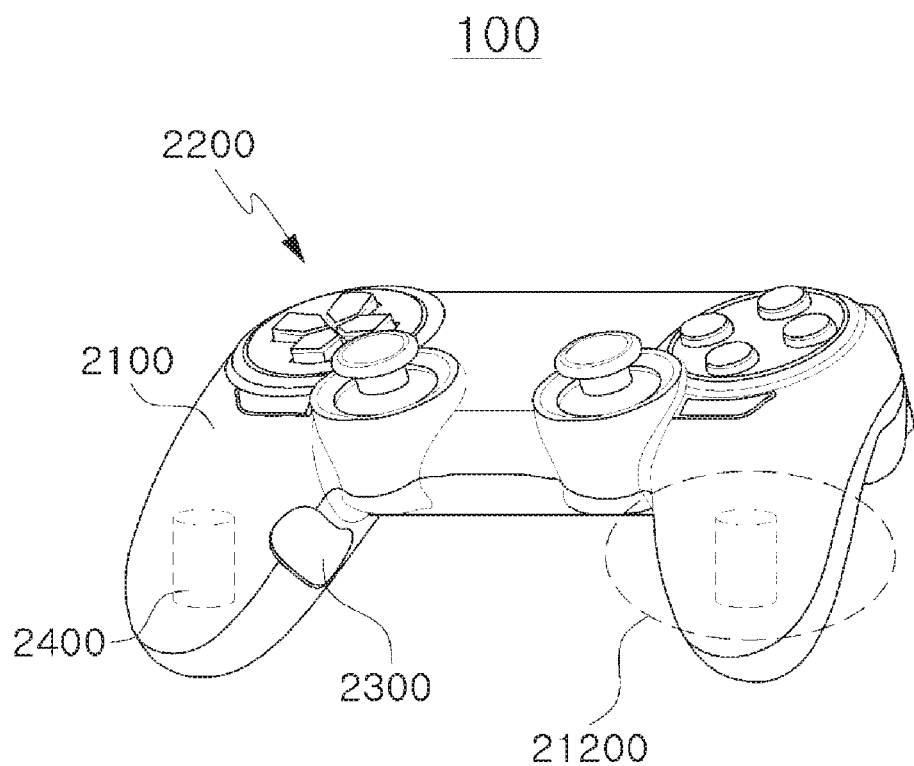
FIG. 22 is a schematic diagram of the configuration of the application unit according to an embodiment of the present disclosure.

FIG. 21 is a block diagram of the configuration of an application unit 2000 according to an embodiment of the present disclosure, and FIG. 22 is a schematic diagram of the configuration of the application unit 2000 according to an embodiment of the present disclosure.

FIGS. 21 and 22, the application unit 2000 includes a casing 2100, an input module 2200, a sensing module 2300, a vibration module 2400, a communication module 2500, a memory 2600, and an application controller 2700.

The casing 2100 forms an exterior of the feedback device 100 of the gaming controller type and may accommodate the elements such as the communication module 2500 or the application controller 2700 therein. The elements thus accommodated can be protected from external shock or the like by the casing 2100.

The overall shape of the casing 2100 may be, e.g., a pad type for both hands or a bar type for one hand, but is not limited thereto. For reference, the two-hand pad type is typically used for traditional games based on 2D displays, and the bar type is used for games of the virtual reality, augmented reality, and mixed reality (MR).

The casing 2100 may be provided with a grip portion 2120 for user to grip the feedback device 100. The grip portion 2120 may be made of a material having a high frictional coefficient (for example, rubber or Urethane) or may have a non-slippery shape (for example, a concavo-convex shape or the like). Also, the grip portion 2120 may be made of a material that absorbs perspiration from the user's skin.

Here, the contact surface 1600 of the feedback unit 1000 may be formed in the grip portion 2120, or the grip portion 2120 itself may be the contact surface 1600. There may be two grip portions 2120 in the gaming controller 100a of the two-hand pad type. There may be one grip portion 2120 in the gaming controller 100a of the single hand bar type. In this case, the gaming controllers 100a of the bar type may be used in pairs and each of the gaming controllers 100a of the bar type may have the grip portion 2120, respectively.

The input module 2200 may obtain user input from a user. In the gaming controller 100a, the user input is typically a user command for games, such as character manipulation or menu selection in the game. For example, the input module 2200 may be include a button or joystick, and the user may input the user input by pressing the button or manipulating the joystick in a specific direction. The input module 2200 is not limited to the above-described examples.

The sensing module 2300 may sense various information related to the gaming controller 100a. Examples of a sensing module 2300 include an orientation sensor for sensing the orientation of the gaming controller 100a and a motion sensor for sensing the motion of the gaming controller 100a. In addition, the sensing module 2300 may be a biosensor for sensing a bio-signal of the user. A gyro sensor or an acceleration sensor may be used as the orientation sensor or the motion sensor. The biosensor may include a temperature sensor for sensing the user's body temperature or an electrocardiogram sensor for sensing an electrocardiogram of the user.

The vibration module 2400 may output a vibration feedback. The vibration feedback may further enhance user engagement with the game along with the thermal feedback. For example, the vibration feedback may occur when a character in the game is caught in an explosion scene or when a player gets shocked by falling from a high altitude. On the other hand, as will be described later, the vibration feedback and the thermal feedback may be interlocked with each other.

The communication module 2500 may perform communication with external devices. In some embodiments, the gaming controller 100a may be provided as a standalone type device. However, the gaming controller 100a may be provided as a device operating in conjunction with an electronic device that executes a game program such as a game console or a PC. The electronic device executing a game may include a game console, a portable game console, a PC, a smart phone, a tablet, or the like. Hereinafter, these will be collectively referred to as "game consoles." Accordingly, the gaming controller 100*a* may transmit/receive various information to/from a game console through the communication module 2500.

The communication module 2500 may be a wired type or a wireless type.

Since the wired type and the wireless type have their own advantages and disadvantages, the wired type and the wireless type may be provided simultaneously in one gaming controller 100*a*.

An example of the communication module 2500 of the wired type is a USB (Universal Serial Bus) communication, but other communication protocols may also be used. In the case of the wireless type. A wireless personal area network (WPAN) communication such as Bluetooth or Zigbee may be used. However, the wireless communication protocol is not limited to the example describe-above and the communication module 2500 of the wireless type may use a WLAN (Wireless Local Area Network) communication such as Wi-Fi, Wi-Fi Direct, or other known communication protocols. Any communication protocol developed by the game manufacturer may also be used as the wired or wireless communication protocol.

The memory 2600 may store various kinds of information. The memory 2600 may store data temporarily or semi-permanently. Examples of the memory 2600 include a hard disk drive (HDD), a solid-state drive (SSD), a flash memory, a ROM (Read-Only Memory) and a RAM (Random Access Memory). The memory 2600 may be provided in a form embedded in the feedback device 100 or in a detachable form in the feedback device 100.

The memory 2600 may store an operating system (OS) for driving the feedback device 100 or various data for the operation of the feedback device 100.

The application controller 2700 may perform control of the application unit 2000 and overall control of the feedback device 100. For example, the application controller 2700 may transmit the user input inputted via the input module 2200 or the orientation information of the gaming controller 100*a* sensed by the sensing module 2300 to the game console using the communication module 2500. As another example, the application controller 2700 may receive a vibration signal from the game console via the communication module 2500 and cause the vibration module 2400 to output the vibration feedback. The application controller 2700 receives the thermal feedback request signal from the game console through the communication module 2500 and transmits the thermal feedback request signal to the feedback controller 1400 so that the feedback controller 1400 controls the heat outputting module 1200 to output the thermal feedback.

In some embodiments, the feedback request message may be sent in a packet structured according to wired or wireless communications protocol (e.g., USB, Wi-Fi, etc.) employed by the system. In other embodiments, the feedback request message may be communicated with analog or digital modulated signals. For example, the feedback request may include voltage signals with one or more amplitudes or frequencies that encode the feedback request message. In yet other embodiments, the feedback request may take the form of an internet protocol message (e.g., TCP/IP), a query packet, or a port opening instruction. In such embodiments, the feedback request message may include a checksum or other field used to validate information transmitted in the feedback request message. The feedback request message may include information of application controller 2700, feedback controller 1400 and/or outputting module 1200 such as a name, feedback intensity, and/or identification number. Additionally, the feedback request message may specify cells in thermocouple array 1240 or power deliveries for thermocouple array 1240.

The control operation described above may be performed as the application controller 2700 performs calculation and processing of various information. To this end, the application controller 2700 may be implemented using hardware, software or a combination thereof. Thus, the application controller 2700 may be implemented as a computer or similar device. The application controller 2700 may be provided in the form of an electronic circuit that processes an electrical signal to perform a control function. The application controller 2700 may alternatively be provided in the form of a program or a code for driving a microprocessor or other hardware circuit.

The application controller 2700 of the application unit 2000 and the feedback controller 1400 of the feedback unit 1000 may be physically separated or may be provided in a single physical configuration. In other words, the application controller 2700 and the feedback controller 1400 may be manufactured on separate chips and may cooperate through communication interfaces between the two, but may alternatively be included in a single chip which performs functions of both of the application controller 2700 and the feedback controller 1400. Hereinafter, to facilitate explanations, the application controller 2700 and the feedback controller 1400 will be described as being functionally separated, with the understanding that the present disclosure is not limited thereto.

As described above, the feedback device 100 may be implemented in various forms other than the gaming controller 100*a* explained above. Thus, some or all the contents described related with the gaming controller 100*a* may be applied to the other types of the feedback device 100 different from the gaming controller 100*a*. In addition, the gaming controller 100*a* is not necessarily used only for a game, and may be used for a variety of purposes including an experience application using a virtual reality technique or an augmented reality technique, an educational application, a medical application, and the like.

2. Operation of Feedback Device

Hereinafter, the operation of the feedback device 100 will be described.

The feedback device 100 may provide the thermal feedback. The thermal feedback may include a hot feedback, a cold feedback, and a thermal grill feedback. The feedback device 100 may provide the thermal feedback described above by the feedback unit 1000 performing a heat generating operation or a heat absorbing operation selectively or simultaneously.

The feedback device 100 may also provide the thermal feedback of various levels of intensity. The intensity of the thermal feedback may be adjusted such that the feedback controller 1400 of the feedback unit 1000 adjusts the magnitude of the electric power applied to the heat outputting module 1200.

The feedback device 100 may also perform an operation to prevent thermal damage to the user's skin that receives heat through the contact surface 1600 when the thermal feedback is provided. The damage protection function may be accomplished by adjusting or limiting the intensity or duration time of the thermal feedback. The intensity or duration time of the thermal feedback may be adjusted or limited by controlling the electrical signal applied to the heat outputting module 1200.

The feedback device 100 may also perform an operation to remove a thermal inversion illusion. The thermal inversion illusion is an illusionary sensation that is opposite to the pre-applied thermal feedback and felt by a user when the pre-applied thermal feedback is terminated. The feedback device 100 may eliminate the thermal inversion illusion by performing a buffering operation at the end of the thermal feedback.

The feedback device 100 may also perform a heat moving operation in which the thermal feedback is moved. The heat moving operation may mean providing the user with a sense of a moving heat on contact surface 1600 using a thermoelectric element provided as the thermoelectric couple array 1240 comprised of a plurality of individually controllable thermoelectric couple groups 1244.

The various operations of the above-described feedback device 100 will now be described in more detail.

2.1. Operation for Providing Thermal Feedback

Hereinafter, the operation of providing the thermal feedback by the above-described feedback unit 1000 will be described. The thermal feedback provided by the feedback unit 1000 includes a heat generating operation to provide a hot sensation to the user and a heat absorbing operation to provide a cold sensation. The feedback unit 1000 may also perform a thermal grill operation for giving the thermal grill feedback to the user. The thermal grill operation may be implemented as a combination of the heat generating operation and the heat absorbing operation.

Hereinafter, the heat generating operation, the heat absorbing operation and the thermal grill operation and the heat moving operation will be described in more detail.

2.1.1. Heat Generating Operation and Heat Absorbing Operation

The feedback unit 1000 may perform the heat generating operation by using the heat outputting module 1200 to provide the hot feedback to the user. Similarly, the heat outputting module 1200 may perform the heat absorbing operation to provide the cold feedback to the user.

Figure 23:
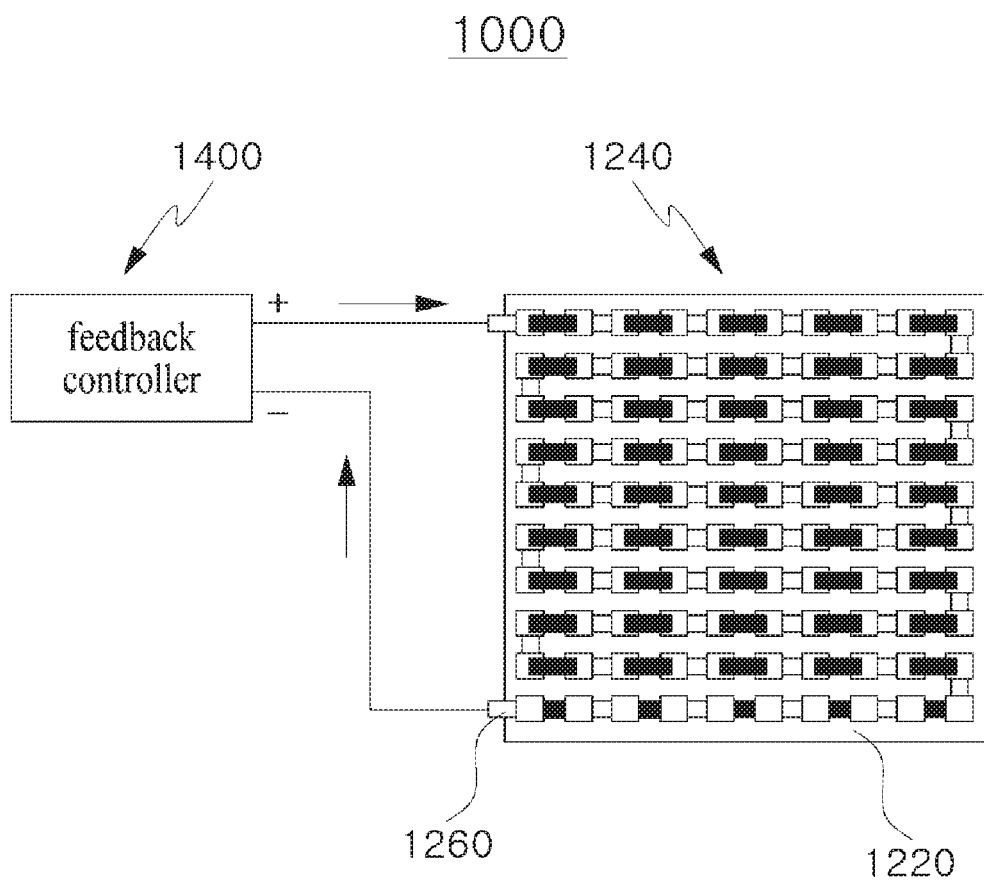
FIG. 23 illustrates a heat generating operation for providing a hot feedback according to an embodiment of the present disclosure.
Figure 24:
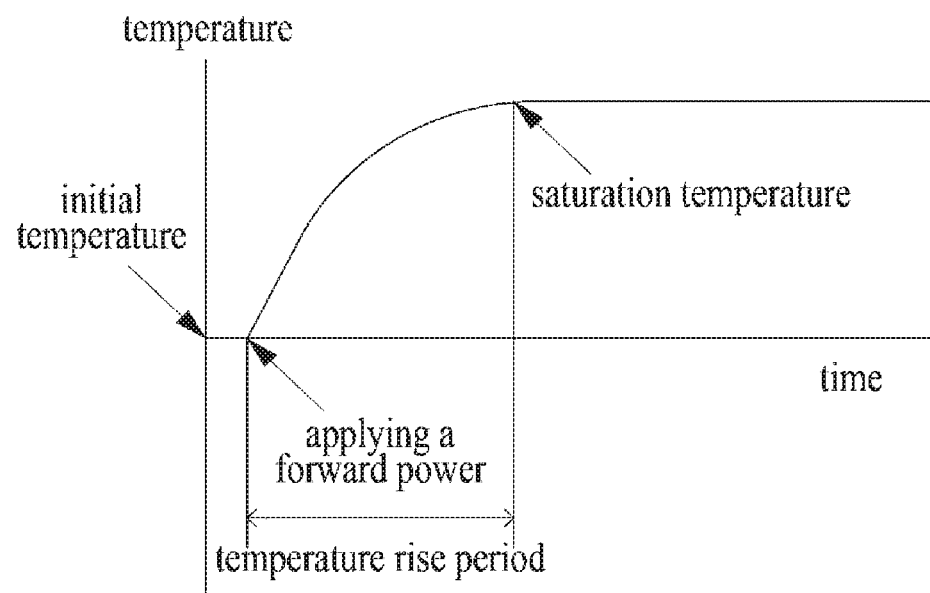
FIG. 24 is a graph relating to an intensity of the hot feedback according to an embodiment of the present disclosure.

FIG. 23 illustrates a heat generating operation for providing a hot feedback according to an embodiment of the present disclosure, and FIG. 24 is a graph relating to an intensity of the hot feedback according to an embodiment of the present disclosure.

Referring to FIG. 23, the heat generating operation may be performed by the feedback controller 1400 applying a forward-direction current to the thermoelectric couple array 1240 and inducing an exothermic reaction of the thermoelectric couple array 1240 in the direction toward the contact surface 1600. Here, when the feedback controller 1400 applies a constant voltage to the thermoelectric couple array 1240, the thermoelectric couple array 1240 starts the heat generating operation and the temperature is raised to the saturation temperature with time as shown in FIG. 24. Hereinafter, the voltage causing the heat generating operation is referred to as a "forward voltage," regardless of the actual direction of the current. Therefore, the user feels no hot sensation or a weak hot sensation at the beginning of the heat generating operation, a hot sensation increased until the temperature reaches the saturation temperature, and receives the hot feedback corresponding to the saturation temperature after a predetermined time has passed.

Figure 25:
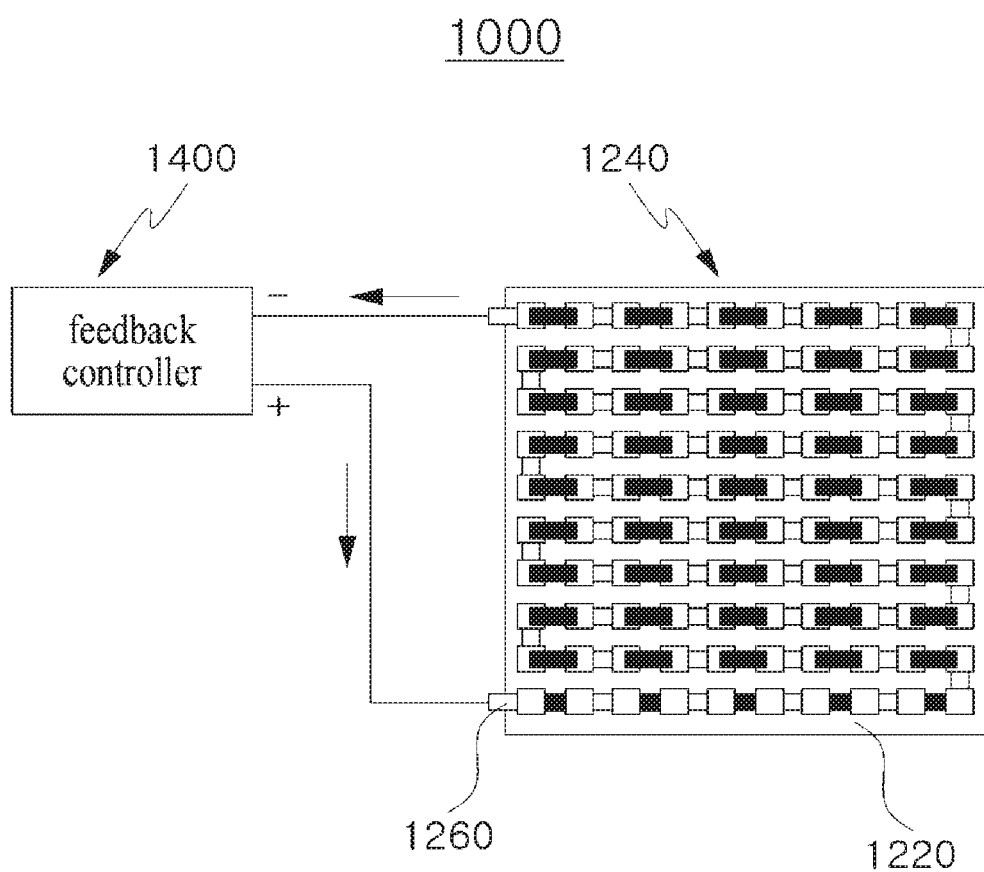
FIG. 25 illustrates a heat absorbing operation for providing a cold feedback according to an embodiment of the present disclosure.
Figure 26:
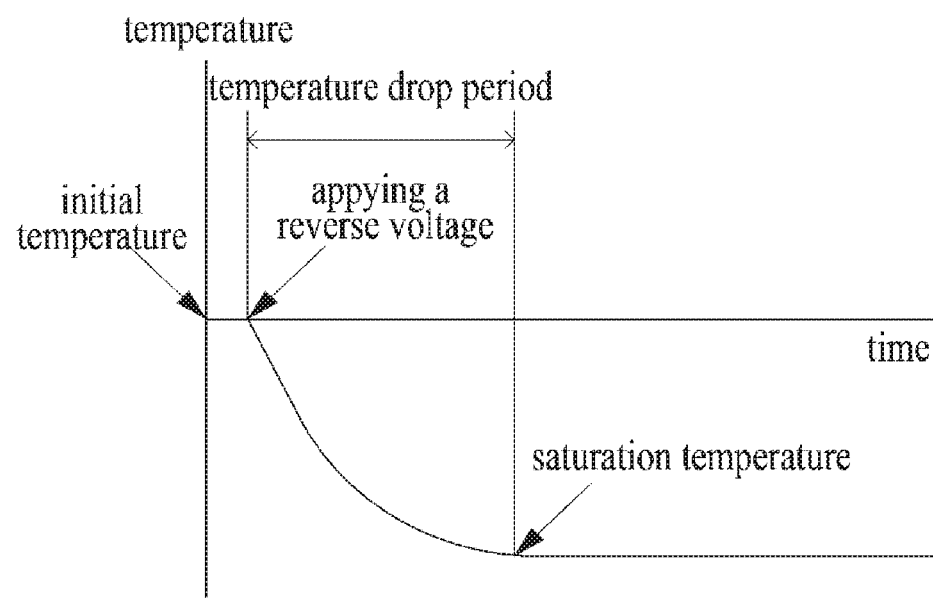
FIG. 26 is a graph relating to an intensity of the cold feedback according to an embodiment of the present disclosure.

FIG. 25 illustrates a heat absorbing operation for providing a cold feedback according to an embodiment of the present disclosure, and FIG. 26 is a graph relating to an intensity of the cold feedback according to an embodiment of the present disclosure.

Referring to FIG. 25, the heat absorbing operation may be performed by the feedback controller 1400 applying a reverse-direction current to the thermoelectric couple array 1240 and inducing an endothermic reaction of the thermoelectric couple array 1240 in the direction toward the contact surface 1600. Here, when the feedback controller 1400 applies a constant voltage to the thermoelectric couple array 1240, the thermoelectric couple array 1240 starts the heat absorbing operation and the temperature drops to the saturation temperature with time as show in FIG. 25. Hereinafter, the voltage causing the heat absorbing operation is referred to as "reverse voltage." Therefore, the user feels no cold sensation or a weak cold sensation at the beginning of the heat absorbing operation, feels a cold sensation increased until the temperature reaches the saturation temperature, and receives the cold feedback corresponding to the saturation temperature after a predetermined time has passed.

When a power is applied to a thermoelectric element, in addition to an exothermic reaction and an endothermic reaction occurring at both sides of the thermoelectric element, electric energy is converted into thermal energy and waste heat is generated. Therefore, the temperature rise amount due to the heat generating operation may be larger than the temperature drop amount due to the heat absorbing operation. Here, the temperature change amount including the temperature rise amount and the temperature drop amount means the temperature difference between the initial temperature and the saturation temperature.

Hereinafter, the heat generating operation and the heat absorbing operation performed by the thermoelectric element using electric energy will be collectively referred to as "thermoelectric operation." In addition, since the thermal grill operation to be described below is also a combined operation of the heat generating operation and the heat absorbing operation, the thermal grill operation can also be interpreted as a kind of "thermoelectric operation."

Furthermore, hereinafter, an electric power which is applied to the thermoelectric element and causes the thermoelectric operation will be referred to as "operating power." Thus, a voltage and current of the operating power will be referred to as "operating voltage" and "operating current" respectively. A time duration of the application of the operating power will be referred to as "operating duration," and a region of the thermoelectric element which performs the thermoelectric operation will be referred to as "operating region."

2.1.1.1. Intensity Control of Heat Generating Operation and Heat Absorbing Operation As described above, when the heat outputting module 1200 performs the heat generating operation or the heat absorbing operation, the feedback controller 1400 may controls an intensity of the heat generating operation or the heat absorbing operation of the heat outputting module 1200 by adjusting a voltage magnitude (or current magnitude) of the operating power. Accordingly, the feedback controller 1400 may select, among the hot feedback and cold feedback, the type of the thermal feedback to provide by adjusting a current direction of the operating power, and may control the intensity of the hot feedback or cold feedback by adjusting the magnitude of the operating voltage (or operating current).

Figure 27:
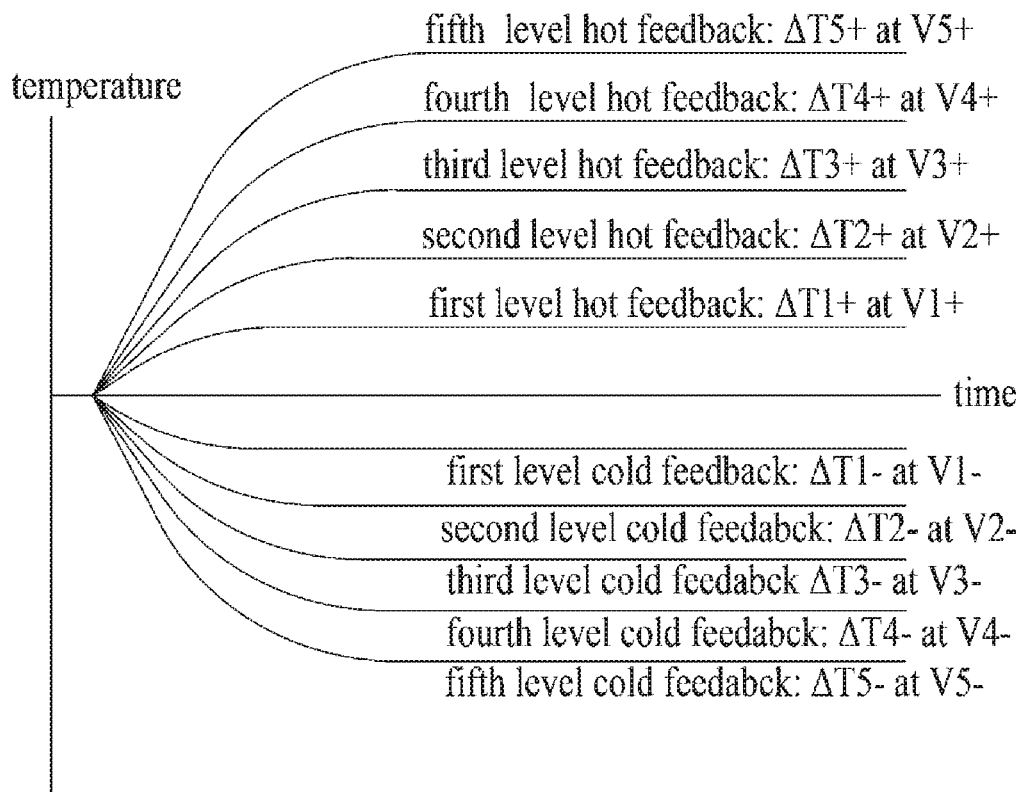
FIG. 27 is a graph relating to the hot feedback and the cold feedback of various intensities according to an embodiment of the present disclosure.
Figure 28:
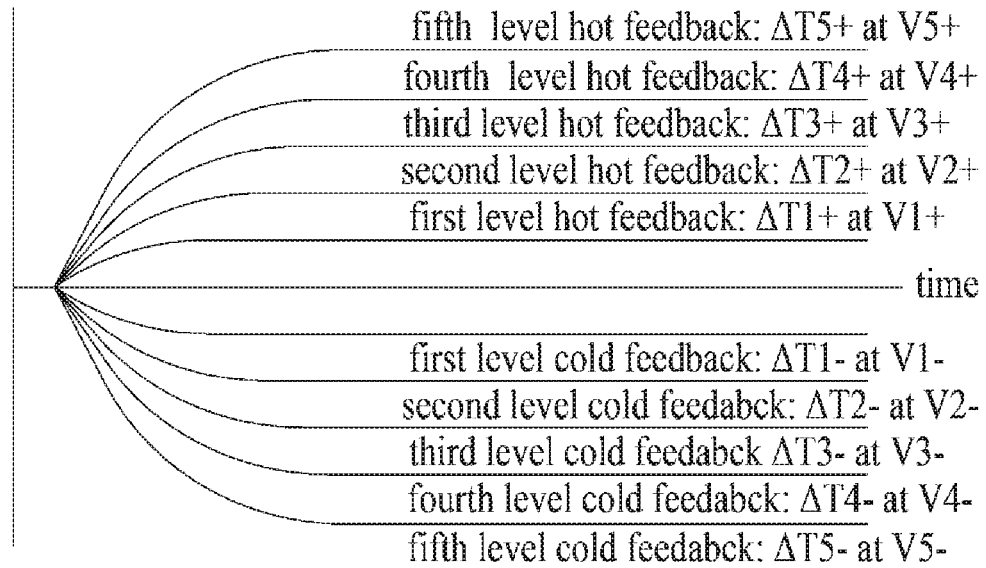
FIG. 28 is a graph relating to the hot feedback and the cold feedback of various intensities according to an embodiment of the present disclosure.

FIGS. 27 and 28 are graphs relating to the hot feedback and the cold feedback of various intensities according to an embodiment of the present disclosure.

For example, referring to FIG. 27, the feedback unit 1000 may provide ten kinds of the thermal feedback including five levels of hot feedback and five levels of cold feedback by the feedback controller 1400 adjusting a voltage magnitude of the operating power in five levels and the current direction of the operating power to the forward direction or reverse direction.

The hot feedback and the cold feedback are respectively shown to have the same number of intensity levels in FIG. 27, but it is not necessary that both feedbacks have the same number of intensity levels. That is, the number of the intensity levels of the hot feedback and the cold feedback may be different from each other. For example, the intensity of the hot feedback may be adjusted in four levels and the intensity of the cold feedback may be adjusted in be adjusted in three levels.

FIG. 27 shows that the hot feedback and the cold feedback are implemented by changing the current direction of the operating power of which the voltage magnitude is same. However, the magnitude of the operating voltage applied for the hot feedback and the cold feedback may not be equal.

In particular, when the same voltage is applied for the heat generating operation and the heat absorbing operation, the temperature rise amount of the hot feedback due to the heat generating operation is generally larger than the temperature drop amount due to the heat absorbing operation. Therefore, the voltage magnitude for the cold feedback may be greater than the voltage magnitude for the hot feedback to adjust the temperature change amount of both feedbacks to the equal level. FIG. 28 shows the hot feedback and the cool feedback with the same temperature change amount.

In the above description, the intensity of the thermal feedback is adjusted by controlling the voltage magnitude of the operating power. Similarly, the intensity of the thermal feedback may be adjusted by controlling the current magnitude of the operating power. However, the adjustment of the intensity of the thermal feedback may also be achieved in other manners.

For example, when the thermoelectric couple array 1240 of the heat outputting module 1200 has a plurality of thermoelectric couple groups 1244 that can be individually controlled, the feedback controller 1400 may adjust the intensity of the thermal feedback by controlling the operation for each thermoelectric couple group 1244. That is, the operating area control manner.

Figure 29:
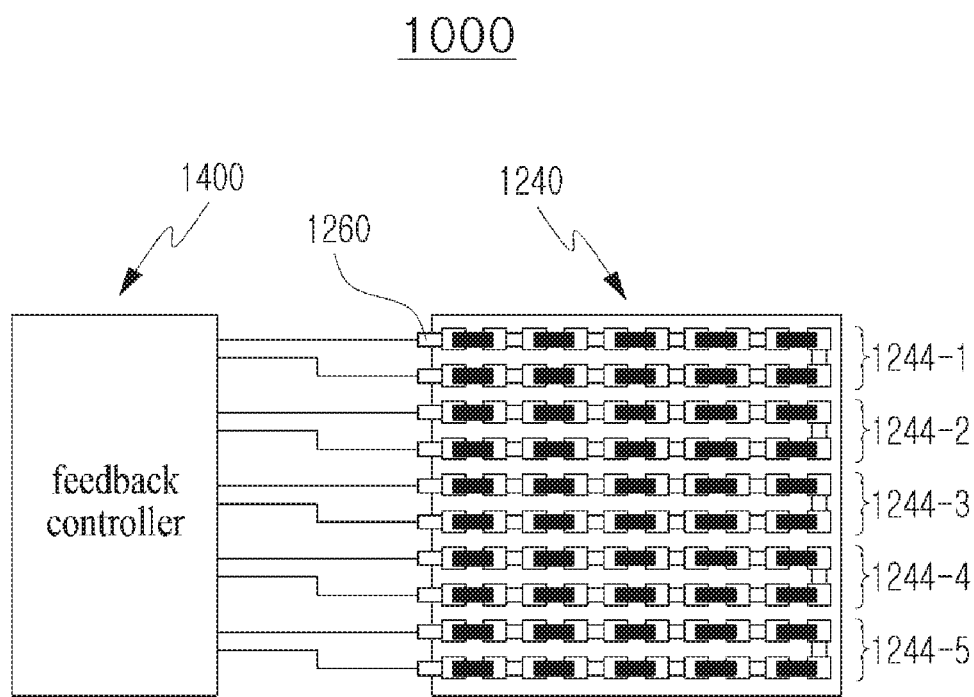
FIG. 29 illustrates the intensity adjustment of the thermal feedback using an operating area control according to an embodiment of the present disclosure.

FIG. 29 illustrates the intensity adjustment of the thermal feedback using an operating area control according to an embodiment of the present disclosure.

Referring to FIG. 29, when the thermoelectric couple array 1240 is composed of five thermoelectric couple groups 1244-1, 1244-2, 1244-3, 1244-4 and 1244-5, the feedback controller 1400 may adjust the intensity of the thermal feedback by applying the operating power to all or a portion of the thermoelectric couple groups 1244. For example, the feedback controller 1400 may apply the operating power to all of the thermoelectric couple groups 1244 so as to provide the user with the thermal feedback of the maximum intensity, apply the operating power to the four thermoelectric couple groups 1244 to provide the user with the thermal feedback of a middle-high intensity, apply the operating power to three thermoelectric couple groups 1244 to provide the user with the thermal feedback of a middle intensity, apply the operating power to two thermoelectric couple groups 1244 to provide the user with the thermal feedback of a middle-low intensity, or apply the operating power to one thermoelectric couple group 1244 to provide the user with the thermal feedback of the minimum intensity.

When the intensity of the thermal feedback is adjusted by adjusting the number of the thermoelectric couple groups 1244 to which the operating power is applied, the feedback controller 1400 may select the thermoelectric couple groups 1244 to which the operating power is to be applied in order to making the heat distribution as uniform as possible within the allowable range. To this end, the feedback controller 1400 may apply the operating power to thermoelectric couple groups 1244 in a form that the number of consecutive thermoelectric couple groups 1244 to which the operating power is applied or thermoelectric couple groups 1244 to which the operating power is not applied is minimized. Since the table shown in FIG. 29 takes into consideration the uniformity of the heat distribution, it will be more clearly understood by reference thereto.

As another example, the feedback controller 1400 may adjust the intensity of the thermal feedback by controlling the timing of the power-application. More specifically, the feedback controller 1400 may apply power to the thermoelectric couple array 1240 as an electric signal in the form of a PWM (Pulse Width Modulation) signal having a duty cycle to control the intensity of the thermal feedback. That is, the operating time control manner.

Figure 30:
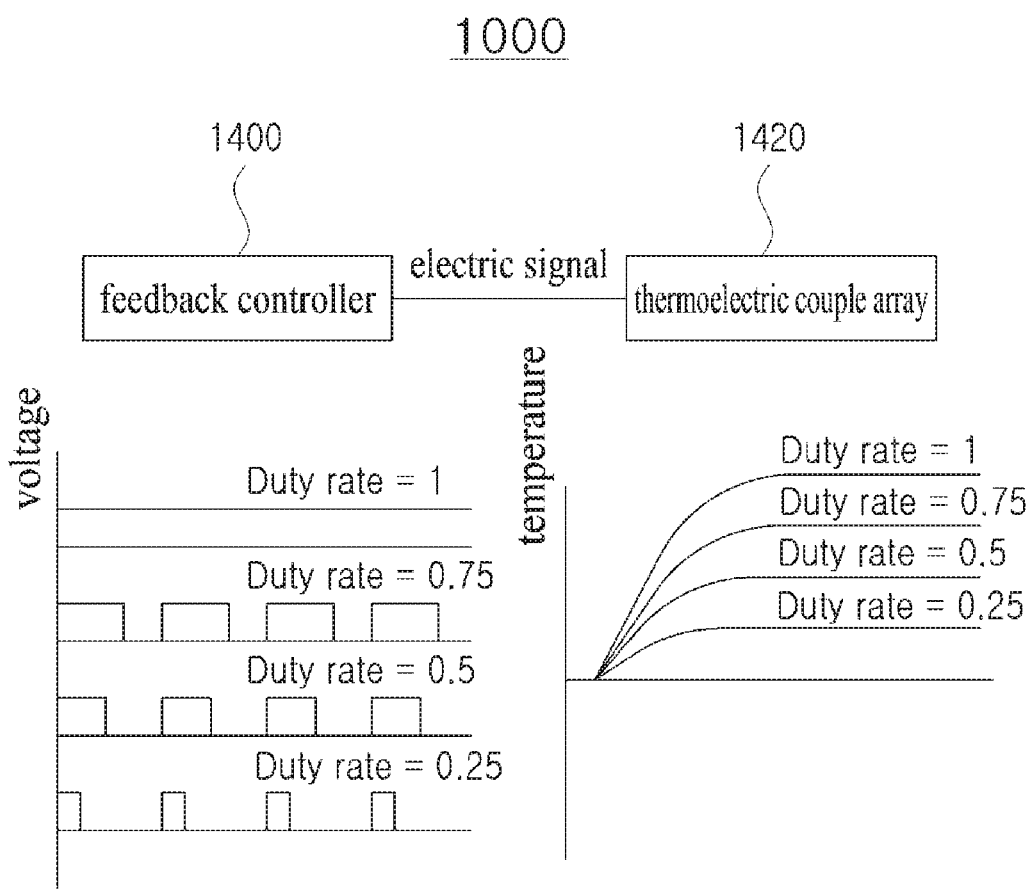
FIG. 30 illustrates the intensity adjustment of the thermal feedback using an operating time control according to an embodiment of the present disclosure.

FIG. 30 illustrates the intensity adjustment of the thermal feedback using an operating time control according to an embodiment of the present disclosure.

Referring to FIG. 30, it is shown that the intensity of the thermal feedback is adjusted by the duty rate of the electric signal.

As described above, by adjusting the intensity of the thermal feedback, the thermal feedback may be provided with various levels of intensity, such as strong hot sensation, weak hot sensation, weak cold sensation, strong cold sensation, etc., instead of simply providing the hot sensation and cold sensation to the user. Such multi-level thermal feedback can provide a greater immersion for the user in a game environment or a virtual/augmented reality environment, and also makes it possible to inspect a patient's senses more precisely when applied to a medical device.

In addition, the adjustment of the intensity of the thermal feedback may also be performed by mixing the above-described manners. In other words, the intensity adjustment of the thermal feedback may be achieved by using the operating power control, the operating area control, the operating time control or combinations thereof.

2.1.2. Thermal Grill Operation

The feedback unit 1000 may provide the thermal grill feedback in addition to the hot feedback and cold feedback. When a user is stimulated with the hotness and the coldness at the same time, the user recognizes not the hotness or the coldness but a pain. Thermal grill sensation refers a sense of pain perceived by a user whose body is stimulated with the hotness and coldness at the same time. Thus, the feedback unit 1000 may provide the thermal grill feedback to the user through a thermal grill operation in which the heat generating operation and heat absorbing operation are combined.

The feedback unit 1000 may perform the thermal grill operation in various ways to provide the thermal grill feedback, which will be described later, after explaining the types of the thermal grill feedback.

2.1.2.1. Types of Thermal Grill Feedback

The thermal grill feedback may include a neutral grill feedback, a hot grill feedback, and a cold grill feedback.

The neutral grill feedback, the hot grill feedback, and the cold grill feedback cause the user a neutral pain, a hot pain and a cold pain, respectively. The neutral pain means a pain sensation without feelings of warmth and coldness, hot pain means a pain sensation with hot sensation, and a cold pain means a pain sensation with a cold sensation.

For example, the neutral pain may be caused when an intensity ratio of hotness and coldness applied to the user are within a predetermined range. The ratio causing the neutral pain (hereinafter referred to as "neutral ratio") may be different for each part of the body that is provided with the thermal feedback, and even if it is the same body part, it may be slightly different for each individual. However, in most case the neutral pain tends to be felt where the intensity of the cold feedback is given larger than the intensity of the hot feedback.

Here, the intensity of the thermal feedback may be related to the amount of heat that the feedback device 100 applies to or absorbs from the body part that is in contact with the contact surface 1600. Therefore, when the thermal feedback is applied to a certain area for a certain period of time, the intensity of the thermal feedback may be related to the difference between a skin temperature of the target site to which the thermal feedback is applied and the temperature of the contact surface 1600.

Human body temperature is usually between 36.5 and 36.9° C., and the skin temperature varies from person to person, but it is known to be about 30~32° C. on average. The temperature of the palm is about 33° C. which is slightly higher than the average skin temperature. The above-mentioned temperature values may be somewhat different depending on the individual, and even the same person may vary to some extent.

According to one experimental example, it was confirmed that a sensation of neutral pain was felt when a hot sensation of about 40° C. and a cold sensation of about 20° C. were given to the palm of 33° C. This is due to the hotness of +7° C. and coldness of −13° C., based on the palm temperature, so the neutral ratio in terms of temperature (hereinafter referred to as "neutral temperature ratio") may be equivalent to 1.86.

As can be seen from this, in case of most people, when the hotness and coldness are continuously applied to the same body area, the neutral temperature ratio is in the range of about 1.5 to 5, where the neutral temperature ratio is the ratio of the temperature drop amount caused on the skin by the cold feedback to the temperature rise amount caused on the skin by the hot feedback. In addition, the hot grill sensation may be felt when the ratio of the temperature drop amount to the temperature rise ratio (hereinafter referred to as "temperature ratio") is smaller than the neutral temperature ratio, and the cold grill sensation may be felt when the temperature ratio is greater than the neutral temperature ratio.

2.1.2.2. Thermal Grill Operation by Using Operating Power Control

The feedback unit 1000 may perform the thermal grill operation by using the operating power control manner. The thermal grill operation using the operating power control may be applied to the feedback unit 1000 in which the thermoelectric couple array 1240 is composed of a plurality of thermoelectric couple groups 1244 which are individually controllable.

Specifically, in the thermal grill operation using the operating power control, the feedback controller 1400 may apply a forward power to a part of the thermoelectric couple groups 1244 to perform the heat generating operation and apply a reverse power to another part of the thermoelectric couple groups 1244 to perform the heat absorbing operation. Therefore, the heat outputting module 1200 may be outputting both hot feedback and cold feedback.

Figure 31:
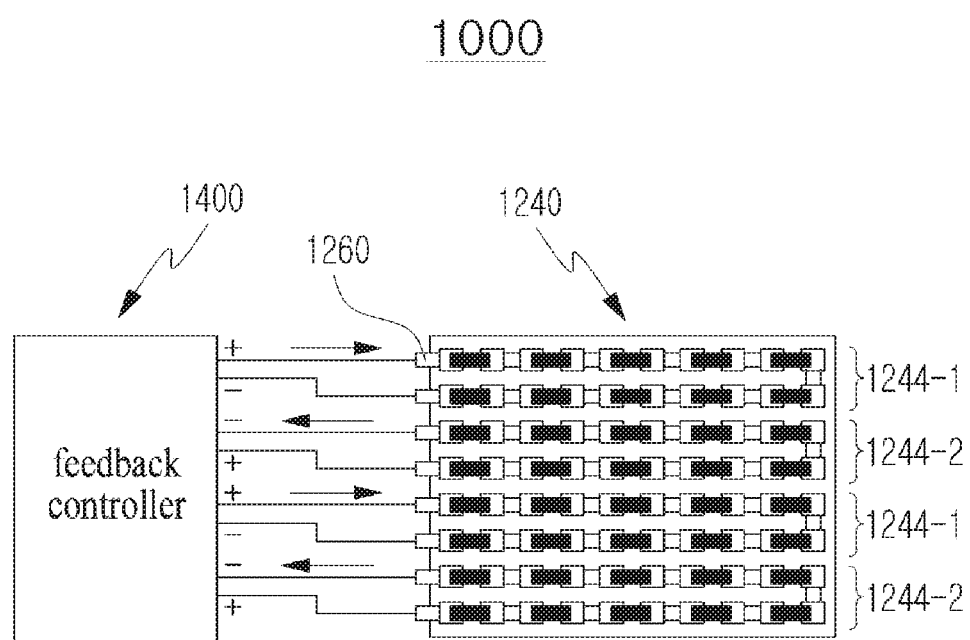
FIG. 31 illustrates a thermal grill operation using an operating power control according to an embodiment of the present disclosure.

FIG. 31 illustrates a thermal grill operation using an operating power control according to an embodiment of the present disclosure.

Referring to FIG. 31, the thermoelectric couple array 1240 includes a plurality of thermoelectric couple groups 1244 arranged to form a plurality of lines. The feedback controller 1400 may control the first thermoelectric couple groups 1244-1 (e.g., the thermoelectric couple groups forming the odd-numbered lines) to perform the heat generating operation and the second thermoelectric couple groups 1244-2 (e.g., the thermoelectric couple groups forming the even-numbered lines) to perform the heat absorbing operation. In some embodiments, the thermoelectric couple groups 1244 perform the heat generating operation and the heat absorbing operation alternately according to the line arrangement. The user may receive the hot heat and cold heat at the same time and the thermal grill feedback may be provided to the user. Here, the arrangement of the odd-numbered lines and the even-numbered lines is arbitrary, and the opposite arrangement may alternatively be chosen.

The feedback unit 1000 may provide the neutral grill feedback by adjusting the temperature ratio caused to the neutral temperature ratio.

FIG. 32 is a table of the operating voltages for providing the neutral grill feedback by the operating power control manner according to an embodiment of the present disclosure.

For example, referring to FIG. 32, assuming that: 1) the feedback controller 1400 is able to apply, e.g., five voltage values for the forward operating power and five voltage values for the reverse operating power to the heat outputting module 1200; 2) the heat outputting module is able to perform five intensity levels of the heat generating operation and five intensity levels of the heat absorbing operation; 3) the temperature rise amount due to the heat generating operation and the temperature drop amount due to the heat absorbing operation are same when the heat generating operation and the heat absorbing operation which have the same intensity level are performed; and 4) the difference of the temperature change amount between each intensity level is constant, in the case that the neutral ratio is set to 3, the feedback controller 1400 may provide the neutral grill feedback by applying the first level forward voltage to the first thermoelectric couple group 1244-1 and the third level reverse voltage of the third level to the second thermoelectric couple group 1244-2.

Similarly, in case that the neutral ratio is 2.5, the feedback controller 1400 may provide neutral grill feedback by applying the second level forward voltage to the first thermoelectric couple group 1244-1 and the fifth level reverse voltage to the second thermoelectric couple group 1244-2. In case that the neutral ratio is 4, the feedback controller 1400 may output the neutral grill feedback by applying the first level forward voltage to the first thermoelectric couple group 1244-1 and the fourth level reverse voltage to the second thermoelectric couple group 1244-2.

Or in case that the neutral ratio is 2, the feedback controller 1400 may provide the neutral grill feedback by applying the first level forward voltage to the first thermoelectric couple group 1244-1 and the second level reverse voltage to the second thermoelectric couple 1244-2 or by applying the second level forward voltage to the first thermoelectric couple group 1244-1 and the fourth level reverse voltage to the second thermoelectric couple 1244-2.

The neutral grill feedback according to the combination of the second level forward voltage and the fourth level reverse voltage may cause greater pain sensation than the neutral grill feedback according to the combination of the first level forward voltage and the second level reverse voltage. This means that the feedback device 1000 can adjust the intensity of the thermal grill feedback.

The above description related to the thermal grill operation for providing the neutral grill feedback is illustrative, and the present disclosure is not limited thereto. For example, the number of the intensity level of the thermal feedback doesn't need to be five, and the number of the intensity levels between the hot feedback and the cold feedback may be varied. Also, the interval of the temperature change amount of each level of the thermal feedback should not be constant, and the interval of the voltage magnitude of each level of the operating power may be constant instead of the temperature interval.

The feedback controller 1400 may provide the hot grill feedback by adjusting the voltage value or the current value of the forward operating power and the reverse operating power and setting the temperature ratio to be smaller than the neutral ratio, or may provide the cold grill feedback by adjusting the voltage value or the current value of the forward operating power and the reverse operating power and setting the temperature ratio to be greater than the neutral ratio.

For example, referring back to FIG. 32, in case of the neutral ratio is set to 3, the feedback controller 1400 may output the hotness and coldness at a ratio lower than the neutral ratio by applying the forward voltage of the first level to the first thermoelectric couple group 1244-1 and the reverse voltage of the first or second level to the second thermoelectric couple group 1244-2 and, thereby, the feedback controller 1400 may provide the hot grill feedback which makes the user feel the pain sensation and hot sensation simultaneously. The forward voltage for the hot grill feedback does not necessarily have to be the forward voltage used for the neutral grill feedback. The feedback controller 1400 may control the heat outputting module 1200 to provide hot grill feedback using the fourth level forward voltage and the fourth level reverse voltage.

Similarly, in case of the neutral ratio is set to 3, the feedback controller 1400 may generate the cold grill feedback using the first level forward voltage and the fourth level reverse voltage or using the first level forward voltage and the fifth level reverse voltage.

Since the user cannot feel the pain sensation from the hot grill feedback or the cold grill feedback when the forward voltage and the reverse voltage are applied at a ratio largely deviated from the neutral ratio, it may be desirable to adjust the level of the forward voltage and reverse voltage so that the ratio of coldness to hotness is close to the neutral ratio.

2.1.2.3. Thermal Grill Operation by Using Operating Area Control

In the above description, the feedback device 100 may provide the thermal grill feedback by adjusting the voltage value or current value of the operating power applied to the thermoelectric couple group 1244 where the region for performing the heat generating operation and the region for performing the heat absorbing operation have same size and alternately arranged in the thermoelectric couple array 1240. The feedback device 100 may provide the thermal grill feedback by adjusting the area size of the region for performing the heat generating operation and the region for performing the performing the heat absorbing operation.

Specifically, the thermal grill operation using the operating area control manner may be performed by adjusting the area of the thermoelectric couple group 1244 to which the forward operating power is applied and the area of the thermoelectric couple group 1244 to which the reverse operating power is applied.

Figure 33:
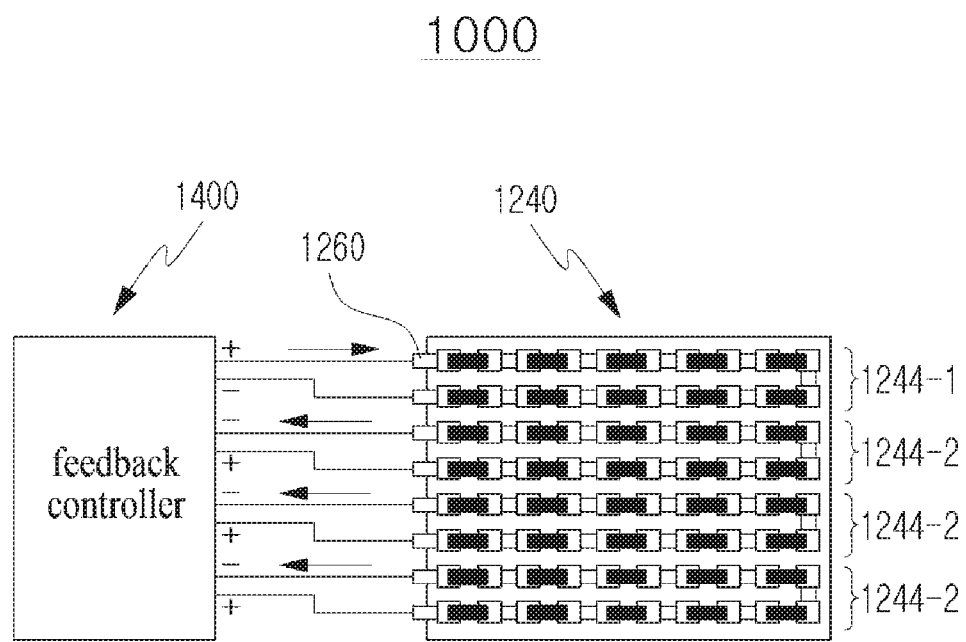
FIG. 33 illustrates a thermal grill operation using an operating area control according to an embodiment of the present disclosure.

FIG. 33 illustrates the thermal grill operation using the operating area control according to an embodiment of the present disclosure.

Referring to FIG. 33, the electric couple array 1240 includes a plurality of thermoelectric couple groups 1244 arranged to form a plurality of lines. Assuming that 1) the area size of each line is the same, and 2) the forward voltage and reverse voltage are set to voltage values that make the temperature change amount of the hot feedback and the cold feedback equal to each other: in the case that the neutral ratio is 3, the feedback controller 1400 may apply the forward voltage and reverse voltage to the heat outputting module 1200 so that three thermoelectric couple groups 1244-2 per one thermoelectric couple group 1244-1 performing the heat generating operation may perform the heat absorbing operation. Thereby, the area of the contact surface 1600 providing the cold feedback is three times the area of the contact surface 1600 providing the hot feedback, and the feedback device 100 may provide the neutral grill feedback.

The neutral ratio may mean the ratio of the area providing the cold feedback to the area providing the hot feedback instead of the ratio of temperature difference of the cold feedback to temperature difference of the hot feedback. The neutral ratio in terms of area (hereinafter referred to as "neutral area ratio") may be equal to the neutral temperature ratio, but may be a somewhat different value.

Additionally, the feedback controller 1400 may reduce or increase the number of thermoelectric couple groups 1244-2 performing the heat absorbing group per thermoelectric couple group 1244-1 performing the heat generating operation so that the feedback device 100 is also able to perform the hot grill feedback or the cold grill feedback.

Although each of the thermoelectric couple groups 1244 has been described as having the same area size in FIG. 33, the thermoelectric couple groups 1244 may alternatively be designed in consideration of the neutral area ratio.

Figure 34:
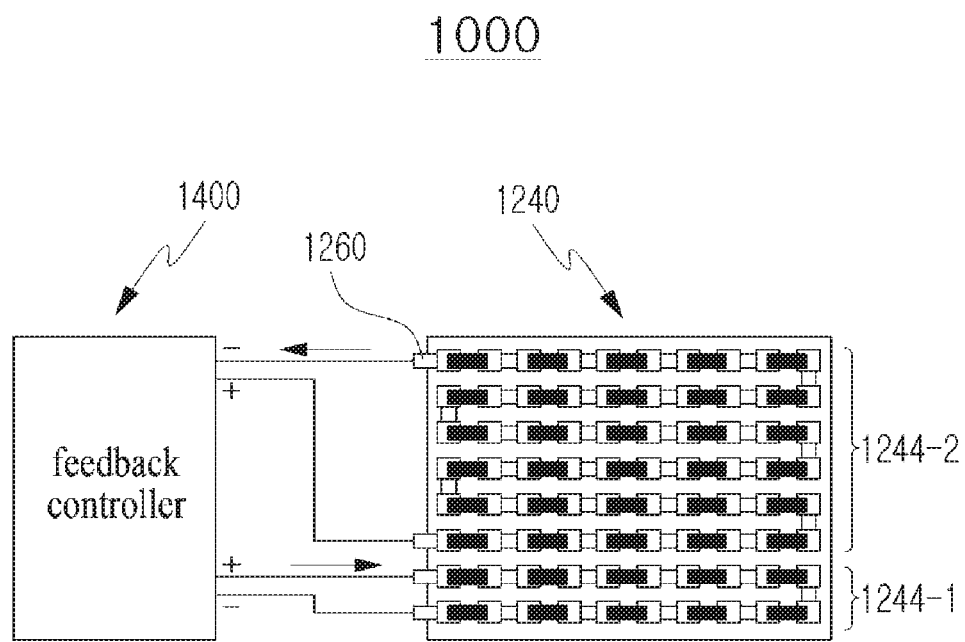
FIG. 34 illustrates a thermoelectric couple array composed of thermoelectric couple groups having different area sizes for providing a thermal grill feedback using the operating area control according to an embodiment of the present disclosure.

FIG. 34 illustrates a thermoelectric couple array 1240 composed of thermoelectric couple groups 1244 having different area sizes for providing the thermal grill feedback using the operating area control according to an embodiment of the present disclosure.

Referring to FIG. 34, the first thermoelectric couple group 1244-1 and the second thermoelectric couple group 1244-2 are designed to have different area sizes. For example, the area ratio of the second thermoelectric couple group 1244-2 to first thermoelectric couple group 1244-2 may be the neutral area ratio. Using this thermoelectric couple array 1240, the feedback controller 1400 may apply the forward voltage to the first thermoelectric couple groups 1244-1 and the reverse voltage to the second thermoelectric couple group 1244-2 so that the feedback device may provide the neutral grill feedback.

The above description has been made on the assumption that the forward voltage and the reverse voltage, which are used for outputting the thermal grill feedback according to the operating area control manner, causes the same temperature change amount both in the hot feedback and cold feedback. However, if the temperature change amount of the hot feedback according to the forward voltage and the temperature difference of the cold feedback according to the reverse voltage are different from each other, the area ratio should be adjusted considering the ratio of the temperature change amount.

In other words, to provide the neutral pain sensation, the value calculated based on two parameters of the ratio of the cold area to the hot area which is the area ratio and the ratio of the cold temperature difference to the hot temperature difference which is the temperature ratio may be the neutral ratio. For example, the feedback device 100 may provide neutral grill feedback by adjusting the product of the temperature ratio and the area ratio to be the neutral ratio. The neutral ratio may be the product of the neutral temperature ratio and the neutral area ratio.

The thermal grill operation using the operating area control manner according to the above-described has an advantage in that the feedback intensity can be selected more freely than the thermal grill operation using the operating power control manner.

When the same voltage is applied to the thermoelectric element to perform the heat generating operation and the heat absorbing operation, the temperature change amount of the heat generating operation is generally larger than the temperature change amount of the heat absorbing operation. In addition, for outputting the neutral grill feedback, the temperature drop amount of the cold feedback is approximately two to three times larger than the temperature rise amount of the hot feedback. Considering these points, the ratio of the magnitude of the reverse voltage to the forward voltage may be relatively large. Therefore, to provide the neutral grill feedback by using the operating power control, the feedback controller 1400 needs to output an electric signal in a wide voltage range. This means, when the voltage range of the applied power supply is limited, it is practically difficult to adjust the intensity of the thermal grill feedback.

On the other hand, since the neutral grill feedback according to the operating area control manner is processed by adjusting the area size of the hot region and the cold region and the feedback device 1000 may satisfy the neutral ratio by regulating the area ratio, the feedback device 1000 may adjust the intensity of the thermal grill feedback more easily.

Specifically, in the discussion with reference to FIG. 34, the feedback controller 1400 may control the heat outputting module 1200 to provide a strong neutral grill feedback by increasing the magnitudes of both the forward and reverse voltages together or control the heat outputting module 1200 to provide a weak neutral grill feedback by decreasing the magnitudes of both the forward and reverse voltages together.

As already mentioned in the description related to FIG. 34, the neutral ratio for neutral grill feedback has already been satisfied by the ratio of the cold area to the hot area, the feedback controller 1400 may relatively freely control the intensity of the thermal grill feedback by adjusting the magnitude of the forward voltage and the reverse voltage.

2.1.2.4. Thermal Grill Operation According to Operating Time Control

The thermal grill operation may be implemented according to the operating time control manner as well. Specifically, the thermal grill operation according to the operating time control manner may be implemented by performing the heat generating operation and the heat absorbing operation alternately in time. If the hot feedback and the cold feedback are transmitted to the user alternately in a relatively short time interval, the human senses may interpret it as a pain sensation.

The feedback controller 1400 may alternately apply a forward voltage and a reverse voltage to the heat outputting module 1200 so that the heat generating operation and the heat absorbing operation are alternately performed. Here, the neutral grill feedback may be performed by adjusting at least one of the voltage magnitude of the operating power or the application duration of the forward operating power and the reverse operating power.

Figure 35:
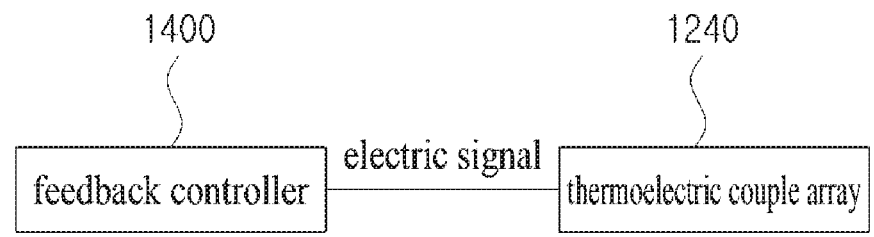
FIG. 35 illustrates an example of a thermal grill operation using an operating time control according to an embodiment of the present disclosure.
Figure 35:
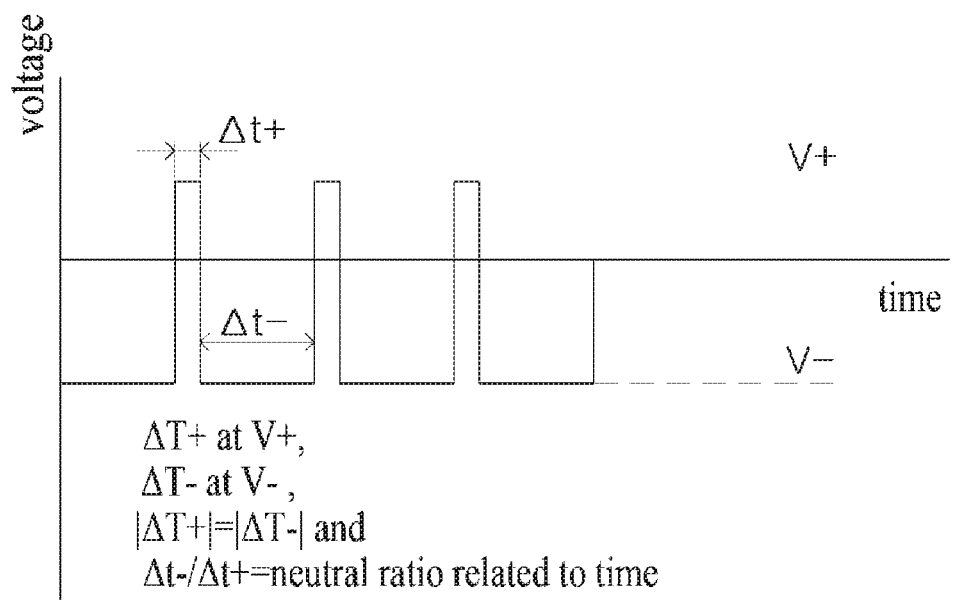

FIG. 35 illustrates an example of a thermal grill operation using an operating time control according to an embodiment of the present disclosure.

If the forward voltage and the reverse voltage are set to make the temperature change amount of the hot feedback equal to the temperature amount of the cold feedback, the feedback controller 1400 may adjust the ratio of the application duration of the reverse operating power to the application duration of the forward operating power to the neutral ratio by controlling the output timing of the electric signal.

For example, referring to FIG. 35, if the neutral ratio is 3, the feedback controller 1400 may apply the forward voltage for 20 ms and apply the reverse voltage for 60 ms to provide the neutral grill feedback. Here, the hot grill feedback or the cold grill feedback may be provided by adjusting the ratio of the signal output timing. Here, when the ratio of the time duration is set to the neutral ratio, the feedback controller 1400 may adjust the intensity of the thermal grill operation by increasing or decreasing the magnitudes of the forward voltage and the reverse voltage together.

Figure 36:
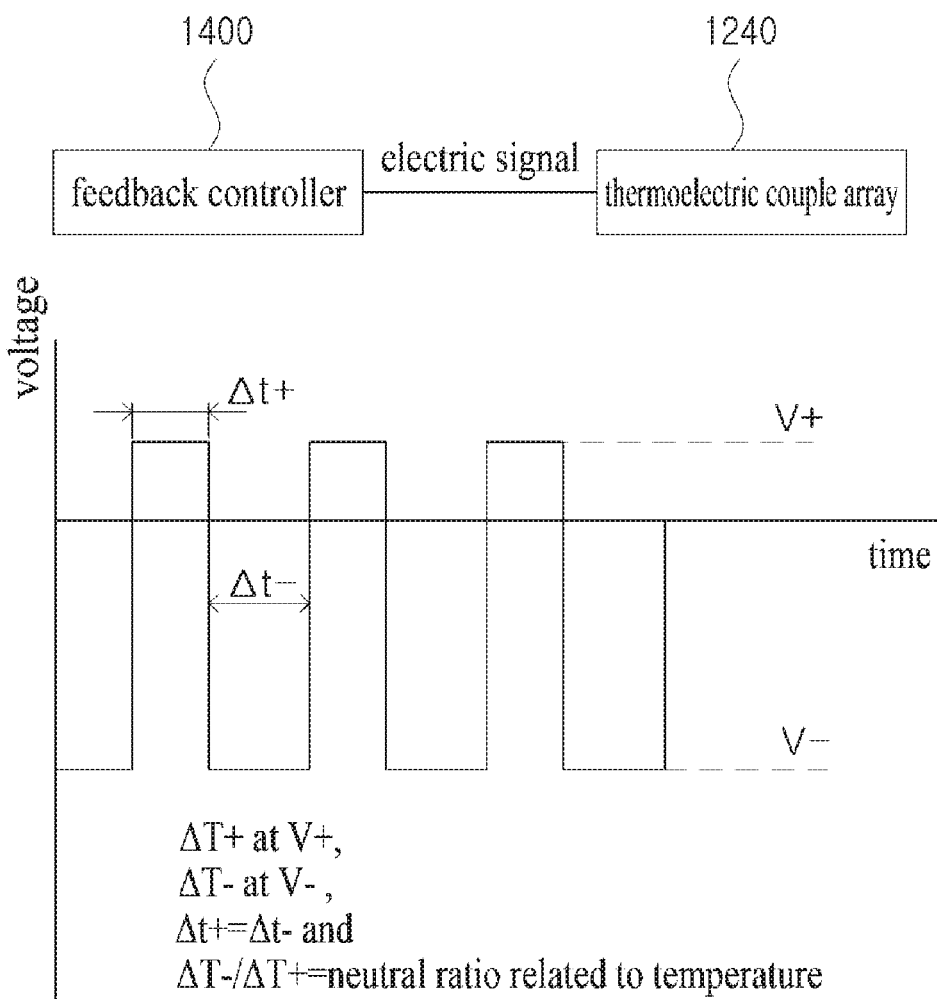
FIG. 36 illustrates another example of a thermal grill operation using an operating time control according to an embodiment of the present disclosure.

FIG. 36 illustrates another example of the thermal grill operation using the operating time control according to an embodiment of the present disclosure.

In some embodiments, the application duration of the hot feedback and the cold feedback are set to the same size. In such embodiments, the feedback controller 1400 may adjust the temperature change for the hot feedback and the cold feedback to be the neutral ratio during each application duration by adjusting the voltage value of the electric signal. For example, referring to FIG. 36, when the neutral ratio is 3, the feedback controller 1400 may apply the forward voltage and the reverse voltage alternately at intervals of 20 ms and adjust the temperature drop amount by the heat absorbing operation to be three times the temperature rise amount by the heat generating operation to provide the neutral grill feedback. Also, the hot grill feedback or the cold grill feedback may be achieved by adjusting the magnitude of the forward voltage or the reverse voltage.

In some embodiments, the feedback controller 1400 may also adjust the time duration and the magnitude of the voltage together.

The thermal grill operation of the operating power control or the operating area control causes the user to feel a pain sensation, but physically it applies the hot heat and cold heat to the user's body at the same time. If the sensory organ of the user is constantly stimulated by the pain sensation of the thermal grill feedback, the user's body senses an after-sensation for a certain period of time even after the thermal grill feedback is removed. Since the thermal grill feedback is typically a feeling close to pain, the user may feel uncomfortable due to the after-sensation. The cause of this after-sensation is due to the prolonged exposure of the skin's hot and cold spots to the given hotness and coldness of a somewhat higher intensity to provide effective thermal grill feedback. On the other hand, the thermal grill operation according to the operating time control manner does not continuously stimulate the skin's hot and cold spots, and thus the after-sensation effect is somewhat eliminated.

2.1.2.5. Thermal Grill Operation Combined with Operating Area Control and Operating Time Control The thermal grill operation may be performed by combining the concept of the operating area control manner and the operating time control manner described above.

In some embodiments, thermoelectric couple array 1240 may include multiple areas that are independently controlled by feedback controller 1400. In such embodiments, the thermal grill operation may be achieved by having opposite and alternating feedbacks in different areas. For instance, the thermal grill may be achieved when feedback controller 1400 cycles between a first interval and a second interval. During the first interval, feedback controller 1400 may perform a heat generating operation (i.e., output a hot feedback) in a first area while it simultaneously performs a heat absorbing operation (i.e., output a cold feedback) in a second area. In the second interval, feedback controller 1400 may alternate operations and perform the heat absorbing operation in the first area while it performs the heat generating operation in the second area. In some embodiments, feedback controller 1400 may alternate between the first and the second interval with a uniform periodicity. In other embodiments, the time intervals may have arbitrary time lengths or may be dynamically controlled by, for example, application controller 2700.

Figure 37:
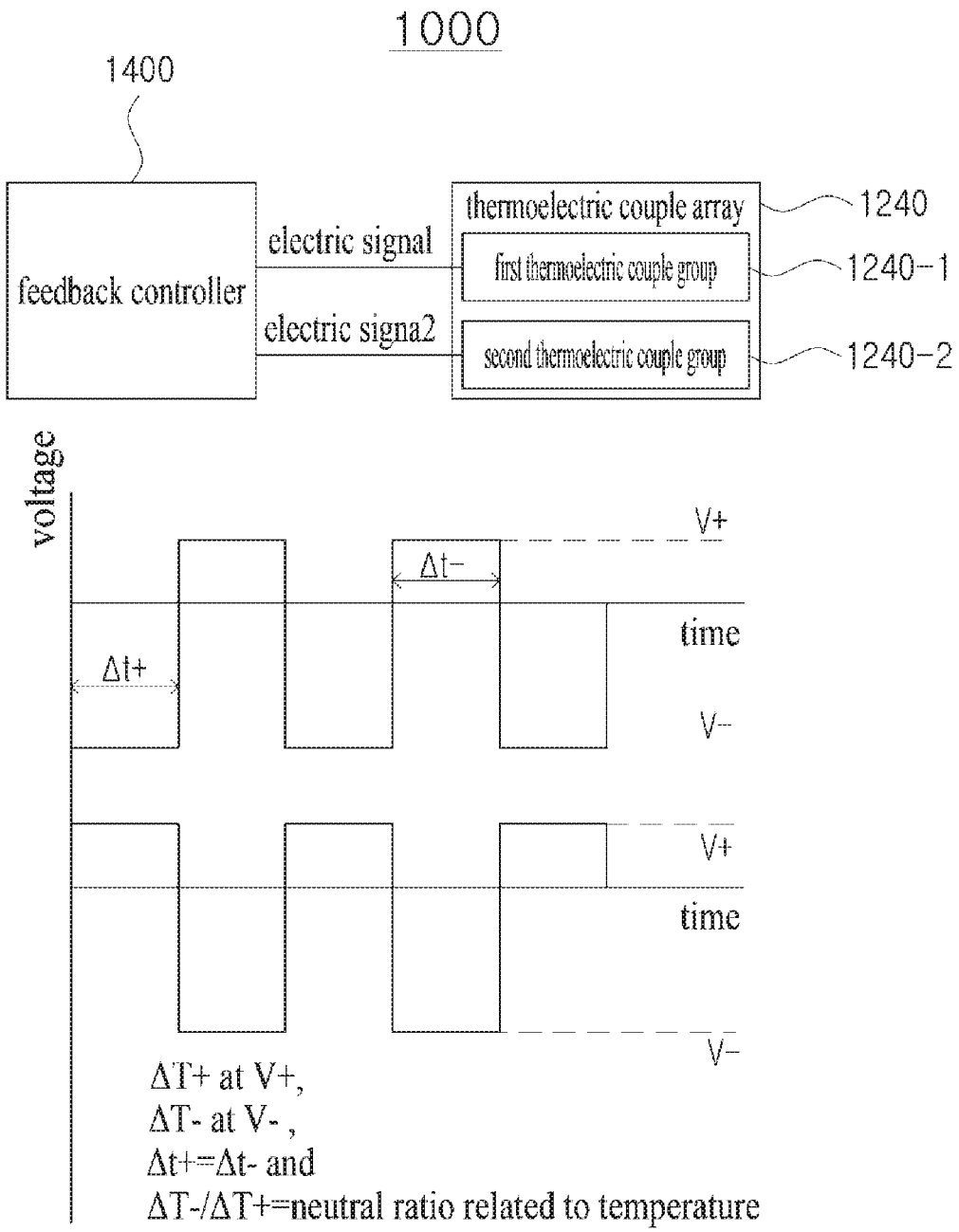
FIG. 37 illustrates an example of a thermal grill operation using a combination of an operating area control and an operating time control according to an embodiment of the present disclosure.

FIG. 37 illustrates an example of the thermal grill operation using a combination of the operating area control and the operating time control according to an embodiment of the present disclosure.

Referring to FIG. 37, the thermoelectric couple array 1240 may include a first thermoelectric couple group 1244-1 performing a first operation and a second thermoelectric couple group 1244-2 performing a second operation. Here, both the first operation and the second operation includes the heat generating operation and the heat absorbing operation which are carried out alternately, and the heat generating operation of the first operation and the heat absorbing operation of the second operation are carried out together, and the heat absorbing operation and the heat generating operation are carried out together.

The feedback controller 1400 may control the first thermoelectric couple group 1244-1 to perform the first operation by sequentially applying the forward voltage and the reverse voltage to the first thermoelectric couple group 1244-1, and control the second thermoelectric couple group 1244-2 to perform the second operation by sequentially applying the reverse voltage and the forward voltage to the second thermoelectric couple group 1244-2. Accordingly, the heat outputting module 1200 may output the hot feedback and the cold feedback simultaneously in the region of the first thermoelectric couple group 1244-1 and the region of the second thermoelectric couple 1244-2, so that the feedback device 100 may provide the thermal grill feedback.

When the first thermoelectric couple group 1244-1 and the second thermoelectric couple group 1244-2 have the same area size and the time duration of the heat generating operation and the time duration of the heat absorbing operation are the same in the first operation and the second operation, the feedback device 100 may provide the neutral grill feedback, the hot grill feedback, or the cold grill feedback by adjusting the voltage ratio of the reverse voltage to the forward voltage or the temperature ratio.

Here, the time duration of the heat generating operation and the heat absorbing operation may be relatively long, unlike the case of performing the thermal grill operation according to the operating time control manner. In the case of the operating time control manner, it may invoke an illusion to a human sensory organ depending on the time interval of the hot feedback and cold feedback. On the contrary, in the case of the operating time control manner combined with the operating area control manner, the hot feedback and the cold feedback are simultaneously provided to the user, so that the pain sensation can be felt even if the time interval of the heat generating operation and the heat absorbing operation is relatively long. That is, in the case of the operating time control manner, each of the application duration of the forward voltage and the application duration of the reverse voltage needs to be adjusted to be less than the recognition time when the user to feel hotness or coldness. On the contrary, the operating time control manner combined with the operating area control manner is free from the time duration limit.

Furthermore, since the thermal grill operation according to the combined operating time control manner does not continuously provide the hot heat and cold heat to the user's skin and provide the hot heat and cold heat periodically to the user's skin, the skin damage can be minimized. For this purpose, it may not be desirable for the time duration to be too long.

Although the thermoelectric couple array 1240 has been described as having two thermoelectric couple groups 1244 that perform staggered operations with respect to FIG. 37, the thermal grill operation may be applied according to the combined manner to various types of the thermoelectric couple arrays 1240.

Figure 38:
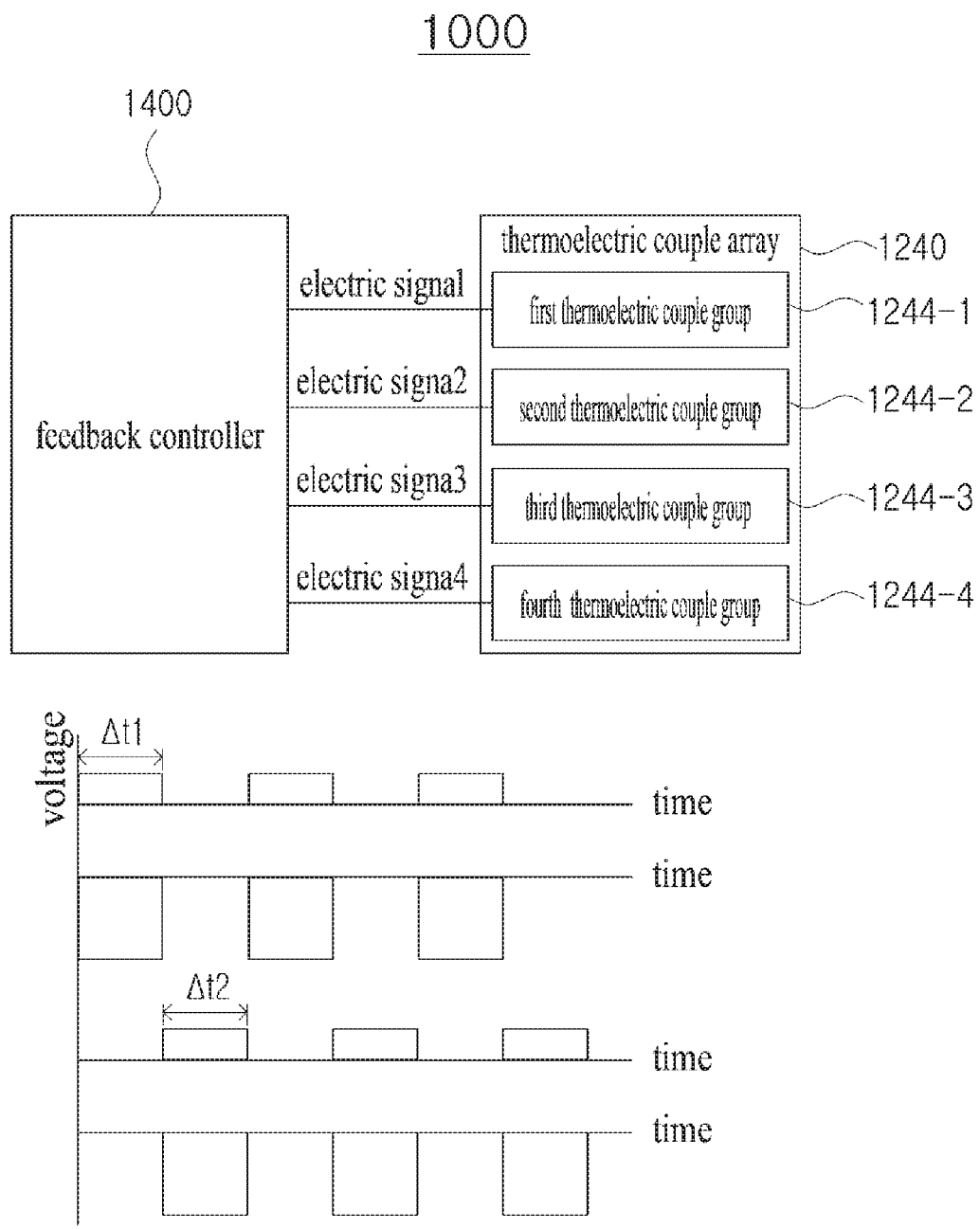
FIG. 38 illustrates another example of a thermal grill operation using a combination of an operating area control and an operating time control according to an embodiment of the present disclosure.

FIG. 38 illustrates another example of a thermal grill operation using a combination of an operating area control and an operating time control according to an embodiment of the present.

Referring to FIG. 38, the thermoelectric couple array 1240 may include four thermoelectric couple groups 1244-1, 1244-2, 1244-3 and 1244-4. Here, the feedback controller 1400 may apply the following electric signals to each thermoelectric couple group 1244: During the first-time period, a forward voltage is applied to the first thermoelectric couple group 1244-1 to perform the heat generating operation, and the reverse voltage is applied to the second thermoelectric couple group 1244-2 to perform the heat absorption operation, and no operating power is applied to the remaining groups 1244-3 and 1244-4. During the second-time period, the forward voltage is applied to the third thermoelectric couple group 1244-3 to perform the heat generating operation, and the reverse voltage is applied to the fourth thermoelectric couple group 1244-4 to perform the heat absorbing operation, and no operating power is applied to the remaining groups 1244-1 and 1244-2. During the third-time period, the reverse voltage is applied to the first thermoelectric couple group 1244-1 to perform the heat absorbing operation, and the forward voltage is applied to the second thermoelectric couple group 1244-2 to perform the heat operation, and no operating power is applied to the remaining groups 1244-3 and 1244-4. During the fourth-time period, the reverse voltage is applied to the third thermoelectric couple group 1244-3 to perform the heat absorbing operation, and the forward voltage is applied to the fourth thermoelectric couple group 1244-4 to perform the heat generating operation, and no operating power is applied to the remaining groups 1244-1 and 1244-2. The above operations during first-time period to the fourth-time period may be repeated.

According to this operation, the feedback device 100 may alternately provide a first thermal grill feedback due to the cooperation of the first thermoelectric couple group 1244-1 and the second thermoelectric couple group 1244-2 and a second thermal grill feedback due to the cooperation of the third thermoelectric couple group 1244-3 and the fourth thermoelectric couple group 1244-4, thereby achieving the same effect as providing the user with continuous thermal grill feedback. The above operations from the first-time period to the second-time period for providing the thermal grill feedback may be repeated.

In the above description related to FIG. 38, it is mentioned that the period of the first thermal grill operation performed by the first and second thermoelectric couple groups 1244-1 and 1244-2, and the period of the second thermal grill operation performed by the third and fourth thermoelectric couple groups 1244-3 and 1244-4 are not overlapped in time. However, the two thermal grill operations may alternatively overlap in time.

Figure 39:
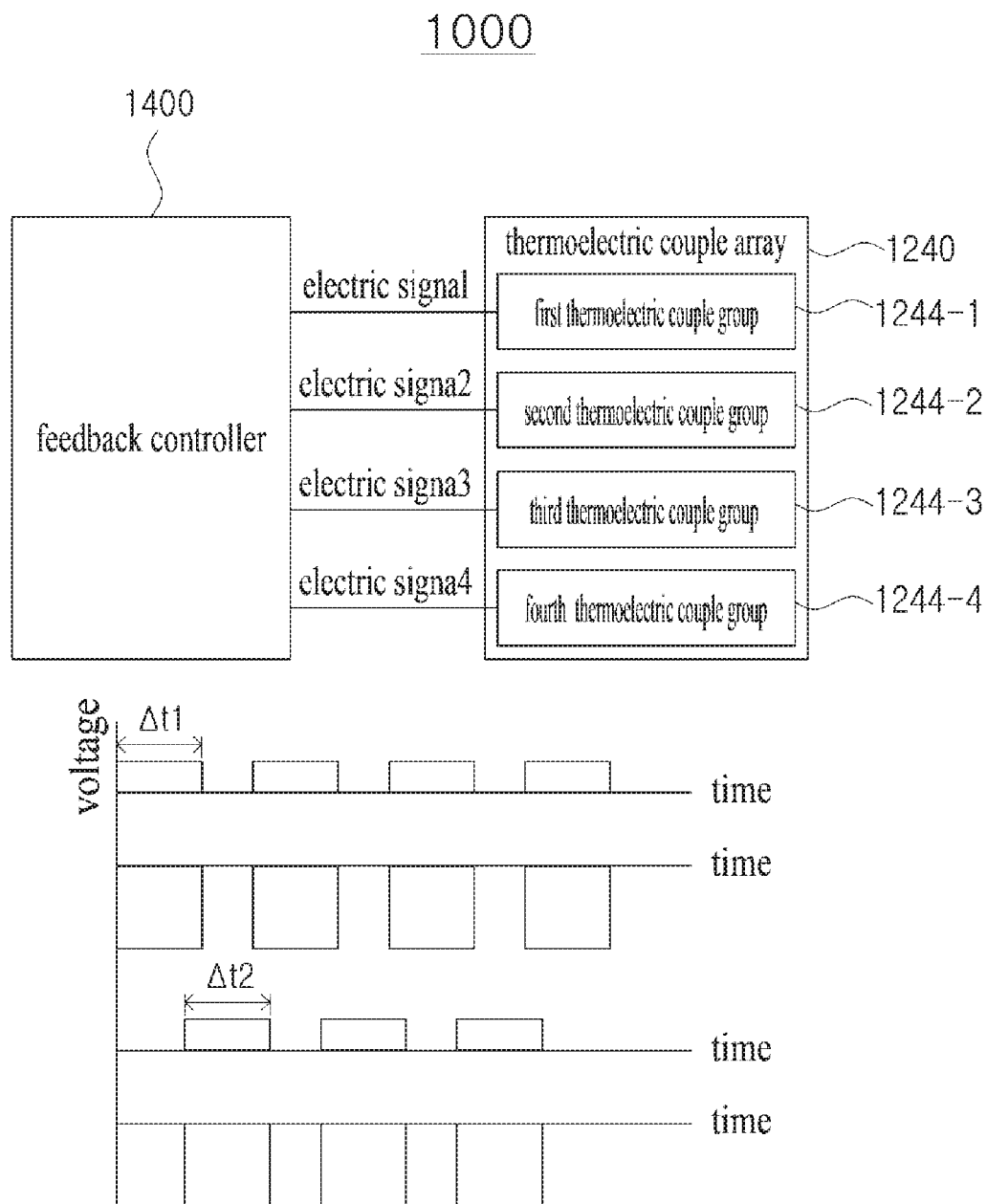
FIG. 39 illustrates yet another example of a thermal grill operation using a combination of an operating area control and an operating time control according to an embodiment of the present disclosure.

FIG. 39 illustrates yet another example of the thermal grill operation using the combination of the operating area control and the operating time control according to an embodiment of the present.

Referring to FIG. 39, the time periods described with reference to FIG. 38 may have an overlapped section. In the overlapped section, the operation of the previous time duration and the operation of the next time duration may be performed together. The thermal grill operation with the overlapped section may reduce or remove the delay time from a time point when the operating power is applied for the heat generating operation and heat absorbing operation to a time point when the temperature of the contact surface 1600 reaches to the saturation temperature so that there is no delay in transmitting the thermal grill feedback to the user.

In addition, the thermal grill feedback operation can be implemented in various ways by combining the operating time control and the operating area control, based upon the examples mentioned in this specification.

2.2. Damage Preventing Operation by Thermal Feedback

The thermal feedback described above stimulates the hot spot and cold spot of the skin, so that it may cause damage to skin or sensory organs when a certain amount of heat is delivered to the user. For example, the skin tissue may be denatured by heat if the user is provided with the thermal feedback of an excessively high intensity, or the sensory organs may be confused if the thermal feedback is continuously provided over a long period of time. Hereinafter, an operation for preventing damage to the user's skin or sensory organs will be described.

According to one embodiment, the voltage value applied by the feedback controller 1400 may be limited so that the temperature change amount caused by the heat outputting module 1200 on the contact surface 1600 does not exceed a certain level. For example, the feedback controller 1400 may limit the forward voltage to fall below a voltage value at which the saturation temperature of the hot feedback is 40° C.

According to another embodiment, the time duration that the thermal feedback is provided may be limited. For example, the feedback controller 1400 may shut off the operating power applied to the heat outputting module 1200 if the thermal feedback is applied continuously for more than a predetermined time.

The limit of the maximum intensity of the thermal feedback may be determined considering the time duration for providing the thermal feedback or the limit of the maximum time duration of the thermal feedback may be determined considering the intensity of the thermal feedback. This is because the physical damage may not occur even if the user is given a long period of weak thermal feedback, while the body damage may occur even in a short period of intense thermal feedback.

For example, in the case of the feedback device 100 capable of applying multiple levels of the thermal feedback, the feedback controller 1400 may obtain the intensity of the thermal feedback, and cut off the operating power applied to the heat outputting module 1200 when the time duration of the thermal feedback exceeds the time limit which is determined based on the obtained intensity.

As another example, when the thermal feedback of various intensity levels is provided to improve the user's perception of the thermal feedback, the feedback device 100 may set a time limit for each intensity level. There may be no time limit for low-intensity thermal feedback in the feedback device 100. A time limit may be set to a predetermined time for mid-intensity and high-intensity thermal feedback. The time limit for the mid intensity thermal feedback may be longer than the time limit for the high intensity thermal feedback. If the thermal feedback needs to be provided beyond the set time limit, the feedback device 100 may provide the thermal feedback until the time limit is reached, and stop outputting the thermal feedback for a rest duration and resume outputting the thermal feedback after the rest duration passed.

2.3. Operation for Preventing Thermal Inversion Illusion

A user who is provided with the thermal feedback using the feedback device 100 may experience a thermal inversion illusion when the thermal feedback terminated. The thermal inversion illusion means an illusionary sensation of the sensory organs that occurs when the given thermal feedback is terminated, and it is felt like the opposite thermal sensation of the terminated thermal sensation. Specifically, when the hot feedback is stopped being provided, the user may instantly feel a cold feeling, and when the cold feedback is stopped being provided, the user may instantly feel a warm feeling. That is, it is a kind of the thermal inversion illusion that the opposite feeling is felt during the process of eliminating the thermal sensation after receiving the specific thermal sensation.

Thermal inversion illusion may hinder the user experience provided with the thermal feedback. For example, if a user grasps a hot kettle within a virtual reality, the feedback device 100, as part of the virtual reality experience system, may provide the hot feedback to the user to improve the user experience for the virtual reality. However, if the user instantly senses the coldness at the end of the thermal feedback, the immersion into the virtual reality may be inhibited.

Hereinafter, the thermal inversion illusion will be described in more detail, and specific methods for preventing thermal inversion illusion will be described.

2.3.1. Causes of Thermal Inversion Illusion

The process for providing the thermal feedback to the user is briefly as follows: First, the feedback controller 1400 applies the operating power to the heat outputting module 1200. The power applied to the heat outputting module 1200 is transmitted to the thermoelectric element through the power terminal 1260. In the thermoelectric element, an exothermic reaction or an endothermic operation occurs due to the Peltier effect. It can be interpreted that the thermoelectric couple array 1240 performs the heat generating operation or the heat absorbing operation, and the hot heat generated by the heat generating operation or the cold heat generated by the heat absorbing operation is transmitted to the user's skin through the contact surface 1600. The heat transmitted to the skin stimulates the hot spot or the cold spot of the skin, and the user can feel the hot sensation when the hot spot is stimulated, the cold sensation when the cold spot is stimulated, or a pain sensation when the both of hot spot and cold spot are stimulated at the same time.

Figure 40:
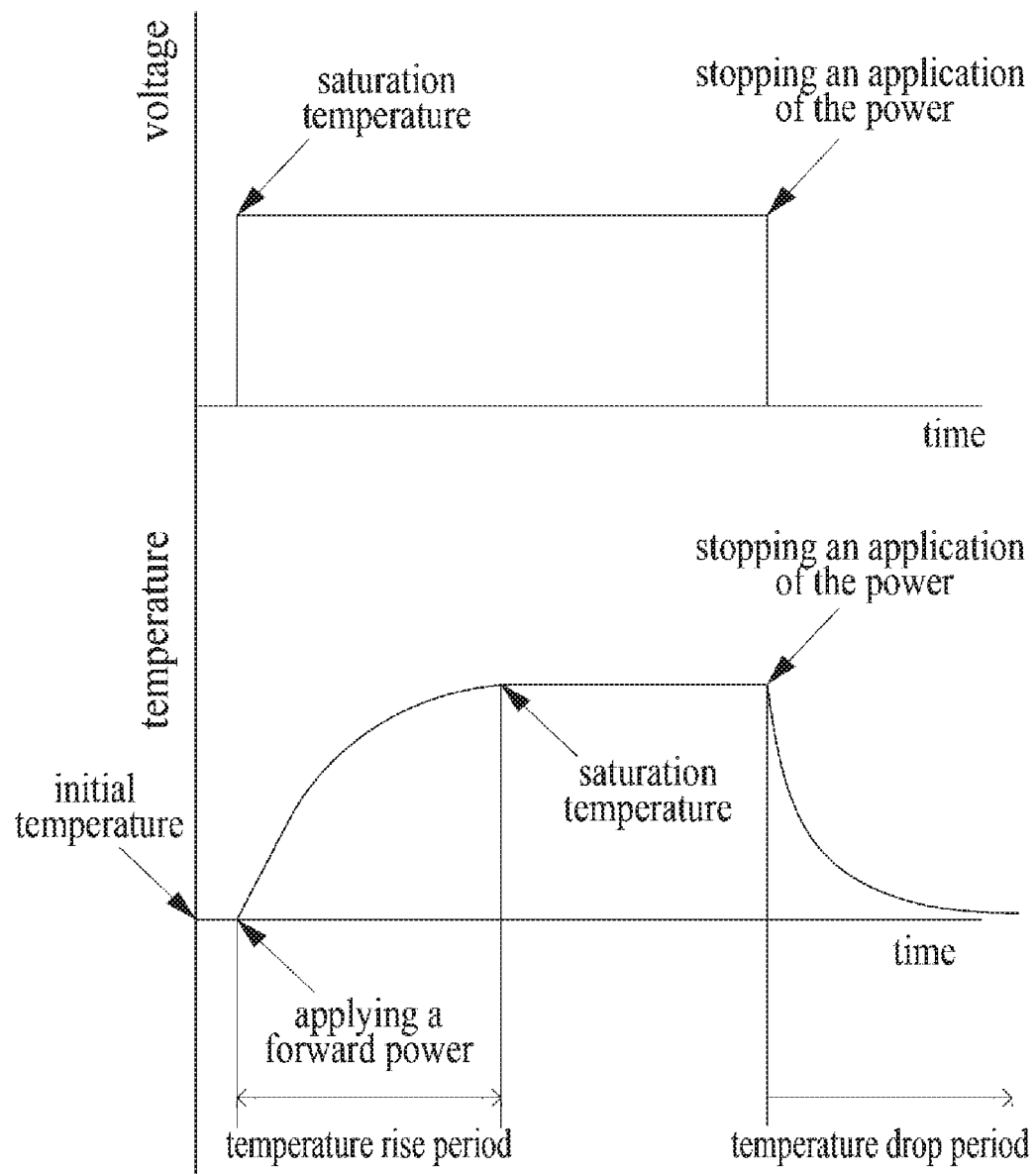
FIG. 40 is a graph showing a temperature change of the contact surface in the heat generating operation according to an embodiment of the present disclosure.

FIG. 40 is a graph showing a temperature change of the contact surface 1600 in the heat generating operation according to an embodiment of the present disclosure.

Referring to FIG. 40, when the heat generating operation or the heat absorbing operation is started as the operating power is applied, the temperature of the contact surface 1600 does not reach to the saturation temperature immediately but changes gradually from the initial temperature to reach the saturation temperature, since the thermoelectric couple array 1240 and the contact surface 1600 have a certain heat capacity. Likewise, when the operating power is cut off to stop the heat generating operation or the heat absorbing operation, the temperature of the contact surface 1600 does not return to the initial temperature immediately but changes gradually from the saturation temperature to the initial temperature.

The thermal inversion illusion may be felt in the process of returning the temperature of the contact surface 1600 to the initial temperature in accordance with the termination of the heat generating operation or the heat absorbing operation.

For example, if the heat generating operation is stopped in the hot feedback state, the temperature of the contact surface 1600 decreases from the saturation temperature to the initial temperature. In this process, the number of hot spots which are stimulated by the hot feedback decreases, and the user feels a cold feeling instantly even though the temperature does not fall below the initial temperature. Conversely, if the heat absorbing operation stopped in the cold feedback state, the temperature increases from the saturation temperature to the initial temperature. In this process, the number of cold spots which are stimulated by the cold feedback decreases and the user feels a hot feeling instantly even though the temperature does not rise above the initial temperature.

Figure 41:
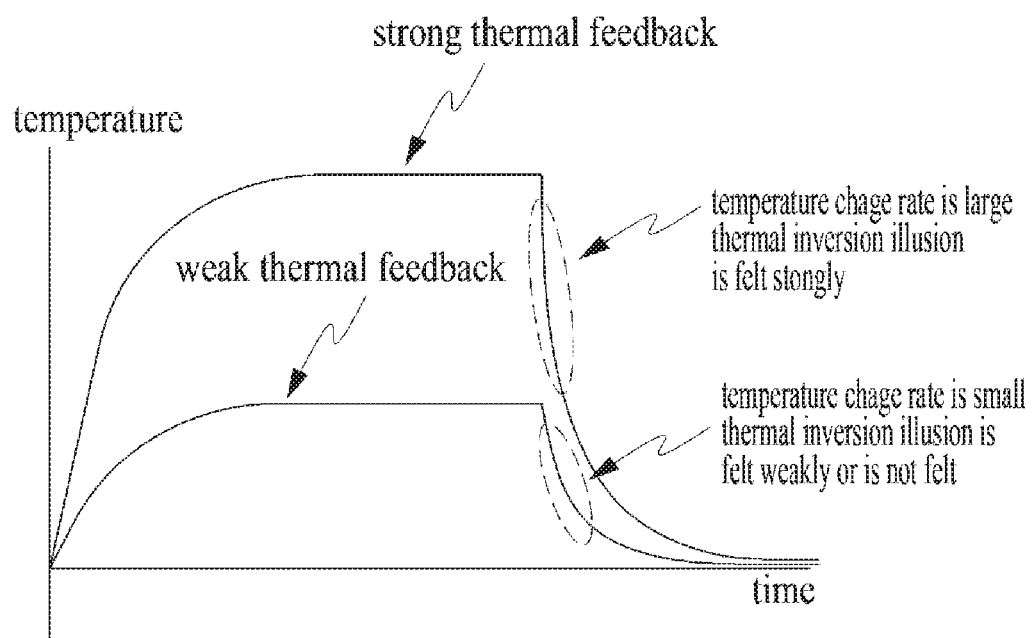
FIG. 41 is a graph showing a thermal inversion illusion according to an embodiment of the present disclosure.

In sum, the thermal inversion illusion is a thermal illusionary sensation that is felt by the user, even though it is not physically given, when the temperature changes due to eliminating the existing thermal feedback, and that is opposite to the eliminated thermal feedback FIG. 41 is a graph showing the thermal inversion illusion according to an embodiment of the present disclosure.

Experimental observation shows that the thermal inversion illusion is stronger as the difference between the saturation temperature and the initial temperature is larger and the rate of temperature change is faster. Specifically, as shown in FIG. 41, when the high-intensity thermal feedback with a large temperature change amount relative to the skin temperature is terminated, the magnitude of the temperature change occurring in the process of the return to the initial temperature is large and the temperature change speed is fast so that the thermal inversion illusion is felt strongly. In contrast, when the low-intensity thermal feedback with a small temperature change relative to the skin temperature is terminated, the temperature change caused by the process is small and the temperature change speed is slow, thus the thermal inversion illusion may not be felt substantially.

2.3.2. Buffering Operation for Preventing Thermal Inversion Illusion

The feedback device 100 may eliminate the thermal inversion illusion by alleviating the rate of temperature change that occurs in the process of returning to the initial temperature upon terminating of the thermal feedback.

Figure 42:
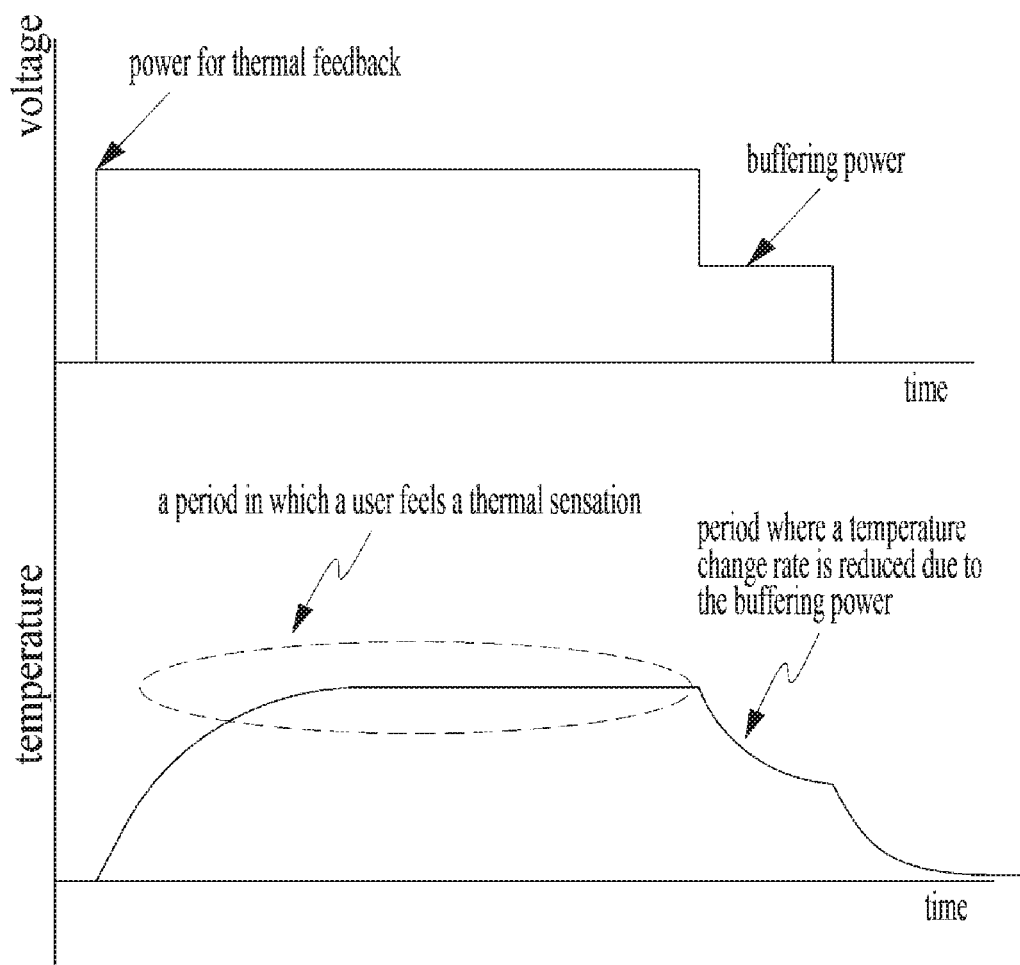
FIG. 42 is a graph showing to a temperature change of the contact surface due to a buffering power according to an embodiment of the present disclosure.

FIG. 42 is a graph showing to the temperature change of the contact surface 1600 due to a buffering power according to an embodiment of the present disclosure.

Referring to FIG. 42, the feedback controller 1400 may apply a buffering power to the heat outputting module 1200 instead of immediately shutting off the operating power when stopping the thermal feedback. Here, the buffering power may have the same current direction as the operating power for the thermal feedback, and the voltage or current magnitude of the buffering power may be smaller than those of the operating power for the thermal feedback. The feedback controller 1400 may apply the buffering power for a predetermined time duration instead of immediately cutting off the power so that the temperature change rate of returning from the saturation temperature to the initial temperature may be reduced. Thus, the thermal inversion illusion can be reduced or eliminated because the temperature is not suddenly changed when the thermal feedback is terminated.

On the other hand, the feedback device 100 may use the buffering power having multi voltage values for the operation for preventing the thermal inversion illusion. Hereinafter, an operation which applies the buffering power is referred to as "buffering operation," and the voltage and current of the buffering power is referred to as "buffering voltage" and "buffering current." Also, the application time of the buffering power or the time duration performing the buffering operation is referred to as "buffering duration."

Figure 43:
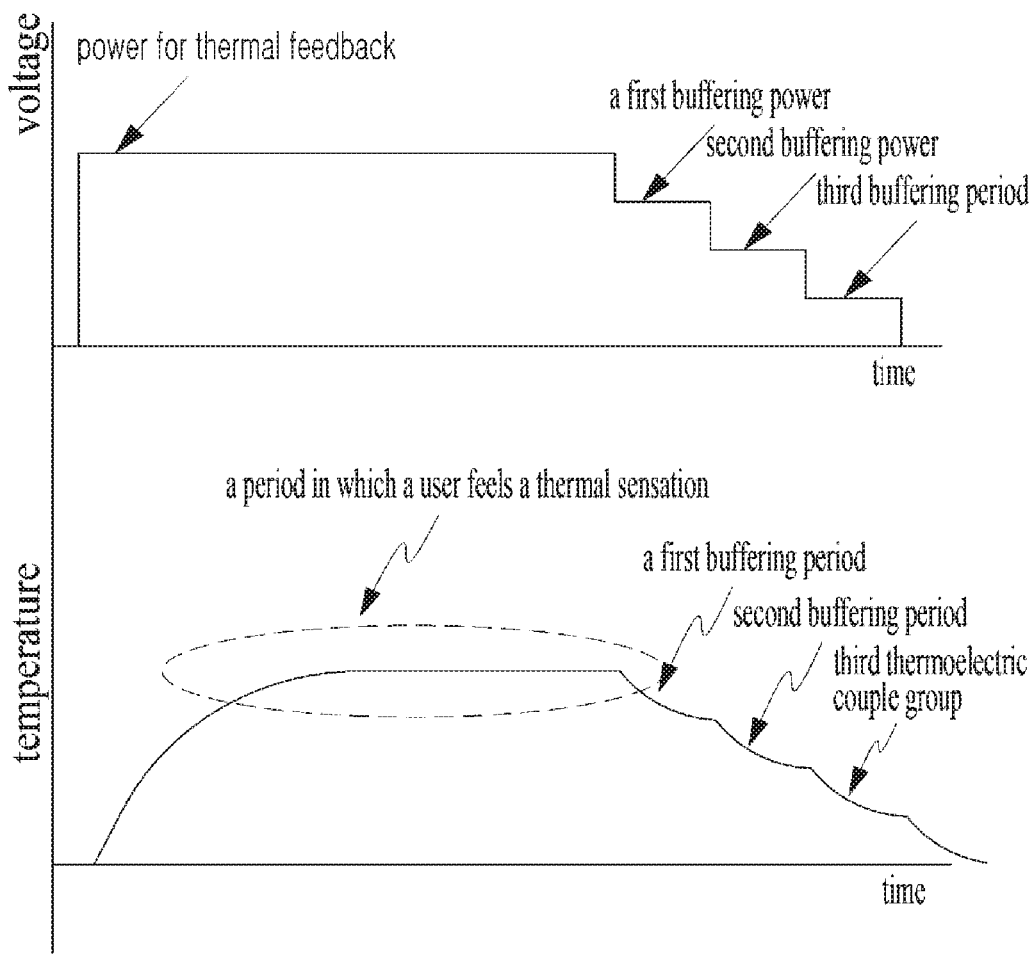
FIG. 43 is a graph showing a temperature change of the contact surface due to a buffering power having multiple voltage values according to an embodiment of the present disclosure.

FIG. 43 is a graph showing to a temperature change of the contact surface 1600 due to a buffering power having multiple voltage values according to an embodiment of the present disclosure.

Referring to FIG. 43, the feedback device 100 may perform the buffering operation using the first, second, and third buffering voltages. Specifically, the feedback controller 1400 may apply the operating voltage, the first buffering voltage, the second buffering voltage, and the third buffering voltage in order, and shut off the power supply when the thermal feedback ends.

In the case of high-intensity thermal feedback, the temperature change may be still relatively abrupt when only a single buffering voltage is used. If the multi-stage buffering voltage is used, the thermal inversion illusion may be removed also for the high-intensity thermal feedback.

In particular, if the feedback device 100 is capable of outputting the thermal feedback at multiple intensity levels, an operating voltage for a lower-level thermal feedback may be used as the buffering voltage for the higher-level thermal feedback.

Also in the above description, the buffering voltage in the buffering operation is described as a constant voltage or a step voltage. However, the buffering voltage may have an electrical signal that gradually decreases with time.

2.3.3. Other Buffering Operation

In the above description, when the operating power applied for the thermal feedback is cut off to terminate the output of the thermal feedback, the buffering power may be applied to prevent the occurrence of the thermal inversion illusion.

However, the PWM signal may also be used as the buffering power for an operation for preventing the thermal inversion illusion, that is, the buffering operation.

For example, the feedback controller 1400 of the feedback device 100 may use a PWM power having a voltage equal to or lower than that of the operating power as the buffering power at the time of cutting off the operating power. Here, when the operating power is a PWM signal, the buffering power may be a PWM signal having a lower duty rate than the operating power.

Or in case that thermoelectric element is implemented as the thermoelectric couple array 1240 having a plurality of individually controllable thermoelectric couple groups 1244, the buffering operation may also be performed by maintaining application of the operating power to smaller numbers of the thermoelectric couple groups 1244 than the thermoelectric couple groups 1244 for outputting the thermal feedback during the buffering duration. For example, in the case of outputting thermal feedback using a thermoelectric couple array 1240 having five thermoelectric couple groups 1244, the buffering operation may be performed by maintaining the operating power for two thermoelectric couple groups 1244 and cutting off the operating power for the remaining three thermoelectric couple groups 1244. That is, the buffering operation is performed according to a manner of gradually reducing the number of the thermoelectric couple groups 1244 performing the thermoelectric operation from the whole thermoelectric couple array 1240.

In the above description, the buffering operation is performed by applying the buffering power in succession to the stoppage of the operating power supply. However, the buffering power may alternatively be applied at a predetermined time after the operation power supply is stopped.

2.3.4. Buffering Operation Considering Intensity of Thermal Feedback

Thermal inversion illusion may be caused only by terminating of relatively strong intensity thermal feedback, and may not be caused by terminating of relatively weak intensity thermal feedback.

Accordingly, when providing the thermal feedback of various intensities, the feedback device 100 may determine whether to perform the buffering operation based on the intensity of the thermal feedback. That is, the feedback device 100 may not perform the operation for preventing the thermal inversion illusion for the weak thermal feedback that is not likely to cause the thermal inversion illusion.

Figure 44:
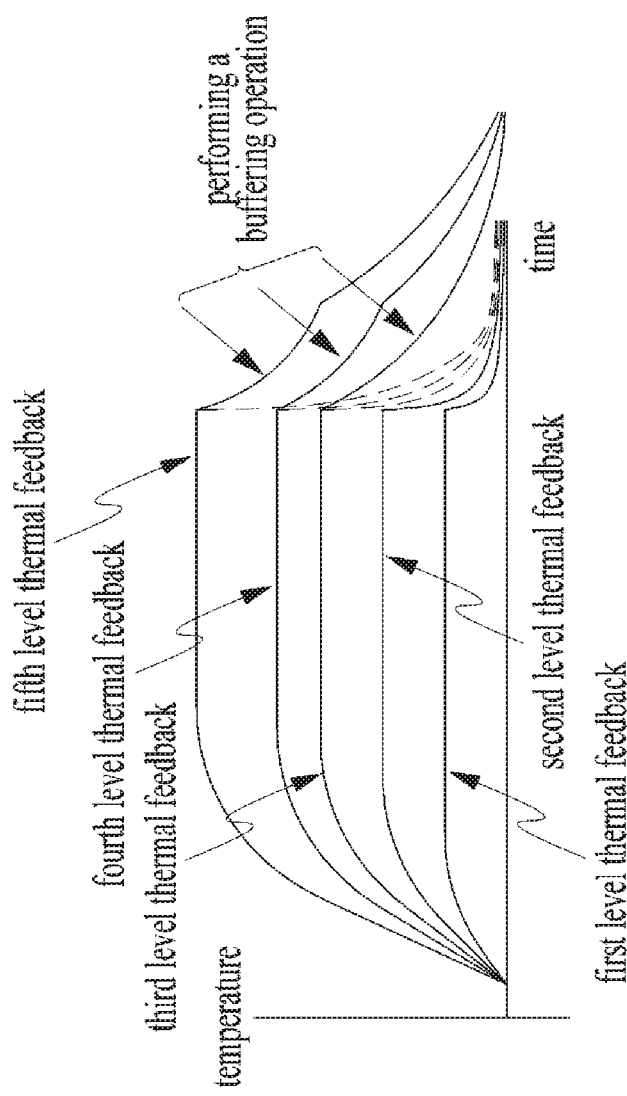
FIG. 44 is a graph showing a temperature change upon a termination of the thermal feedback of various intensities according to an embodiment of the present disclosure.

FIG. 44 is a graph showing a temperature change upon a termination of the thermal feedback of various intensities according to an embodiment of the present disclosure.

Referring to FIG. 44, the feedback device 100 may provide five intensity levels for hot feedback and cold feedback, respectively. Assuming only top three intensity levels of the thermal feedback causes the thermal inversion illusion, the feedback device 100 may perform the buffering operation for the upper three intensity levels and not perform the buffering operation for the remaining lower two intensity levels. Specifically, the feedback controller 1400 may obtain information on the intensity of the thermal feedback, and determine whether the thermal feedback intensity is smaller than a predetermined level. If the intensity of the thermal feedback is smaller than the predetermined level, the feedback controller 1400 may cut off the operating power immediately after terminating the thermal feedback. If the intensity of the thermal feedback is equal to or greater than the predetermined level, the feedback controller 1400 may apply the buffering power for a predetermined time duration after terminating the thermal feedback, and cut off all the power.

When the feedback device 100 provides thermal feedback of multiple intensities, thermal inversion illusion may occur in the higher intensity thermal feedbacks while thermal inversion illusion may not occur in the lower intensity thermal feedbacks. Thus, to prevent thermal inversion illusion, the operating voltage used for the thermal feedback of the lower intensity may be used as the buffering voltage.

The magnitude of the buffering voltage and the time length of the buffering duration during which the buffering power is applied may also be set differently depending on the intensity of the thermal feedback. Thus, feedback device 100 may set the buffering voltage for high-intensity thermal feedback to be greater than the buffering voltage for low-intensity thermal feedback. Similarly, the feedback device 100 may also set the buffering duration for high-intensity thermal feedback to be longer than the buffering duration for low-intensity thermal feedback.

2.3.5. Buffering Operation Considering Type of Thermal Feedback

The above-described thermal inversion illusion may be felt differently in the hot feedback and the cold feedback, even under the same conditions. This is because the temperature change rate due to the stopping of the hot feedback and the temperature change rate due to the stopping of the cold feedback are different from each other.

Figure 45:
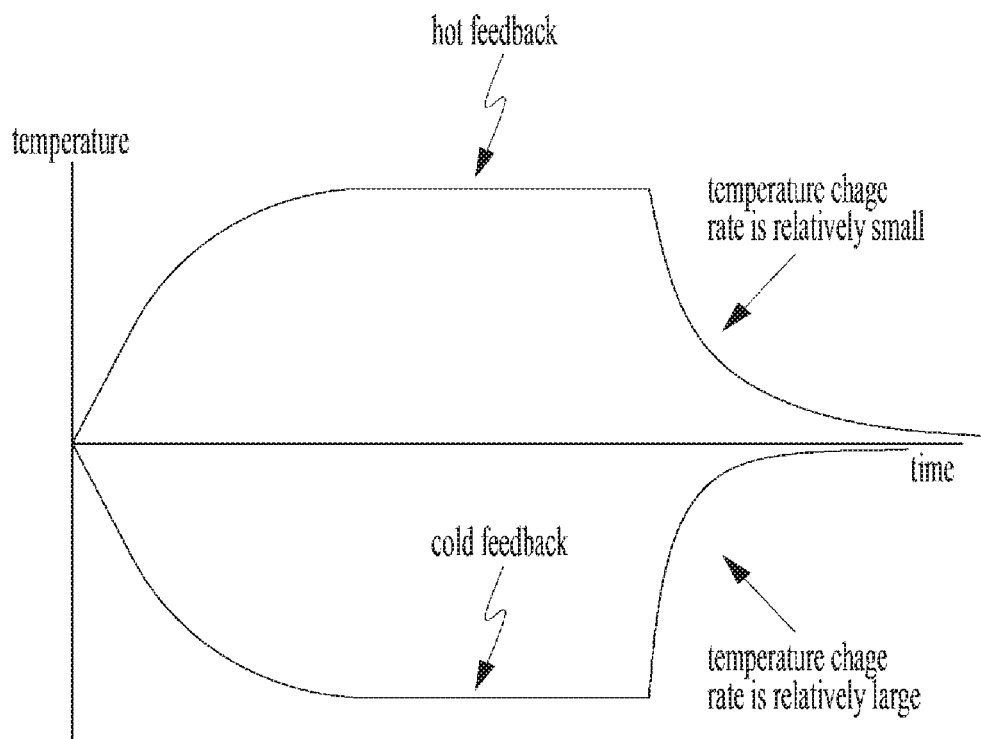
FIG. 45 is a graph showing a difference in temperature change rate between the hot feedback and the cold feedback according to an embodiment of the present disclosure.

FIG. 45 is a graph showing the difference in temperature change rate between the hot feedback and the cold feedback according to an embodiment of the present disclosure.

FIG. 45 shows the temperature drop rate occurring when the hot feedback is stopped is smaller than the temperature rise rate occurring when the cold feedback is stopped.

When electrical energy is applied to the thermoelectric element, some of the electrical energy induces an exothermic reaction and an endothermic reaction, while the rest of the electric energy is converted to waste heat energy. Here, some of the waste heat energy is discharged through a heat sink or the like connected to the thermoelectric element, but a part thereof remains in the thermoelectric element in the form of residual heat. When the supply of electric energy to the thermoelectric element is shut off, the heat generating side and the heat absorbing side are intended to achieve thermal equilibrium by conduction. The temperature change of the contact surface 1600 or the front surface of the thermoelectric couple array 1240 due to the termination of the thermal feedback may have residual heat in addition to the temperature of the rear surface of the thermoelectric couple array 1240. The residual heat acts hinders the temperature drop of the contact surface 1600 or the front surface of the thermoelectric couple array 1240 at the end of the hot feedback. On the contrary, when the cold feedback is stopped, the residual heat acts as a factor for enhancing the temperature rise of the contact surface 1600 or the front surface of the thermoelectric couple array 1240. Therefore, in general, the temperature change rate at the time of stopping the hot feedback is smaller than the temperature change rate at the time of stopping of the cold feedback. Thus, the thermal inversion illusion may be felt more strongly upon termination of the hot feedback, even under the same conditions.

Figure 46:
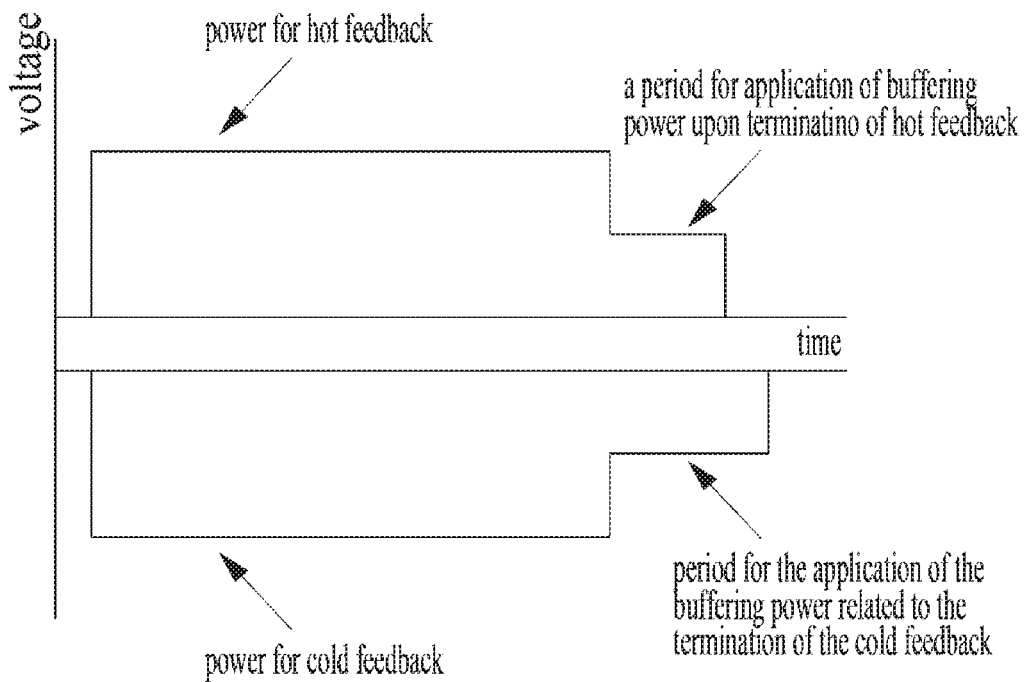
FIG. 46 is a graph showing a difference between the buffering duration at the end of the hot feedback and the cold feedback according to an embodiment of the present disclosure.

Accordingly, the feedback device 100 may process the operation for preventing the thermal inversion illusion differently at the end of the hot feedback and at the end of the cold feedback, FIG. 46 is a graph showing a difference between the buffering duration at the end of the hot feedback and the cold feedback according to an embodiment of the present disclosure.

For example, as shown in FIG. 46, the feedback device 100 may set the time length of the buffering duration of the cold feedback to be longer than the length of the buffering period of the hot feedback. The feedback controller 1400 may obtain the type of the thermal feedback at the end of the thermal feedback, determine the time length of the buffering duration in consideration of the type of the thermal feedback, and apply the buffering power to the heat outputting module 1200 for the determined buffering duration. That is, the feedback controller 1400 determines whether the thermal feedback is hot feedback or cold feedback, sets the buffering duration to the first-time length when the thermal feedback is the hot feedback or to the second-time length longer than the first-time length when the thermal feedback is cold feedback.

The feedback device 100 may determine whether to perform the operation for preventing the thermal inversion illusion based on both the type of the thermal feedback and the intensity of the thermal feedback. For example, in the description of FIG. 44, it is mentioned that the operation for preventing the thermal inversion illusion may be performed only for the hot feedback of the upper three intensity levels among total five intensity levels, and the operation may not be performed for the remaining lower two intensity levels. However, the feedback controller 1400 may perform the buffering operation only for the top two intensity levels of the hot feedback while performing the buffering operation for the top three intensity levels of the cold feedback.

2.3.6. Buffering Operation Upon Termination of Thermal Grill Feedback

In the above description, the thermal inversion illusion is mainly caused by the termination of the hot feedback and the cold feedback. However, a similar phenomena may also occur for the thermal grill feedback.

Figure 47:
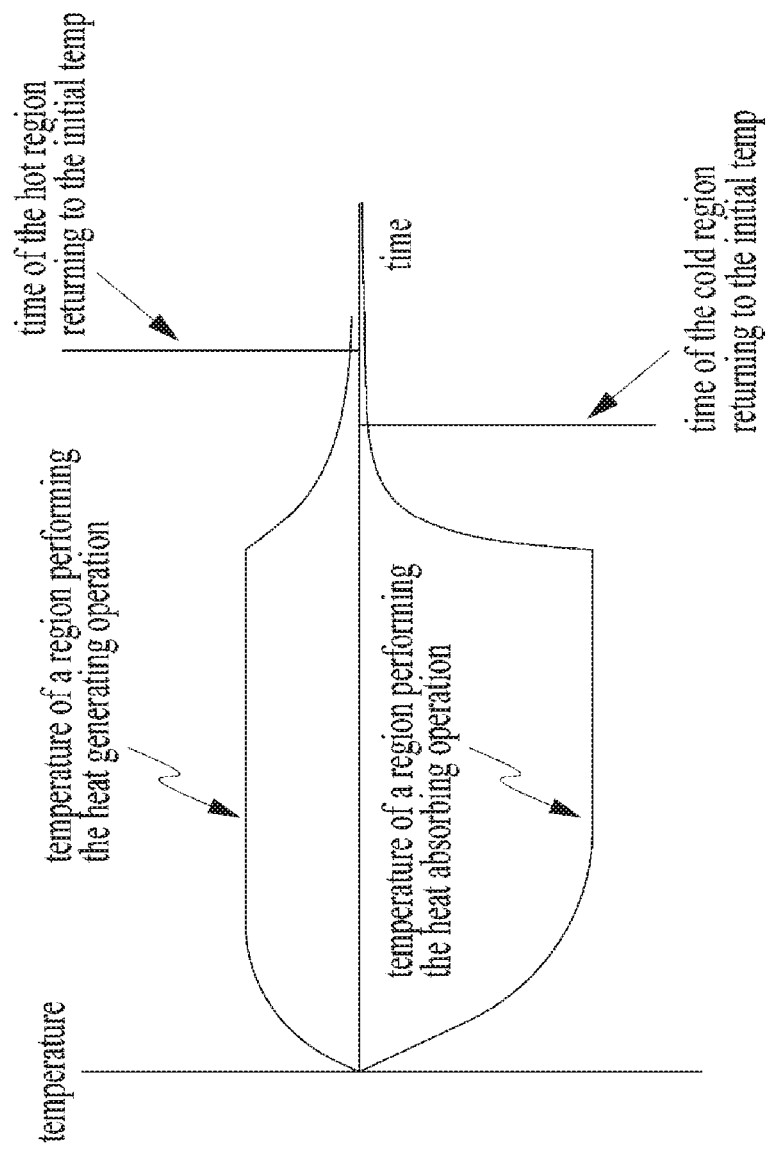
FIG. 47 is a graph showing a temperature change of the contact surface at the end of the thermal grill feedback according to an embodiment of the present disclosure.

FIG. 47 is a graph showing a temperature change of the contact surface 1600 at the end of the thermal grill feedback according to an embodiment of the present disclosure.

Referring to FIG. 47, when the thermal grill feedback provided by performing simultaneously the heat generating operation and the heat absorbing operation is terminated, the portion providing the cold feedback may return the initial temperature earlier than the portion providing the hot feedback. That is, the temperature of the portion providing the hot feedback reaches the initial temperature after the temperature of the portion providing the cold feedback reaches the initial temperature. This may be due to the residual heat as described above. Accordingly, even though the feedback device 100 stops the heat generating operation and the heat absorbing operation at the same time, the user may feel unintended warmth at the end of the neutral grill feedback.

Figure 48:
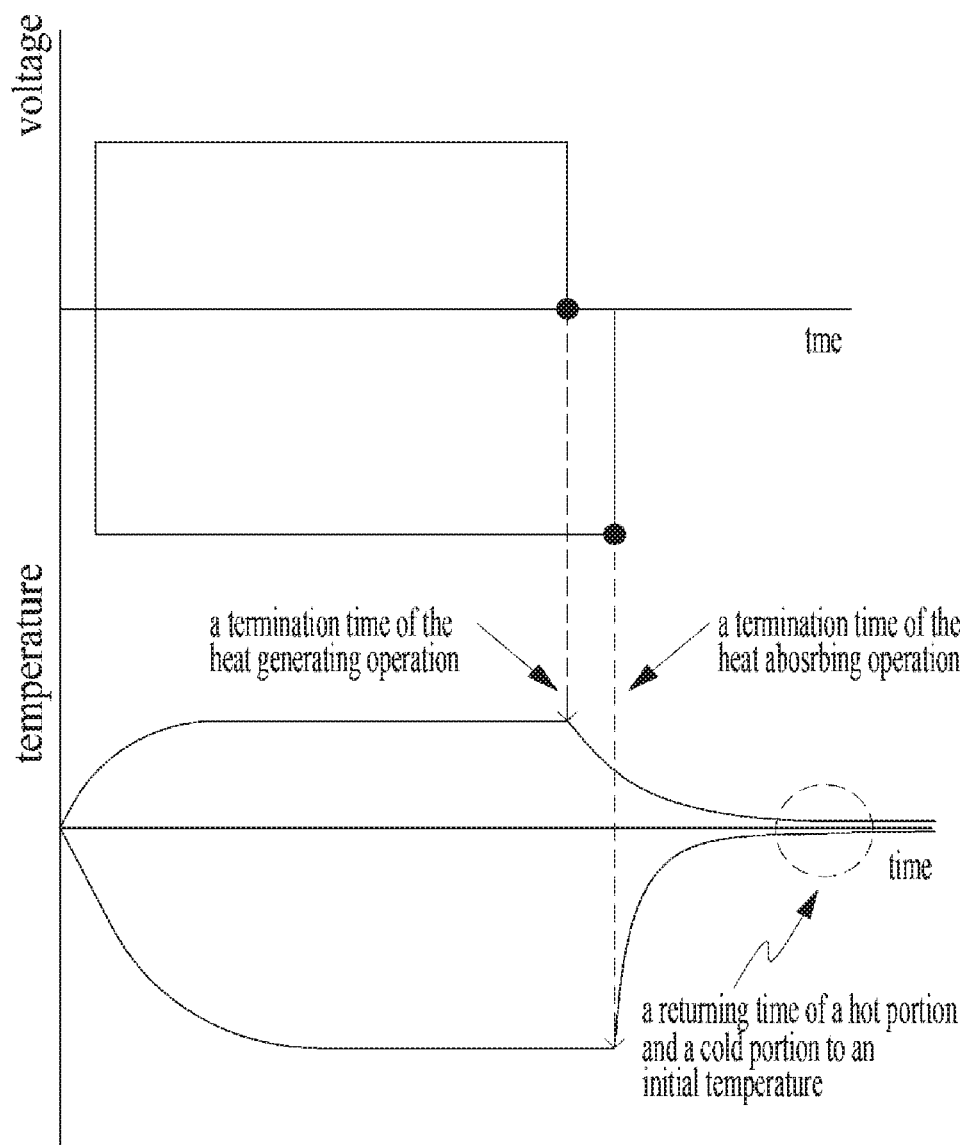
FIG. 48 is a graph showing an operation for eliminating warmth at the end of the thermal grill feedback according to an embodiment of the present disclosure.

FIG. 48 is a graph showing an operation for eliminating warmth at the end of the thermal grill feedback according to an embodiment of the present disclosure.

Accordingly, the feedback device 100 may eliminate the feeling of warmth felt at the end of the thermal grill feedback by postponing the end of the heat absorbing operation to after the end of the heat generating operation when the heat generating operation and the heat absorbing operation are stopped to terminate the thermal grill feedback. Specifically, the feedback controller 1400 may apply the forward voltage to heat outputting module 1200 up to a first time point and apply the reverse voltage up to a second time point later than the first time point to eliminate the feeling of warmth which is felt at the end of the thermal grill feedback.

However, when the neutral grill feedback is terminated, there may be a case where a feeling of coolness is felt instead of warmth. The neutral grill feedback may be output when the ratio of the temperature due to the heat generating operation and the heat absorbing operation is the neutral ratio. According to the neutral ratio, the temperature change amount with respect to the initial temperature is larger at the heat absorbing operation than at the heat generating operation.

Specifically, in case that the neutral ratio is about 2.5, when the neutral grill feedback ends, the temperature of the hot portion of the contact surface 1600 may reach the initial temperature first and the temperature of the cold portion of the contact surface 1600 may reach the initial temperature later. When the feedback device 100 stops the heat generating operation and the heat absorbing operation for terminating the thermal grill feedback, the feedback device 100 may stop the heat absorbing operation earlier than the heat generating operation.

Specifically, when the thermal grill feedback ends, the feedback controller 1400 may apply the reverse voltage to the heat outputting module 1200 up to a first-time point, and apply the forward voltage up to a second time point later than the first time point to reduce or eliminate the cold feeling which may otherwise be felt at the end of the thermal grill feedback.

Here, it is described that the user feels cold feeling during the period from after the temperature of the heat generating portion reaches the initial temperature to before the temperature of the heat absorption portion reaches the initial temperature. However, because the temperature change rate of the heat absorbing portion is faster than the temperature change rate of the heat generation portion, the user may feel warmth rather than coldness at the end of the thermal grill feedback. When stopping the heat generating operation and the heat absorbing operation to terminate the thermal grill feedback, the feedback device 100 may eliminate the feeling of warmth which is felt at the end of the thermal grill feedback by setting the end time of the heat generating operation to be after the end time of the heat absorbing operation.

Alternatively, the buffering operation may be performed at the end of the thermal grill feedback to prevent the thermal inversion illusion from being felt by the temperature change due to the end of the heat generating operation or heat absorbing operation. Since this has already been described above in detail, a detailed description thereof will be omitted.

2.4. Heat Moving Operation

Hereinafter, a heat moving operation will be described. Here, the heat moving operation is an operation for moving a hot or cold area in the contact surface 1600, which may be performed using the heat outputting module 1200 composed of a plurality of individually controllable thermoelectric couple groups 1244.

Figure 49:
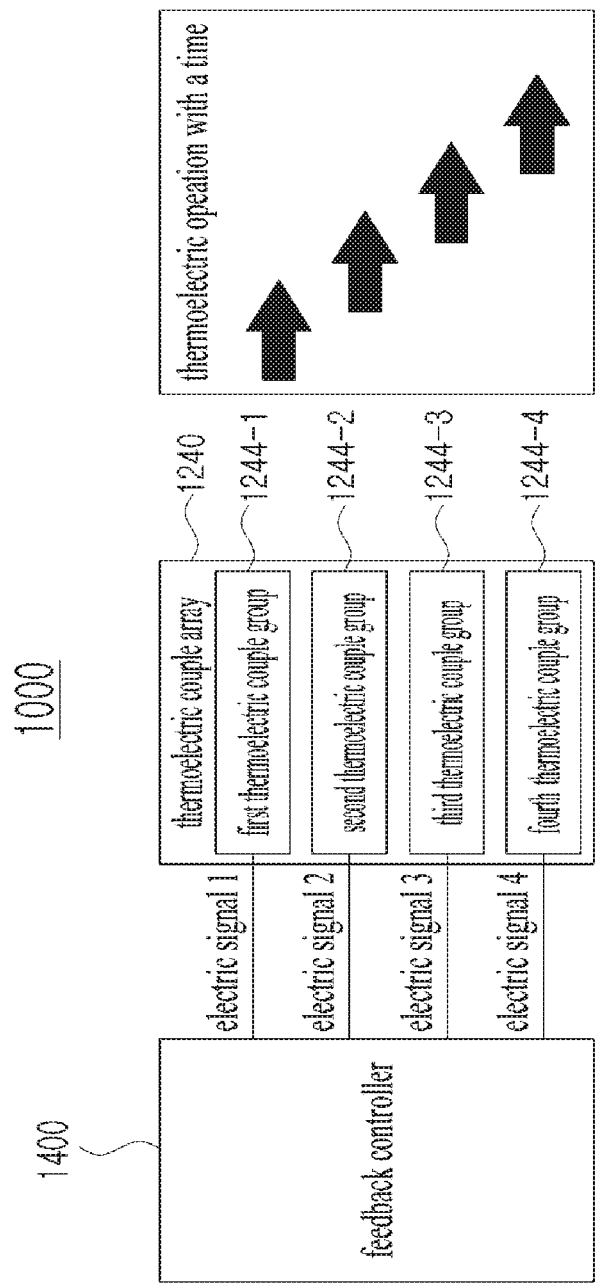
FIG. 49 is a diagram illustrating an example of a heat moving operation according to an embodiment of the present disclosure
Figure 50:
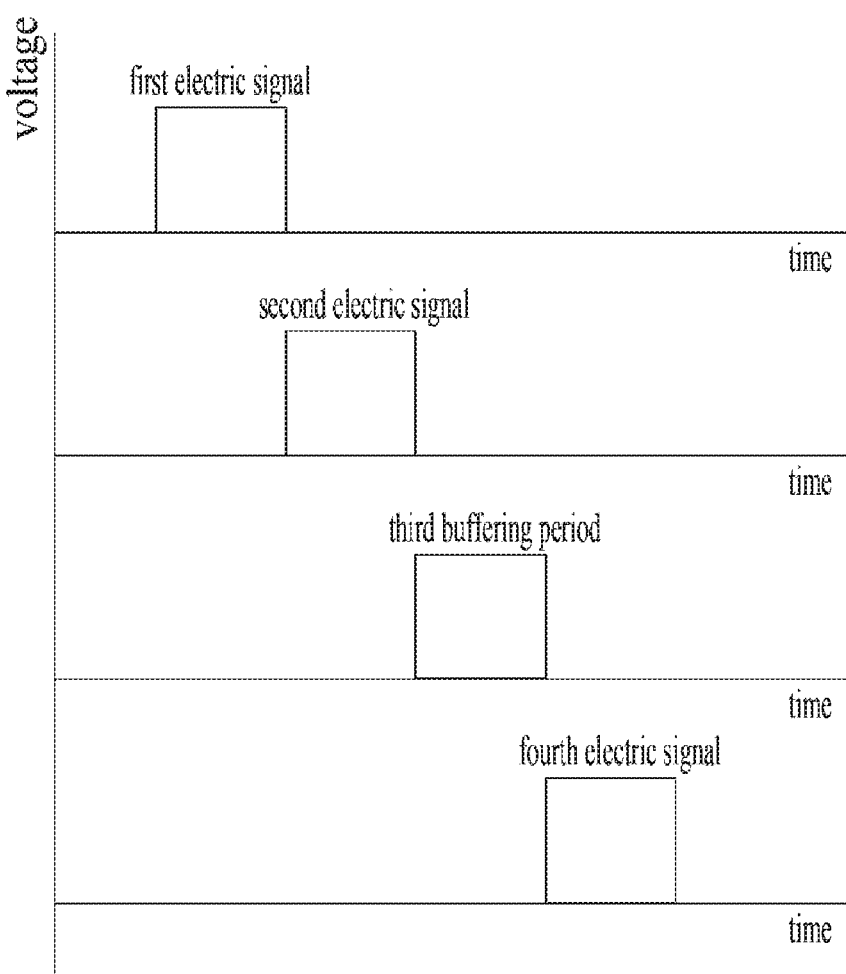
FIG. 50 illustrates an example of an electric signal for the heat moving operation according to FIG. 49.

FIG. 49 is a diagram illustrating an example of a heat moving operation according to an embodiment of the present disclosure, and FIG. 50 illustrates an example of an electric signal for the heat moving operation according to FIG. 49.

Referring to FIGS. 49 and 50, the heat outputting module 1200 may include a first thermoelectric couple group 1244-1, a second thermoelectric couple group 1244-2, a third thermoelectric couple group 1244-3, and a fourth thermoelectric couple group 1244-4.

The feedback controller 1400 may sequentially apply the operating power to the thermoelectric couple groups. Accordingly, the first thermoelectric couple group 1244-1 may first perform a thermoelectric operation (where the thermoelectric operation includes the heat generating operation, the heat absorbing operation, and a thermal grill operation). The second thermoelectric couple groups 1244-2, third thermoelectric couple groups 1244-3, and fourth thermoelectric couple groups 1244-4 may perform the thermoelectric operation in this order.

In addition, the feedback controller 1400 may cut off the operating power to one thermoelectric couple group 1244 at the start time of the application of the operating power to another thermopile group 1244 next to the one thermoelectric couple group. Accordingly, the first thermoelectric couple group 1244-1 may stop the thermoelectric operation when the second thermoelectric couple group 1244-2 starts the thermoelectric operation, and the second thermoelectric couple group 1244-3 may stop the thermoelectric operation when the thermoelectric couple group 1244-3 starts thermoelectric operation, the thermoelectric conversion group 1244-3 may stop thermoelectric operation when the thermoelectric couple group 1244-4 starts thermoelectric operation.

Thus, the user can feel the heat moving from the area where the first thermoelectric couple group 1244-1 is arranged to the area where the fourth thermoelectric couple group 1244-4 is arranged on the contact surface 1600.

The above-described example may be utilized as follows.

For example, when the plurality of thermoelectric couple groups are arranged in the horizontal direction while the feedback device is grasped by the user, the cold heat is moved from one side to the other side so that the user may be provided with a feeling of a cool wind passing. Also, moving the hot heat can provide a feeling of passing the heat source.

Figure 51:
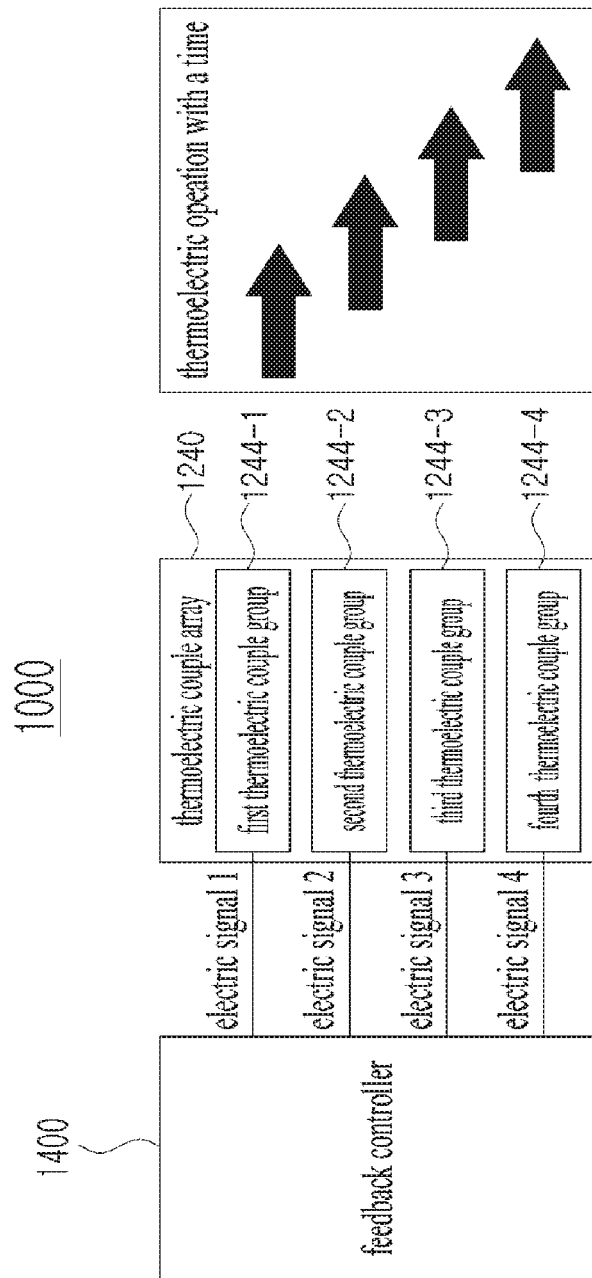
FIG. 51 is a diagram illustrating another example of the heat moving operation according to an embodiment of the present disclosure.
Figure 52:
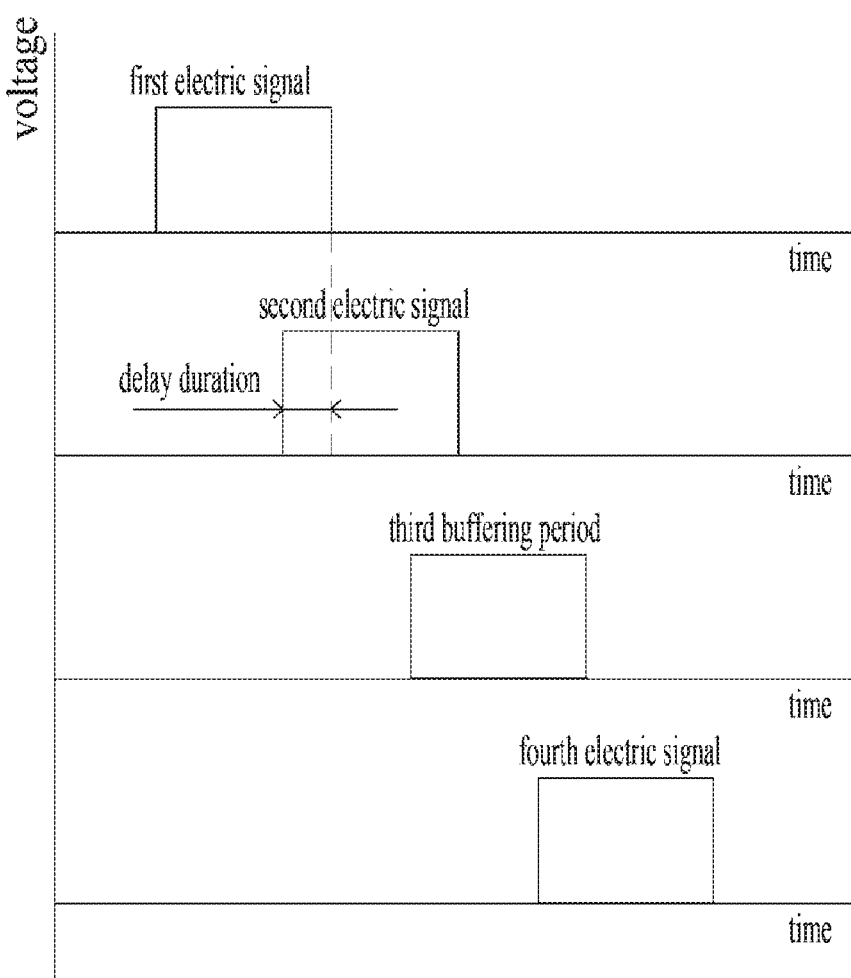
FIG. 52 illustrates an example of an electric signal for the heat moving operation according to FIG. 51.

FIG. 51 is a diagram illustrating another example of the heat moving operation according to an embodiment of the present disclosure, and FIG. 52 illustrates an example of an electric signal for the heat moving operation according to FIG. 51.

FIGS. 51 and 52, the heat outputting module 1200 may include a first thermoelectric couple group 1244-1, a second thermoelectric couple group 1244-2, a third thermoelectric couple group 1244-3, and fourth thermoelectric couple group 1244-4.

Here, the feedback controller 1400 may sequentially apply the operating power to the thermoelectric couple groups 1244. Accordingly, the first thermoelectric couple group 1244-1 may perform the thermoelectric operation first. The second, third, and fourth thermoelectric couple groups 1244-2, 1244-3, and 1244-4 may perform the thermoelectric operation in this order.

Also, the feedback controller 1400 may cut off the operating power to the specific thermoelectric couple group after a predetermined time from when the power is applied to the thermoelectric couple group 1244 which is positioned next to the specific thermoelectric couple group. Accordingly, when the thermal sensation by the first thermoelectric couple group 1244-1 is terminated, the user may sense the heat sensation by the second thermoelectric couple group 1244-2. Similarly, when the thermal sensation by the second thermoelectric couple group 1244-2 is terminated, the user may sense the heat sensation by the third thermoelectric couple group 1244-3, and when the thermal sensation by the third thermoelectric couple group 1244-3 is terminated, the user may sense the heat sensation by the fourth thermoelectric couple group 1244-3.

This considers the time period in which the contact surface reaches a temperature at which the user feels a sense of heat from the time when the operating power is applied to the thermoelectric couple group. Here, the predetermined time may correspond to a delay time until the temperature of the contact surface reaches a temperature enough for user to feel the heat after power is applied to the thermoelectric element.

Accordingly, the user can feel the heat movement from the area where the first thermoelectric couple group 1244-1 is arranged to the area where the fourth thermoelectric couple group 1244-4 is arranged on the contact surface.

Figure 53:
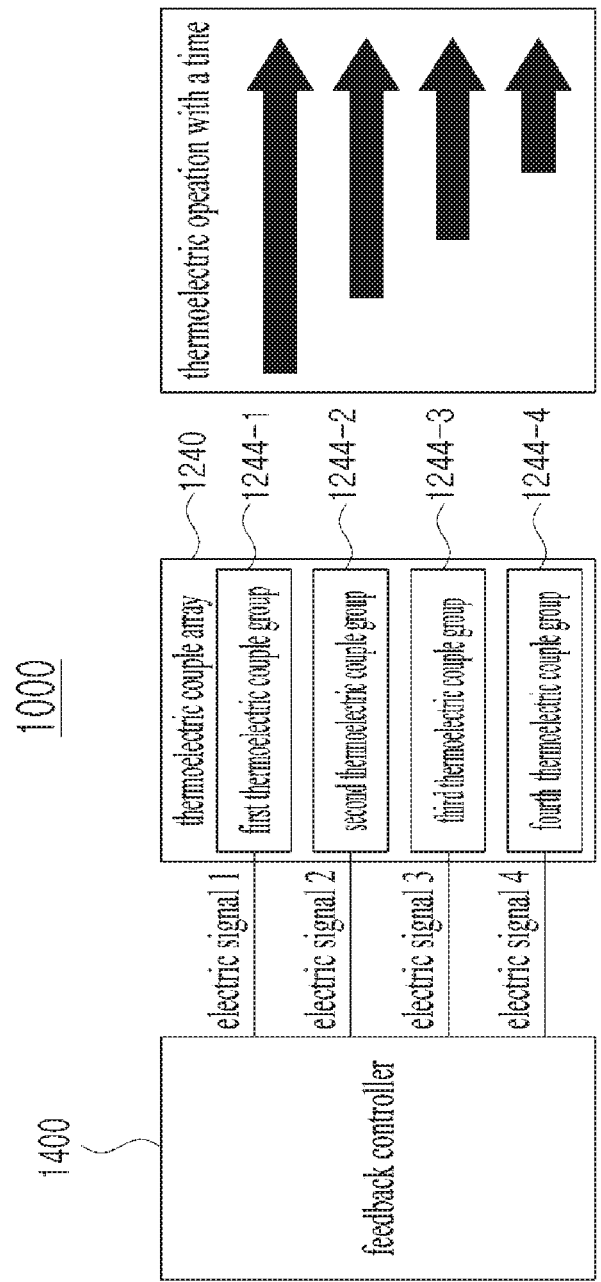
FIG. 53 is a diagram illustrating yet another example of the heat moving operation according to an embodiment of the present disclosure.
Figure 54:
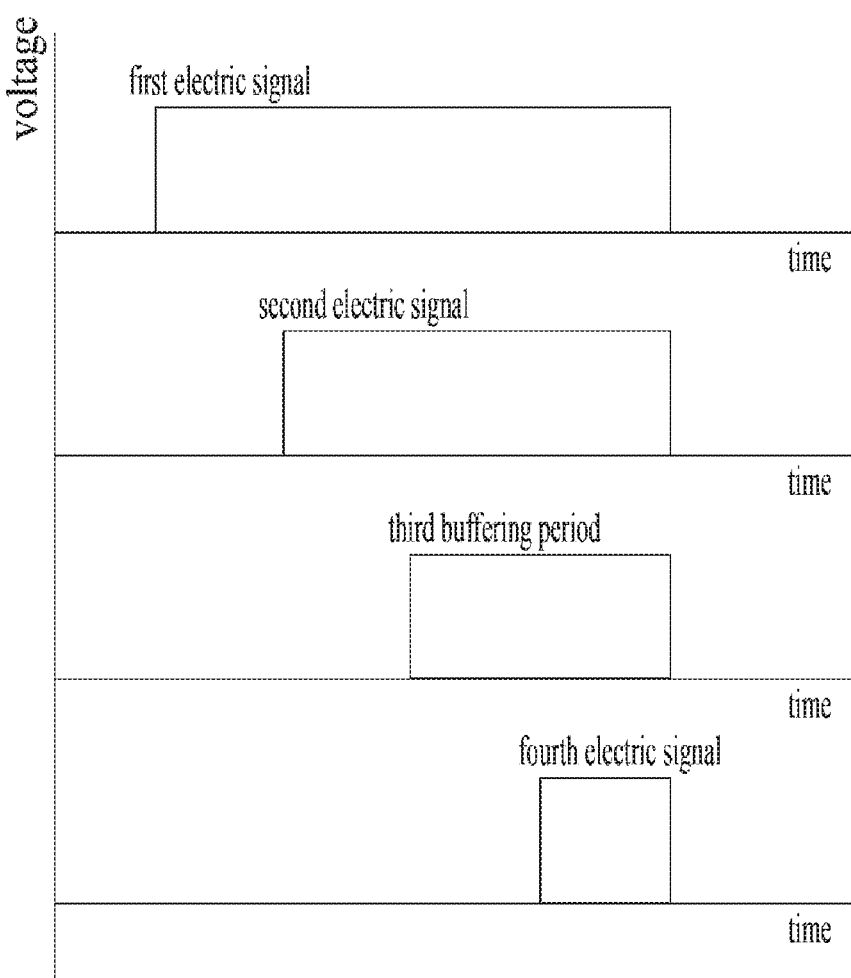
FIG. 54 illustrates an example of an electric signal for the heat moving operation according to FIG. 53.

FIG. 53 is a diagram illustrating yet another example of the heat moving operation according to an embodiment of the present disclosure, and FIG. 54 illustrates an example of an electric signal for the heat moving operation according to FIG. 53.

FIGS. 53 and 54, the heat outputting module 1200 may include a first thermoelectric couple group 1244-1, a second thermoelectric couple group 1244-2, a third thermoelectric couple group 1244-3, 4 thermoelectric couple group 1244-4.

The feedback controller 1400 may sequentially apply the operating power to the thermoelectric couple groups 1244. Accordingly, the first thermoelectric couple group 1244-1 may perform the thermoelectric operation first. The second, third, and fourth thermoelectric couple groups 1244-2, 1244-3, and 1244-4 may perform the thermoelectric operation in this order.

In the other hand, the feedback controller 1400 may not turn off the power for the thermoelectric elements to which the power is applied. Accordingly, the user can feel that the feedback area on the contact surface increases from a region where the first thermoelectric couple group 1244-1 is arranged to the region where the fourth thermoelectric couple group 1244-4 is arranged.

The above-described example may be utilized as follows.

For example, when the plurality of thermoelectric couple groups are arranged in the vertical direction while the feedback device is grasped by the user, the cool region is increased sequentially from lower side to the upper side so that the user may be provided with a feeling of soaking the body in cold water from below.

Figure 55:
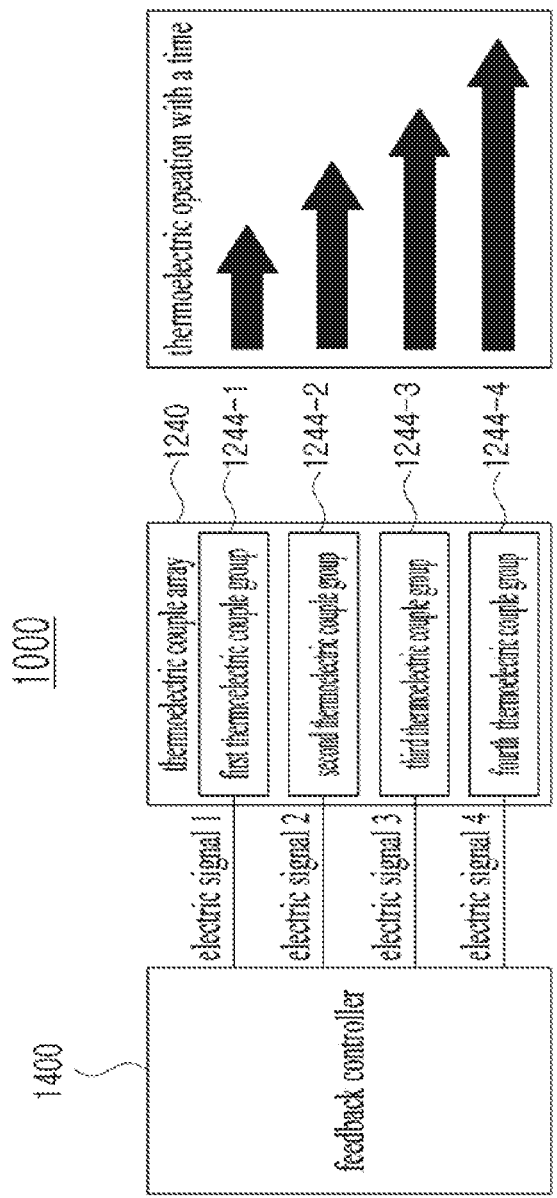
FIG. 55 is a diagram illustrating still another example of the heat moving operation according to an embodiment of the present disclosure.
Figure 56:
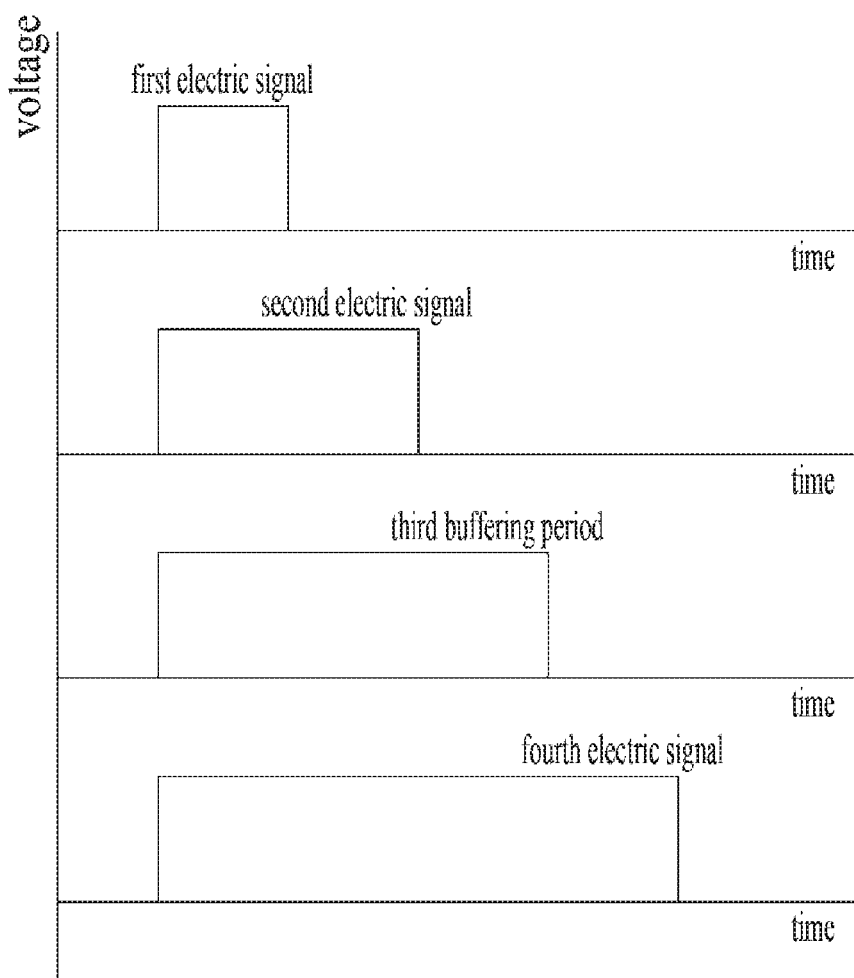
FIG. 56 illustrates an example of an electric signal for the heat moving operation according to FIG. 55.

FIG. 55 is a diagram illustrating still another example of the heat moving operation according to an embodiment of the present disclosure, and FIG. 56 illustrates an example of an electric signal for the heat moving operation according to FIG. 55.

FIGS. 55 and 56, the heat outputting module 1200 includes a first thermoelectric couple group 1244-1, a second thermoelectric couple group 1244-2, a third thermoelectric couple group 1244-3, a fourth thermoelectric couple group 1244-4.

Here, all the thermoelectric couple groups 1244 may be in a state in which the operating power is applied to perform thermoelectric operation. In this state, the feedback controller 1400 may turn off the power to the thermoelectric couple groups 1244 in order. Accordingly, the first thermoelectric couple group 1244-1 first stops the thermoelectric operation, and the thermoelectric operation is stopped in the order of the second, third and fourth thermoelectric couple groups 1244-2, 1244-3 and 1244-4.

Accordingly, the user may feel the heat disappearing from the region where the first thermoelectric couple group 1244-1 is disposed to the region where the fourth thermoelectric couple 1244-4 is disposed.

The above-described example can be utilized as follows.

For example, when the plurality of thermoelectric couple groups are arranged in the vertical direction while the feedback device is grasped by the user, the cool region is decreased from upper side to the lower side so that the user may be provided with a feeling of getting out of cold water from below.

In the example of the above-described heat moving operation, the four thermoelectric couple groups 1244 are arranged in a one-dimensional array. However, the heat moving operation according to the present disclosure is not limited to the above example.

3. Providing Thermal Feedback

Hereinafter, a method for providing the thermal feedback according to an embodiment of the present disclosure will be described. The method for providing the thermal feedback will be described using the feedback device 100 and the operation of the feedback device 100 described above. However, it should be noted that this is merely to facilitate explanations, and the method for providing the thermal feedback is not limited by the feedback device 100 and the operation of feedback device 100.

In the following description, the feedback device 100 is described as being in the form of the gaming controller 100*a*. It should be noted, however, that the feedback device 100 performing the method for providing the thermal feedback is not limited to the gaming controller 100*a*, and other types of feedback device 100 may be used.

3.1. Method for Initiating and Terminating Thermal Feedback

Figure 57:
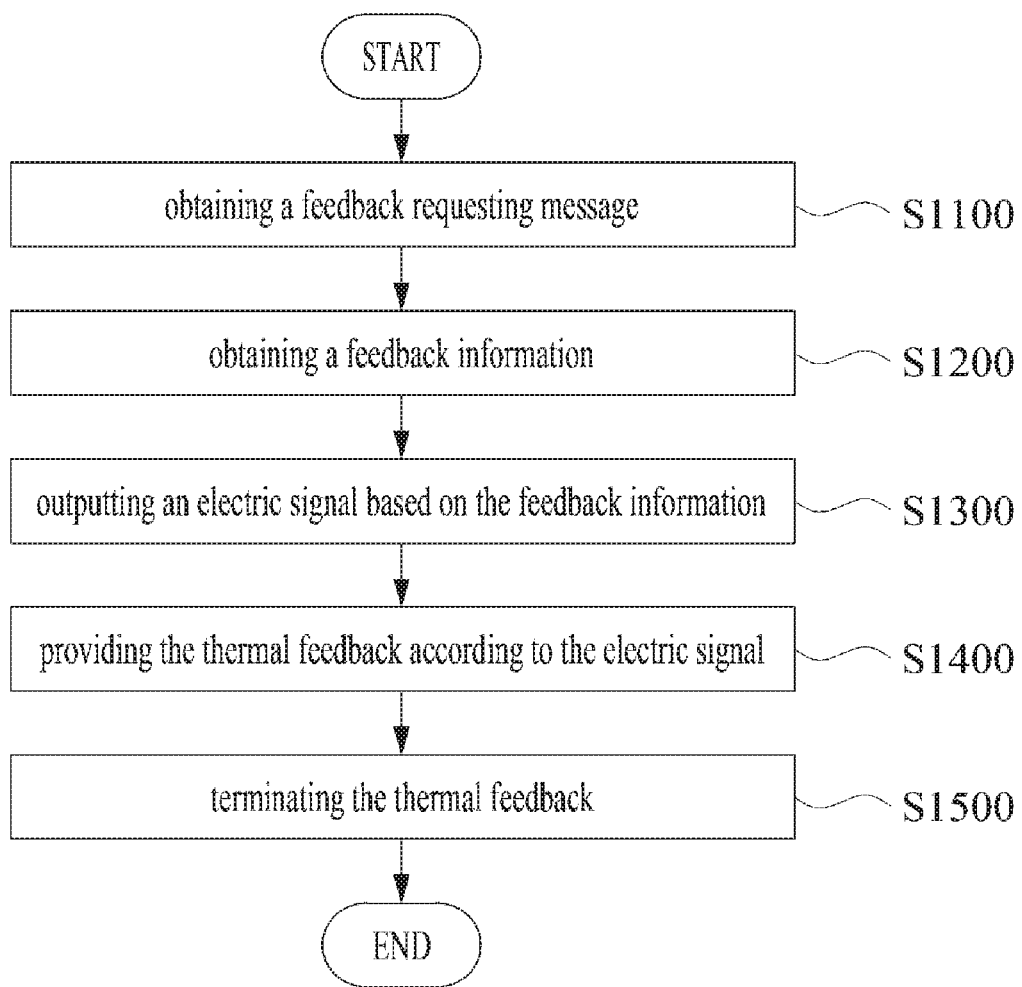
FIG. 57 is a flowchart illustrating a first example of a method for providing the thermal feedback according to an embodiment of the present disclosure.

FIG. 57 is a flowchart illustrating a first example of a method for providing the thermal feedback according to an embodiment of the present disclosure.

Here, the first example of the method for providing the thermal feedback is related to initiating and terminating the thermal feedback.

Referring to FIG. 57, the method for providing the thermal feedback may comprise: obtaining a feedback request message (S1100), obtaining feedback information (S1200), outputting an electrical signal based on the feedback information (S1300), providing the thermal feedback in accordance with the electrical signal (S1400), and terminating the thermal feedback in accordance with the feedback termination message (S1500).

Hereinafter, each of the above-described steps will be described in more detail.

First, the feedback request message may be obtained (S1100). For example, the game console may generate the feedback request message according to the information processing result in the game, and transmit the feedback request message to the feedback device 100. In the feedback device 100, the application controller 2700 may receive the feedback request message via the communication module 2500.

Here, in case that the feedback device 100 is a standalone type, the feedback device 100 itself may acquire the feedback request message. In some embodiments, the application controller 2700 may receive the feedback request message in the form of a user input via the input module 2200. For example, the thermal feedback may be triggered when the user pushes a button on feedback device 100. In other embodiments, the application controller 2700 may obtain the feedback request message when the sensor module detects a specific condition.

When the feedback request message is obtained, the feedback information may be obtained (S1200). Here, the feedback information may include information on the type of the thermal feedback, the intensity of the thermal feedback and the application time of the thermal feedback. Here, the application time may include at least one of a start time of the thermal feedback, an end time of the thermal feedback and a time duration of the thermal feedback. Such information may directly include data on the type, intensity and time duration of the thermal feedback, but may indirectly include data on the type, intensity and time of the thermal feedback.

In one example, the feedback request message may include the feedback information. Thus, the feedback request message received from the game console includes the feedback information, so that the application controller 2700 may obtain the feedback information by extracting it from the feedback request message.

In another example, the feedback information is stored in the memory 2600, and the feedback request message may include an identifier which is used for obtaining the feedback information stored in the memory 2600. Thus, the game controller may extract the identifier from the received feedback request message and obtain the feedback information corresponding to the received feedback request message from the feedback information table stored in the memory 2600 by using the extracted identifier.

In another example, the feedback request message may simply request the initiation of the thermal feedback, and the application controller 2700 may load the pre-stored feedback information from the memory 2600 according to the feedback request message.

An electric signal may be output based on the feedback information (S1300). The application controller 2700 may transmit the feedback information to the feedback controller 1400. The feedback controller 1400 may generate an electric signal to be applied to the heat outputting module 1200 based on the feedback information.

The feedback controller 1400 may determine the current direction of the electric signal, that is, the operating power based on the type of the thermal feedback. When the thermal feedback is a hot feedback, the feedback controller 1400 determines that the current direction of the operating power is a forward direction, and when the thermal feedback is a cold feedback, it is determined that the current direction of the operating power is a reverse direction. In the case of the thermal grill feedback, the feedback controller 1400 may decide to apply the forward power and the reverse power simultaneously or alternately.

Also, the feedback controller 1400 may determine the magnitude of the operating voltage or operating current based on the intensity of the thermal feedback. A voltage table or a current value table relating to the magnitude of the voltage or current according to the intensity of the thermal feedback may be stored in the memory 2600. The feedback controller 1400 may determine the magnitude of the voltage or current to be applied based on the voltage/current table considering the intensity of the thermal feedback. On the other hand, since the magnitude of the operating voltage or operating current may be set differently according to the type of the thermal feedback, the feedback controller 1400 may consider the type of the thermal feedback when referring to the voltage table.

Also, the feedback controller 1400 may determine the period of time to apply the operating power, that is, the application duration based on the time information included in the feedback information.

Once the current direction, the magnitude of the operating power, and the application time are determined, the feedback controller 1400 may apply the electrical signal corresponding to the determined result to the heat outputting module 1200.

The heat outputting module 1200 may receive the electrical signal through the power terminal 1260, and thus the thermoelectric couple array 1240 may perform the heat generating operation, the heat absorbing operation, or the thermal grill operation according to the electrical signal (S1400). Accordingly, the feedback device 100 may output the thermal feedback to the user.

The feedback end message may be obtained and the thermal feedback may be terminated (S1500). The feedback end message indicates termination of the thermal feedback, and the feedback device 100 may obtain the feedback termination message in a manner similar to the manner in which the feedback request message was obtained. The feedback device 100 may cease the thermoelectric operation when the feedback end message is received. However, the feedback end message may not be required to terminate the thermoelectric operation. For example, if the feedback information includes information on the time duration for applying the thermal feedback, the feedback device 100 may apply the thermoelectric operation for the corresponding time duration, and stop the operation after the time duration passed to terminate the thermal feedback. The time duration may include a start time and the end time.

In another example, the feedback request message may directly control the initiation and termination of the thermal feedback, without reference to information in memory. For example, if the feedback request message is a modulated voltage signal, feedback device 100 may initiate the thermal feedback when the voltage signal is asserted and terminated when the voltage signal is no longer asserted. In such embodiments, feedback controller 1400 may include circuits or electric devices that are enabled or disabled by the feedback request message (e.g., MOSFET drivers). Alternatively, a voltage magnitude may determine initiation and termination of the thermal feedback. For instance, a voltage magnitude is above a predetermined threshold, feedback controller 1400 may initiate the thermal feedback while a voltage magnitude below such threshold may terminate thermal feedback. In additional embodiments, the feedback request message may adjust the thermal feedback. For example, the feedback message may include information that instruct feedback controller 1400 to increase or decrease the output voltage or current. In yet other embodiments, the feedback request message may include information to initiate and terminate the thermal feedback in a predetermined period. For example, the feedback request message may specify a thermal feedback lasts 1 second based on the encoded modulation. In yet other embodiments, the feedback request message may specify the duty cycle of a PWM signal. For example, the feedback request message may be a signal from 0 to 1V which is interpreted by feedback controller 1400 as 0-100% duty cycle for outputting module 1200.

Figure 58:
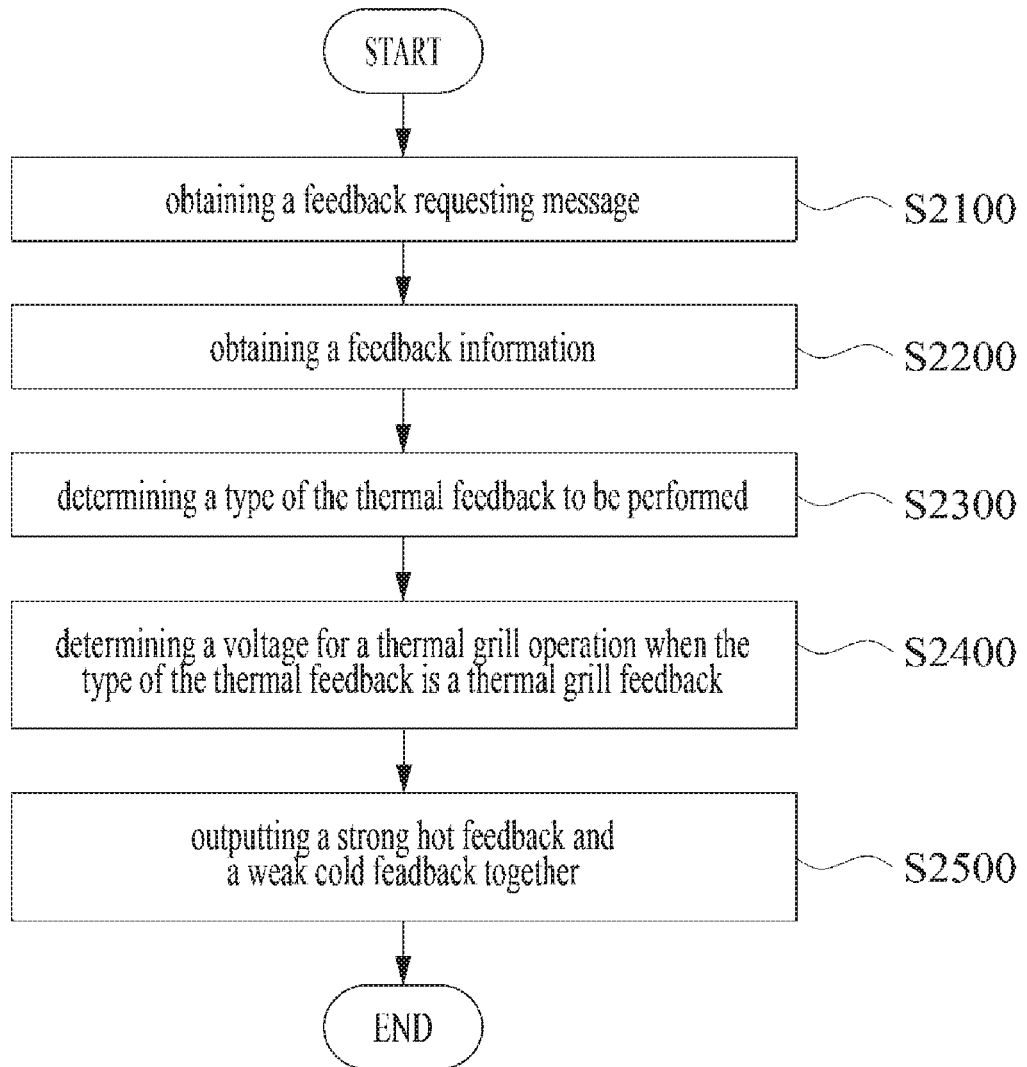
FIG. 58 is a flowchart illustrating a second example of a method for providing the thermal feedback according to an embodiment of the present disclosure.

3.2 Method for Providing Thermal Grill Feedback
3.2.1 Method for Providing Thermal Grill Feedback by Using Operating Power Control FIG. 58 is a flowchart illustrating a second example of a method for providing the thermal feedback according to an embodiment of the present disclosure.

Here, the second example of the method for providing the thermal feedback is related to providing the thermal grill feedback. Specifically, the second example of the method for providing the thermal feedback is related to providing the thermal grill feedback by using the operating power control manner.

Referring to FIG. 58, the method for providing the thermal feedback may comprise: obtaining a feedback request message (S2100), obtaining feedback information (S2200), determining a type of the thermal feedback to be output based on the feedback information, which is in particular determining whether or not the type of the thermal feedback to be output is the thermal grill feedback (S2300), when the type of the thermal feedback is the thermal grill feedback, determining the voltage to be applied for the thermal grill operation (S2400); and outputting simultaneously a high intensity hot feedback and a low intensity cold feedback (S2500).

The second example of the method for providing the thermal feedback may be performed by the feedback device 100 having the following features.

First, the feedback device 100 can perform simultaneously the heat generating operation in a portion of the contact surface 1600 and the heat absorbing operation in another portion of the contact surface 1600. To this end, the thermoelectric couple array 1240 includes a plurality of thermoelectric couple groups 1244 which are individually controllable, and the feedback controller 1400 can control the plurality of the thermoelectric couple groups 1244 individually.

Second, the feedback device 100 may output the hot feedback and the cold feedback in multiple intensity levels respectively. Therefore, the feedback controller 1400 can output an electric signal with a multi-level forward voltage and a multi-level reverse voltage.

Hereinafter, each of the above-described steps will be described in more detail.

First, the feedback request message may be obtained (S2100). This step may be similar to step S1100 in the first example of the method for providing the thermal feedback.

The feedback information may be obtained (S2200). This step may be similar to step S1200 in the first example of the method for providing the thermal feedback.

However, the feedback information may include at least information on the type of thermal feedback. The type of the thermal feedback includes hot feedback, cold feedback, and thermal grill feedback. The feedback information may further include information on the intensity level of the thermal feedback and the time duration of the application of the thermal feedback.

The type of the thermal feedback to be performed may be determined based on the feedback information (S2300).

If the type of the thermal feedback is the hot feedback, the feedback controller 1400 may apply the forward operating power to the heat outputting module 1200 and the heat outputting module 1200 may perform the heat generating operation. If the type of the thermal feedback is the cold feedback, the feedback controller 1400 may apply the reverse operating power to the heat outputting module 1200 and the heat outputting module 1200 may perform the heat absorbing operation. Here, the feedback controller 1400 may adjust the voltage level of the forward operating power or the reverse operating power according to the information on the intensity of the thermal feedback included in the feedback information.

If the type of the thermal feedback is the thermal grill feedback, the thermal grill operation may be performed as follows.

A voltage to be applied for the thermal grill operation, that is, the operating voltage is determined (S2400).

A table related to the voltage level and a table related to the thermoelectric couple group 1244 may be stored in the memory 2600. Hereinafter, the table related to the voltage level is referred to as "operating voltage table" and the table related to the thermoelectric couple group 1244 is referred to as "operating group table."

The operating voltage table relates to the operating voltages of various voltage levels for each of the hot feedback and the cold feedback. For example, the memory 2600, of which the feedback device 100 can provide the hot feedback and cold feedback of four intensity levels, may store the four levels of the forward voltage values for the hot feedback and the four levels of the reverse voltage values for the cold feedback. If the hot feedback and cold feedback use the same voltage values, the memory 2600 may store only four levels of voltage values.

The operating group table may include information on a first thermoelectric couple group 1244 and a second thermoelectric couple group 1244.

The feedback controller 1400 may obtain the forward voltage level and the reverse voltage level which are used for the thermal grill operation by referring to the operating voltage table stored in the memory 2600. In case of outputting the neutral grill feedback, the feedback controller 1400 may determine the level of the forward voltage suitable for the thermal grill operation to be lower than the level of the reverse voltage suitable for the thermal grill operation because the intensity of the heat absorbing operation need to be stronger than the intensity of the heat generating operation. For example, the feedback device 100 may select first level forward voltage and the third level reverse voltage or the first level forward voltage and the fourth level reverse voltage. Each value may vary somewhat depending on the specification of the feedback device 100, but it is essential that the level of the reverse voltage be greater than the level of the forward voltage.

To perform the neutral grill feedback, the intensity ratio of the cold feedback to the hot feedback needs to approximate the neutral ratio. Therefore, the feedback controller 1400 may select the magnitude of the forward voltage and the reverse voltage so that the intensity ratio of the cold feedback to the hot feedback approximates the neutral ratio.

Both the low-intensity hot feedback and the high-intensity cold feedback are simultaneously output (S2500).

When the voltage level is determined, the feedback controller 1400 may apply the forward voltage to the first thermoelectric couple group 1244 and apply the reverse voltage to the second thermoelectric couple group 1244 based on the operating group table. Here, the voltage magnitude of the reverse voltage is larger than the voltage magnitude of the forward voltage. This means that in terms of the intensity of the thermal feedback, the intensity of the heat absorbing operation used in the thermal grill operation is greater than the intensity of the heat generating operation used in the thermal grill operation.

The feedback device 100 may perform thermal grill feedback by the above steps.

Figure 59:
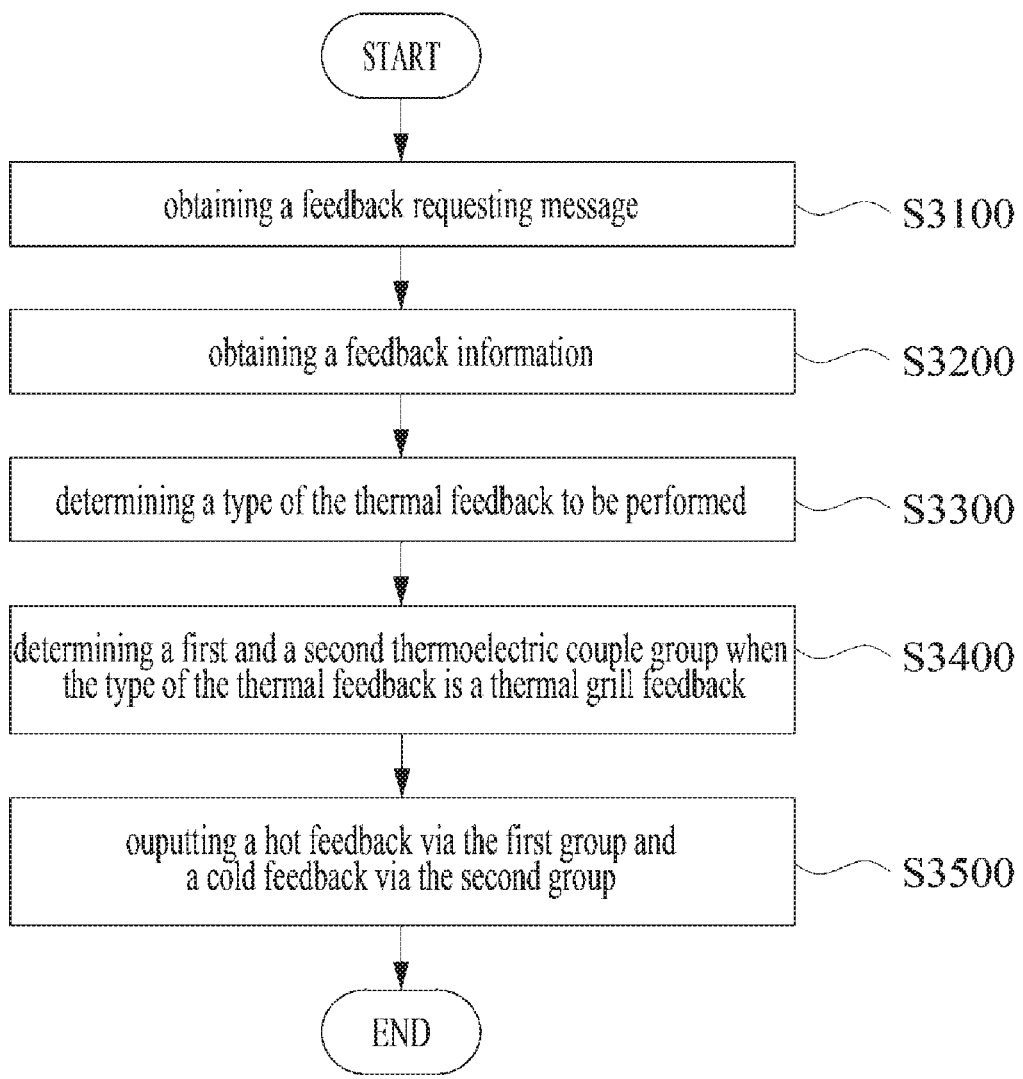
FIG. 59 is a flowchart illustrating a third example of a method for providing the thermal feedback according to an embodiment of the present disclosure.

3.2.2 Method for Providing Thermal Grill Feedback by Using Operating Area Control FIG. 59 is a flowchart illustrating a third example of a method for providing the thermal feedback according to an embodiment of the present disclosure.

Here, the third example of the method for providing the thermal feedback is related to providing the thermal grill feedback. Specifically, the third example of the method for providing the thermal feedback is related to providing the thermal grill feedback by using the operating area control manner.

Referring to FIG. 59, the method for providing the thermal feedback may comprise: obtaining a feedback request message (S3100), acquiring feedback information (S3200), determining a type of the thermal feedback to be output based on the feedback information, which is in particular determining whether or not the type of the thermal feedback to be output is the thermal grill feedback (S3300), when the type of the thermal feedback is the thermal grill feedback, determining a region to which a voltage for a thermal grill operation is applied (S3400), and outputting simultaneously the hot feedback and the cold feedback through a first thermoelectric couple group 1244-1 and a second thermoelectric couple group 1244-2 (S3500).

The third example of the method for providing the thermal feedback may be performed by the feedback device 100 having the following features:

The feedback device 100 can perform the heat generating operation in a portion of the contact surface 1600 and the heat absorbing operation in another portion of the contact surface 1600 simultaneously. The thermoelectric couple array 1240 of the feedback device 100 includes a plurality of thermoelectric couple groups 1244 which are individually controllable, as described above. The feedback controller 1400 can control the plurality of thermoelectric couple groups 1244 individually, as described above.

Hereinafter, each of the above-described steps will be described in more detail.

First, the feedback request message is acquired (S3100), the feedback information is obtained (S3200), and the type of the thermal feedback to be output is determined based on the feedback information. These steps may be similar to steps S2100, S2200, S2300 in the second example of the method for providing the thermal feedback, respectively.

If the type of the thermal feedback is the thermal grill feedback, the thermal grill operation is performed as follows:

The region of the thermoelectric couple array 1240 to which a voltage is applied for the thermal grill operation is determined (S3400).

The feedback controller 1400 may determines the first thermoelectric couple group 1244-1 to perform the heat generating operation and the second thermoelectric couple group 1244-2 to perform the heat absorbing operation among the plurality of thermoelectric couple groups 1244 included in the thermoelectric couple array 1240. The feedback controller 1400 may select the first thermoelectric couple group 1244-1 and the second thermoelectric couple group 1244-2 so that the ratio of the temperature change amount of the second thermoelectric couple group 1244-2 to the temperature change amount of the first thermoelectric couple group 1244-1 and the area ratio of the second thermoelectric couple group 1244-2 to the first thermoelectric couple group 1244-1 establish the neutral ratio.

For example, when the temperature change amount of the heat generating operation and that of the heat absorbing operation is same, the feedback controller 1400 may adjust the area size of the first thermoelectric couple group 1244-1 and the second thermoelectric couple group 1244-2 so that the neutral ratio is established by the area ratio of the second thermoelectric couple group 1244-2 to the first second thermoelectric couple group 1244-2.

Lastly, the hot feedback and the cold feedback are simultaneously output through the first thermoelectric couple group 1244-1 and the second thermoelectric couple group 1244-2 (S3500), respectively.

The feedback controller 1400 may apply the forward operating power to the first thermoelectric couple group 1244-1 and apply the reverse operating power to the second thermoelectric couple group 1244-2. Accordingly, the heat generating operation is performed in the first thermoelectric couple group 1244-1 and the heat absorbing operation is performed in the second thermoelectric couple group 1244-2. Thus, the hot feedback and the cold feedback may be outputted via each region of the contact surface 1600 to provide the thermal grill feedback to the user.

The feedback device 100 may perform the thermal grill feedback by the above steps.

3.2.3. Method for Providing Thermal Grill Feedback by Using Operating Time Control FIG. 60 is a flowchart of a fourth example of the method of providing the thermal feedback according to an embodiment of the present disclosure.

Here, the fourth example of the method for providing the thermal feedback is related to providing the thermal grill feedback. Specifically, the fourth example of the method for providing the thermal feedback is related to providing the thermal grill feedback by using the operating time control manner.

Figure 60:
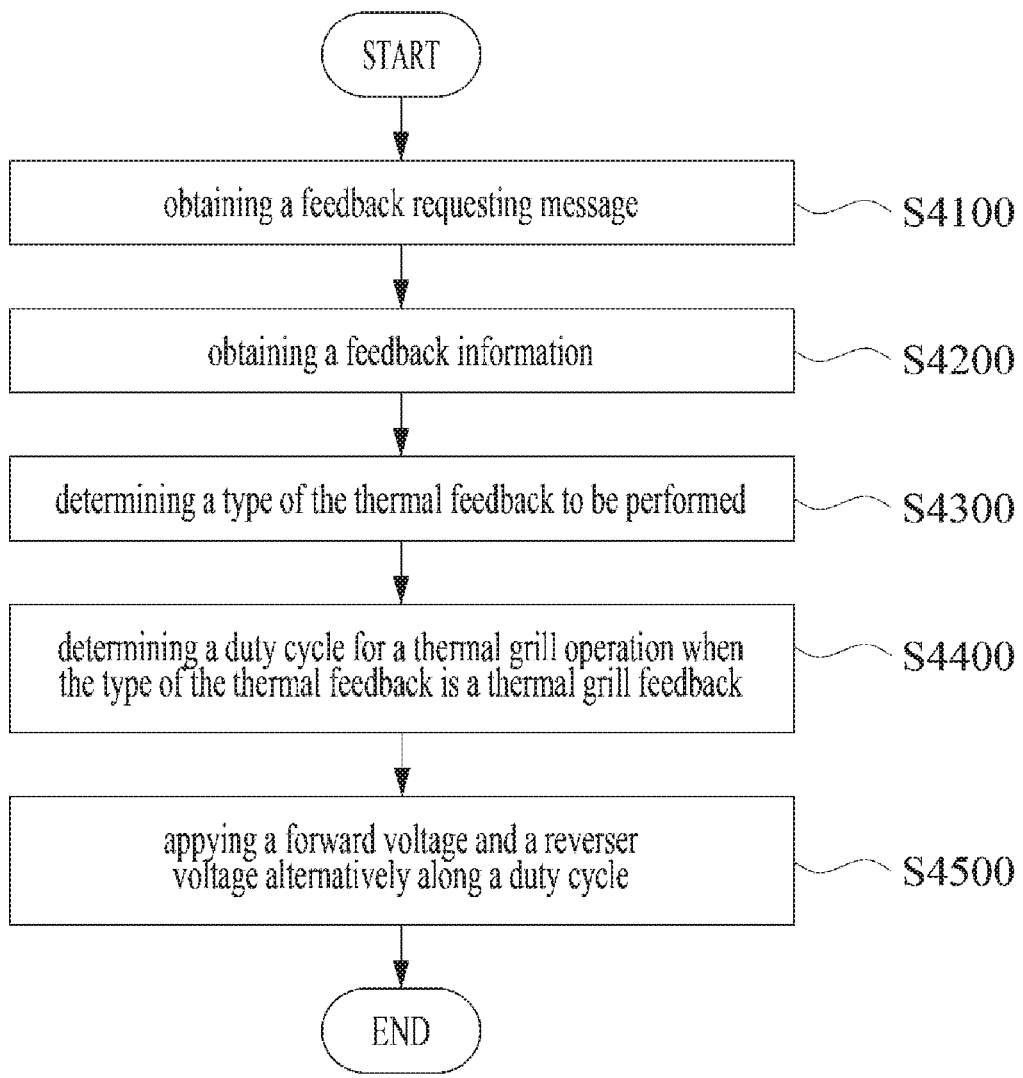
FIG. 60 is a flowchart illustrating a fourth example of a method for providing the thermal feedback according to an embodiment of the present disclosure.

Referring to FIG. 60, the method for providing the thermal feedback may comprise: obtaining a feedback request message (S4100), obtaining feedback information (S4200), determining a type of the thermal feedback to be output based on the feedback information, which is in particular determining whether or not the type of the thermal feedback to be output is the thermal grill feedback (S4300), when the type of the thermal feedback is the thermal grill feedback, determining a duty rate of the operating power for the thermal grill operation (S4400); and outputting alternately the hot feedback and the cold feedback by applying the forward operating power and the reverse operating power in accordance with the determined duty rate (S4500).

Hereinafter, each of the above-described steps will be described in more detail.

The feedback request message is acquired (S4100), the feedback information is obtained (S4200), and the type of the thermal feedback to be performed is determined based on the feedback information (S4300). In particular, it is determined whether the type of the thermal feedback is the thermal grill feedback (S4300). These steps may be similar to steps S3100, S3200, and S3300 in the second example of the method for providing the thermal feedback, respectively.

If the type of the thermal feedback is the thermal grill feedback, the thermal grill operation is performed as follows.

The duty rate of the operating power for the thermal grill operation is determined (S4400).

The feedback controller 1400 may apply the forward operating power and the reverse operating power alternately with time, and determine the application time of the forward operating power and the application time of the reverse operating power. Specifically, the feedback controller 1400 may determine the application time for the forward operating power and the application time for the reverse operating power so that the temperature ratio of the heat absorbing operation to the heat generating operation and the time duration ratio of the application time for the reverse operating power to the application time for the forward operating power establish the neutral ratio. The repeating cycle of the heat generating operation and the heat absorbing operation may be less than a predetermined interval so that the user cannot recognize the hot feedback and the cold feedback separately.

For example, when the temperature change amount of the heat generating operation and the temperature change amount of the heat absorbing operation is the same, the feedback controller 1400 may adjust the application time for the forward operating power and the reverse operating power so that the neutral ratio is established by the duty rate. The duty rate may mean the rate of the application duration of the forward operating power and the reverse operating power.

In step S4500, a signal related to the hot feedback and a signal related to the cold feedback are alternately output in response to the electric signal which applies the forward operating power and the reverse operating power by turn to the heat outputting module 1200.

The feedback controller 1400 may apply the forward voltage during a first duration and apply the reverse voltage during a second duration. Here, the first duration may correspond to the application time for the forward operating power and the second duration may correspond to the application time for the reverse operating power. Accordingly, the heat generating operation is performed during the first duration, and the heat absorbing operation is performed during the second duration. Thus, the hot feedback and the cold feedback may be performed alternately, and thus the thermal grill feedback may be provided to the user.

The feedback device 100 may perform thermal grill feedback by the above steps.

3.2.4. Method for Providing Thermal Grill Feedback by Using Combination of Operating Area Control and Operating Time Control FIG. 61 is a flowchart of a fifth example of the method of providing the thermal feedback according to an embodiment of the present disclosure.

Here, the fifth example of the method for providing the thermal feedback is related to providing the thermal grill feedback. Specifically, the fifth example of the method for providing the thermal feedback is related to providing the thermal grill feedback by using a combination of the operating area control manner and the operating time control manner.

Figure 61:
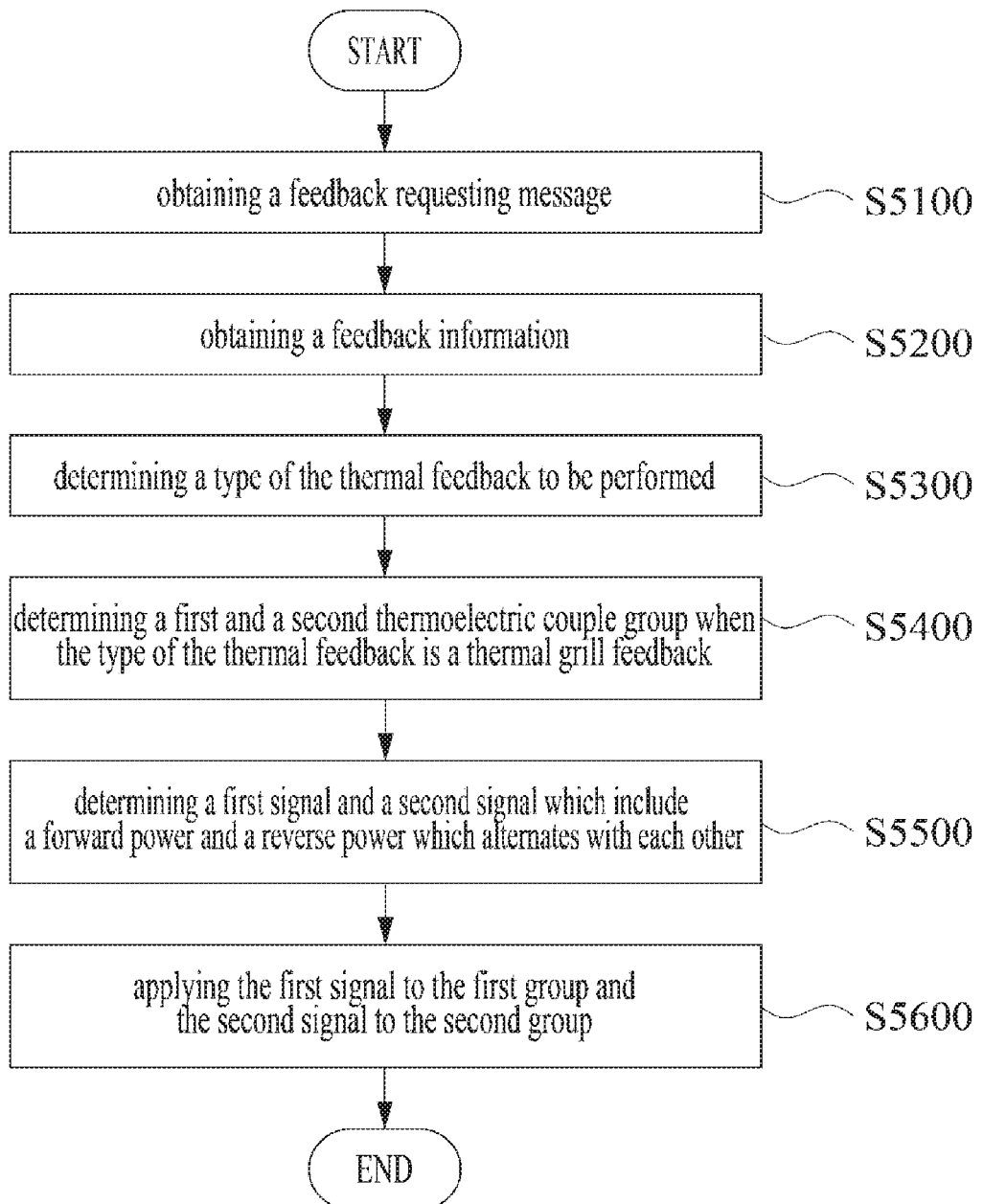
FIG. 61 is a flowchart illustrating a fifth example of a method for providing the thermal feedback according to an embodiment of the present disclosure.

Referring to FIG. 61, the method for providing the thermal feedback may comprise: obtaining a feedback request message (S5100), obtaining feedback information (S5200), determining a type of the thermal feedback to be output based on the feedback information—in particular, determining whether or not the type of the thermal feedback to be output is the thermal grill feedback (S5300), when the type of the thermal feedback is the thermal grill feedback, determining a first thermoelectric couple group 1244-1 to perform a first operation and a second thermoelectric couple group 1244-2 to perform a second operation (S5400), determining a duty rate of the power for a thermal grill operation (S5500), and providing the hot feedback and the cold feedback simultaneously by outputting the hot feedback and cold feedback alternately through the first thermoelectric group 1244-1 using a first power applying the forward voltage and the reverse voltage by turns to the first thermoelectric couple group 1244-1 and by outputting the cold feedback and the hot feedback alternately using a second power applying the reverse voltage and the forward voltage, where the first power and the second power are staggered with each other (S5600).

A fifth example of the method for providing thermal feedback may be performed by the feedback device 100 configured to perform the heat generating operation in a portion of the contact surface 1600 and the heat absorbing operation in another portion of the contact surface simultaneously. The thermoelectric couple array 1240 of the feedback device 100 includes a plurality of thermoelectric couple groups 1244 which are individually controllable, as described above. The feedback controller 1400 can control the plurality of thermoelectric couple groups 1244 individually, as described above.

Hereinafter, each of the above-described steps will be described in more detail.

First, the feedback request message is obtained (S5100), the feedback information is obtained (S5200), and the type of the thermal feedback to be performed is determined based on the feedback information—In particular, it is determined whether the type of the thermal feedback is thermal grill feedback (S5300). These steps may be similar to steps S4100, S4200, and S4300 in the fourth example of the method of providing thermal feedback, respectively.

When the type of the thermal feedback is the thermal grill feedback, the thermal grill operation is performed as follows.

First, the first thermoelectric couple group 1244 for performing the first operation and the second thermoelectric couple group 1244 for performing the second operation are determined for the thermal grill operation (S5400).

The feedback controller 1400 may determine the first thermoelectric couple group 1244-1 and the second thermoelectric couple group 1244-2 to have the same area.

Here, the first operation and the second operation are operations in which the heat generating operation and the heat absorbing operation are alternately performed with time using the duty cycle, and the order of the heat generating operation and the heat absorbing operation is shifted between the first operation and the second operation. That is, when the heat generating operation of the first operation is performed, the heat absorbing operation of the second operation may be performed, and when the heat absorbing operation of the first operation is performed, the heat generating operation of the second operation may be performed.

The duty rate related to the operating power is determined for the thermal grill operation (S5500).

The feedback controller 1400 may apply the forward voltage and the reverse voltage alternately in time, and determine the application time for the forward voltage and the application time for applying the reverse voltage. Here, the feedback controller 1400 may adjust the magnitude of the forward voltage, the magnitude of the reverse voltage, the time duration of the forward voltage and the time duration of the reverse voltage so that the temperature change ratio of the heat absorbing operation to the heat generating operation and the time ratio of the time for performing the heat absorbing operation to the time for performing the heat generating operation establish the neutral ratio.

For example, the feedback controller 1400 may determine the forward voltage timing and the reverse voltage timing so that the neutral ratio in terms of time is established when the ratio of the temperature change amount due to the heat generating operation and the temperature change amount due to the heat absorbing operation is the same.

Lastly, the electric signal is applied to the first thermoelectric couple group 1244-1 and the second thermoelectric couple group 1244-2. Thus, the first thermoelectric couple group 1244-1 may output the hot feedback when the second thermoelectric couple group 1244-2 outputs the cold feedback, and the first thermoelectric couple group 1244-1 may output the cold feedback when the second thermoelectric couple group 1244-2 outputs the hot feedback. Therefore, the hot feedback and cold feedback may be outputted simultaneously (S5500).

During a first period, the feedback controller 1400 may apply the forward voltage to the first thermoelectric couple group 1244-1 and the reverse voltage to the second thermoelectric couple group 1244-2. Also, during the second period, the feedback controller 1400 may apply the reverse voltage to the first thermoelectric couple group 1244-1 and the forward voltage to the second thermoelectric couple group 1244-2. Therefore, for the first period, the first thermoelectric group 1244-1 may perform the heat generating operation and the second thermoelectric group 1244-2 may perform the heat absorbing operation. For the second period, the first thermoelectric group 1244-1 may perform the heat absorbing operation and the second thermoelectric group 1244-2 may perform the heat generating operation. Thus, from the viewpoint of the thermoelectric couple array 1240, the hot feedback and cold feedback are provided simultaneously, and from the viewpoint of each thermoelectric couple group 1244, the hot feedback and cold feedback are provided alternately.

The feedback device 100 may perform thermal grill feedback by the above steps.

3.2.5. Regarding Neutral Grill Feedback, Hot Grill Feedback and Cold Grill Feedback In the above-description related to the second to the fifth examples of the method for providing the thermal feedback according to an embodiment of the present disclosure, the neutral grill feedback was provided. The hot grill feedback or the cold grill feedback may be provided instead of the neutral grill feedback.

For example, regarding the method for providing the thermal grill feedback using the operating power control, the feedback controller 1400 may adjust the magnitude ratio of the reverse voltage to forward voltage to be smaller than the voltage magnitude ratio used for the neutral grill feedback, to provide the hot grill feedback. On the other hand, the feedback controller 1400 may adjust the magnitude ratio of the reverse voltage to forward voltage to be greater than the voltage magnitude ratio used for the neutral grill feedback, to provide the cold grill feedback.

As another example, regarding the method for providing the thermal grill feedback using the operating area control, the feedback controller 1400 may adjust the area ratio of the heat absorbing area to the heat generating area to be smaller than the area ratio used for the neutral grill feedback, to provide the hot grill feedback. On the other hand, the feedback controller 1400 may adjust the area ratio of the heat absorbing area to the heat generating area to be greater than the area ratio used for the neutral grill feedback, to provide the cold grill feedback.

Yet another example, regarding the method for providing the thermal grill feedback using the operating time control, the feedback controller 1400 may adjust the time ratio of the heat absorbing period to the heat generating period to be smaller than the time ratio used for the neutral grill feedback, to provide the hot grill feedback. On the other hand, the feedback controller 1400 may adjust the time ratio of the heat absorbing period to the heat generating period to be greater than the time ratio used for the neutral grill feedback, to provide the cold grill feedback.

That is, the feedback device 100 may provide the hot grill feedback by decreasing at least one of the voltage ratio, the area ratio, and the time ratio of the heat absorbing operation to the heat generating operation and provide the cold grill feedback by increasing at least one thereof.

3.3. Regarding Preventing Skin Damage

In the above-description related to the first to the fifth examples of the method for providing the thermal feedback according to an embodiment of the present disclosure, it may be needed to avoid for the feedback device 100 transmitting an excessively high amount of heat to the user.

To this end, the feedback controller 1400 may limit the magnitude of the voltage applied to the thermoelectric couple array 1240 to be less than a predetermined threshold voltage value, or prevent the voltage applying time from exceeding a predetermined threshold time.

3.4. Method for Preventing Thermal Inversion Illusion 3.4.1. Method for Preventing Thermal Inversion Illusion Using Buffering Operation FIG. 62 is a flowchart of a sixth example of the method for providing the thermal feedback according to an embodiment of the present disclosure.

Here, the sixth example of the method for providing the thermal feedback is related to preventing the thermal inversion illusion.

Figure 62:
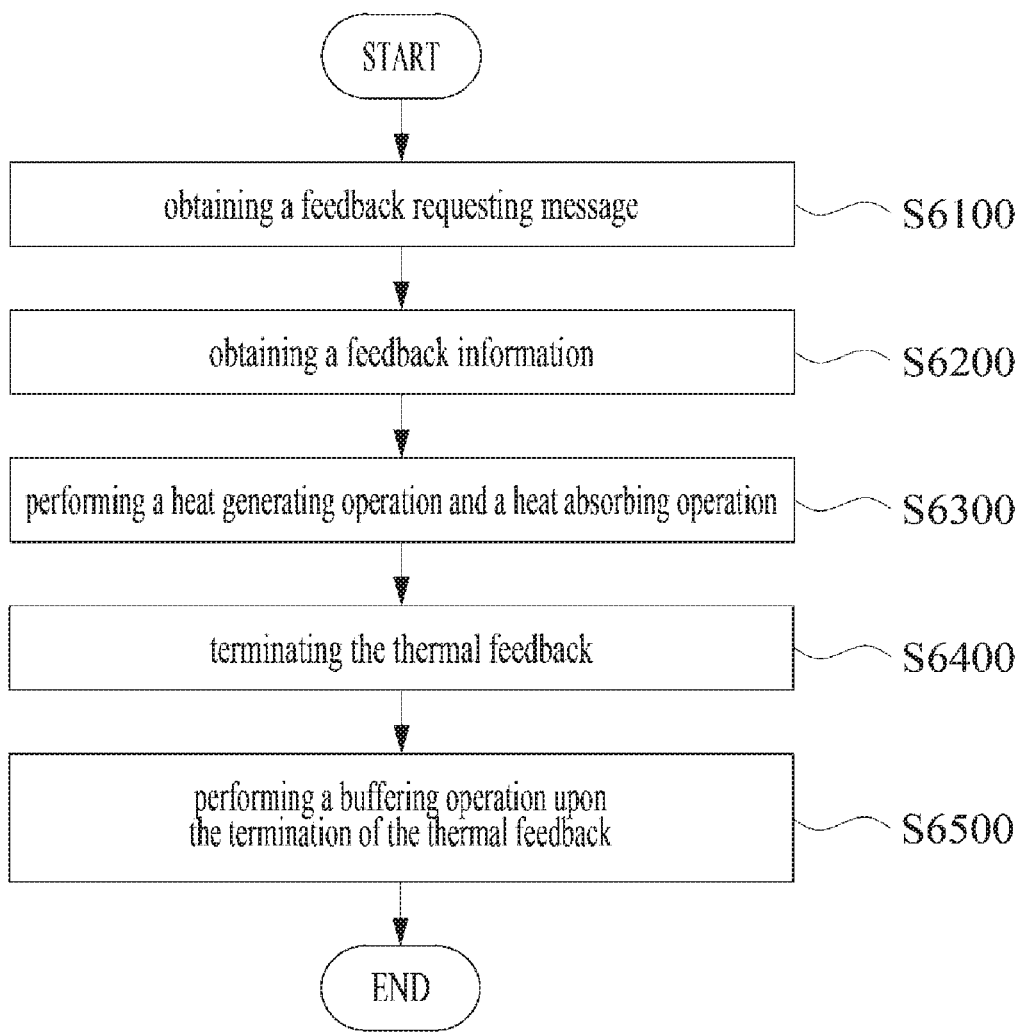
FIG. 62 is a flowchart illustrating a sixth example of a method for providing the thermal feedback according to an embodiment of the present disclosure.

Referring to FIG. 62, the method for providing the thermal feedback may comprise: obtaining a feedback request message (S6100), obtaining feedback information (S6200), performing a heat generating operation or a heat absorbing operation (S6300), terminating the thermal feedback (S6400), and performing a buffering operation at the termination of the thermal feedback (S6500).

Hereinafter, each of the above-described steps will be described in more detail.

First, a feedback request message is obtained (S6100), feedback information is obtained (S6200), and a heat generating operation or the heat absorbing operation is performed based on the feedback information (S6300). These steps may be understood from another example of the method for providing thermal feedback according to an embodiment of the present disclosure described above. Here, the voltage applied to the thermoelectric couple array 1240 by the feedback controller 1400 for the heat generating operation or the heat absorbing operation is referred to as the operating voltage.

The thermal feedback is terminated (S6400).

The feedback controller 1400 may terminate the thermal feedback after a predetermined time from the start of the thermal feedback. That is, the feedback controller 1400 may cut off the power to the thermoelectric couple array 1240 after a predetermined time has passed since the heat generating operation or the heat absorbing operation is started.

Alternatively, the feedback controller 1400 may count the time since the thermal feedback is started and terminate the thermal feedback when the counted time has passed a time indicated by the time information included in the feedback information.

Or the feedback controller 1400 may terminate the thermal feedback upon receiving the feedback termination message.

The termination of the thermal feedback may be achieved by shutting off the operating power applied to the thermoelectric couple array 1240 for providing the thermal feedback.

The buffering operation is performed at the end of the thermal feedback (S6500).

Here, the buffering operation is an operation for preventing the temperature of the contact surface 1600 from suddenly changing from the saturation temperature to the initial temperature at the end of the heat generating operation or the heat absorbing operation, in order to prevent the thermal inversion illusion phenomenon.

To this end, the feedback controller 1400 may apply the buffering power to the thermoelectric couple array 1240 for a predetermined time at the end of the thermal feedback.

Here, the buffering power may have the same current direction with the operating power. To this end, the feedback controller 1400 may determine the current direction of the buffering power based on the current direction of the operating power or the type of the thermal feedback applied for outputting the thermal feedback.

And, the buffering power may be a power for inducing the thermoelectric operation of which the intensity is smaller than the thermoelectric operation induced by the operating power. To this end, the buffering power may have the following characteristics.

For example, the buffering power may have a voltage value smaller than the voltage value of the operating power, that is, the operating voltage. Similarly, the buffering current may have a current value smaller than the current value of the operating power, that is, the operating current. In addition, the buffering voltage or the buffering current may take the form of decreasing during the buffering duration in which the buffering operation is performed.

As another example, the buffering power may be provided in the form of a duty signal. If the operating power is a direct current power, the buffering power is provided as a duty signal, so that the rate of temperature change on the contact surface 1600 may be reduced. If the operating power is of the duty signal type, the buffering power source may be provided with a duty signal whose duty rate is smaller than that of the operating power, so that the rate of temperature change on the contact surface 1600 may be reduced. Here, the duty rate of the buffering power may be reduced during the buffering period.

Due to the buffering voltage is applied, the rate of temperature change of the contact surface 1600 is reduced, so that the thermal inversion illusion may be alleviated or eliminated.

Alternatively, when the thermoelectric elements of the feedback device 100 are provided as the thermoelectric couple array 1240 having the plurality of thermoelectric couple groups 1244, the buffering operation may also be performed using the area control.

Specifically, the feedback controller 1400 may perform the buffering operation by applying the buffering power to a buffering group at the end of the thermal feedback. The buffering group may include less thermoelectric couple group 1244 than the operating group, that is, the thermoelectric couple group to which the operating power is applied for outputting the thermal feedback.

For example, at the end of the thermal feedback which is performed by the ten thermoelectric couple groups 1244, the feedback controller 1400 may apply the buffering power to the eight thermoelectric groups 1244 to weaken the intensity of the thermoelectric operation, so that the rate of temperature change toward the initial temperature on the contact surface 1600 may be reduced. Here, the operating group does not include all the thermoelectric couple groups 1244 of the thermoelectric elements. The buffering group only needs to be fewer than the operating group, so the buffering group does not necessarily have to be part of the operating group.

As described above, when the buffering operation is performed using the area control, a power whose voltage value, current value and duty rate are smaller than the operating power may be used as the buffering power. However, since the number of the thermoelectric couple groups included in the buffering groups is smaller than the number of the thermoelectric couple groups included in the operation group, the thermal inversion illusion may be prevented from occurring even when the operating power is used as the buffering power.

In the above-description, the buffering operation may be interpreted as being implemented by applying the buffering power when the operating power is cut off. In the case where the operating power is used as the buffering power, the buffering operation may be interpreted as being implemented by reducing the number of the thermoelectric couple groups included in the operating group to which the operating power is applied. Specifically, the buffering operation may be implemented by reducing the number of the operation group during the buffering duration after the end of the thermal feedback instead of turning off the operating power to the entire operation group at the end of the thermal feedback.

In the above-description, the buffering operation may be performed during the buffering period after cutting off the operating power for terminating the output of the thermal feedback. However, the buffering operation does not necessarily have to be performed immediately when the operation power is cut off, and the buffering operation may be performed after a predetermined time has elapsed from when applying of the operation power is stopped.

3.4.2. Method for Preventing Thermal Inversion Illusion Using Voltage Control Also, the buffering voltage may have a multi-level voltage value in the above buffering operation. Whereby, the buffering operation may include a plurality of buffering stages. The plurality of buffering stages are performed sequentially with time, and a larger voltage may be used a prior stage of the buffering operation.

For example, the feedback controller 1400 may set the first buffering voltage, the second buffering voltage, and the third buffering voltage. Accordingly, the feedback controller 1400 may performs the first buffering stage by applying the first buffering voltage, the second buffering stage by applying the second voltage, and the third buffering stage by applying the third second buffering voltage.

Here, the first buffering voltage may be smaller than the operating voltage, the second buffering voltage may be smaller than the first buffering voltage, and the third buffering voltage may be smaller than the second buffering voltage. Accordingly, the first buffering stage may follow the heat generating or the heat absorbing operation, the second buffering zone may follow the first buffering stage, and the third buffering stage may follow the second buffering stage. Here, the first buffering voltage, the second buffering voltage, the third buffering voltage have the same current direction with the operating voltage.

3.4.3. Method for Preventing Thermal Inversion Illusion Considering Thermal Feedback Intensity FIG. 63 is a flowchart related to a seventh example of the method for providing the thermal feedback according to an embodiment of the present disclosure.

Here, the seventh example of the method for providing the thermal feedback is related to preventing the thermal inversion illusion. Specifically, the seventh example of the method for providing the thermal feedback is related to preventing the thermal inversion illusion considering the intensity of the terminated thermal feedback.

Figure 63:
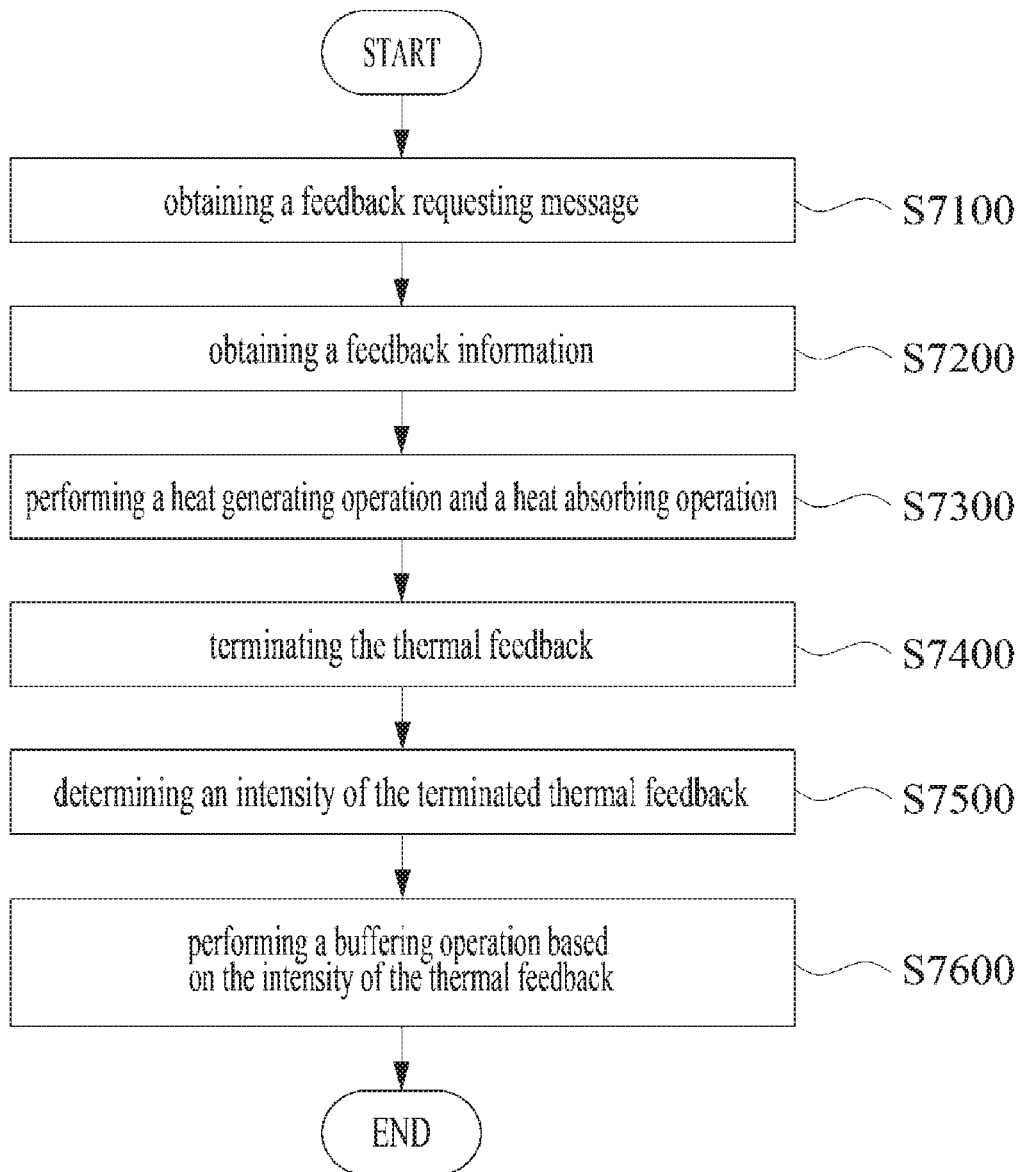
FIG. 63 is a flowchart illustrating a seventh example of a method for providing the thermal feedback according to an embodiment of the present disclosure.

Referring to FIG. 63, the method for providing the thermal feedback may comprise: obtaining a feedback request message (S7100), obtaining feedback information (S7200), performing the heat generating operation or the heat absorbing operation based on the feedback information (S7300), terminating the thermal feedback (S7400), determining the intensity of the thermal feedback (S7500), and determining whether or not to perform a buffering operation based on intensity of the thermal feedback (S7600).

Hereinafter, each of the above-described steps will be described in more detail.

First, the feedback request message is obtained (S7100), the feedback information is obtained (S7200), the heat generating operation or the heat absorbing operation is performed based on the feedback information (S7300), and the thermal feedback is terminated (S7400). These steps may be similar to steps S6100, S6200, S6300, and S6400 described above.

The intensity of the thermal feedback may be determined (S7500).

As the thermoelectric operation is terminated, the feedback controller 1400 may determine the intensity of the thermal feedback that has been terminated. The feedback controller 1400 may determine the intensity of the thermal feedback based on the voltage magnitude and current direction included in the feedback information.

Whether to perform the buffering operation may be determined based on the intensity of the thermal feedback (S7600).

It may be determined whether the intensity of the thermal feedback is greater than a predetermined intensity. Accordingly, the feedback controller 1400 may perform the buffering operation when the intensity of the thermal feedback is greater than the predetermined intensity, and may not perform the buffering operation when the intensity of the thermal feedback is not greater than the predetermined intensity.

In other words, the feedback controller 1400 may apply the buffering voltage to the thermoelectric couple array 1240 when the intensity of the thermal feedback is greater than the predetermined intensity, and may not apply any power when the intensity of the thermal feedback is equal to or smaller than the predetermined intensity.

If the intensity of the thermal feedback is below a certain level, it is not needed to perform the buffering operation since the thermal inversion illusion is not felt by the user at the end of the thermal feedback output.

Here, the predetermined intensity may be differently set for the hot feedback and the cold feedback. For example, the predetermined intensity for the cold feedback may be set smaller than the hot feedback. This is because the temperature change rate is greater at the end of the cold feedback than the hot feedback. Therefore, the buffering operation may be performed for the cold feedback of the certain intensity, while not for the hot feedback of the same intensity.

3.4.4. Method for Preventing Thermal Inversion Illusion Considering Thermal Feedback Type.

Figure 64:
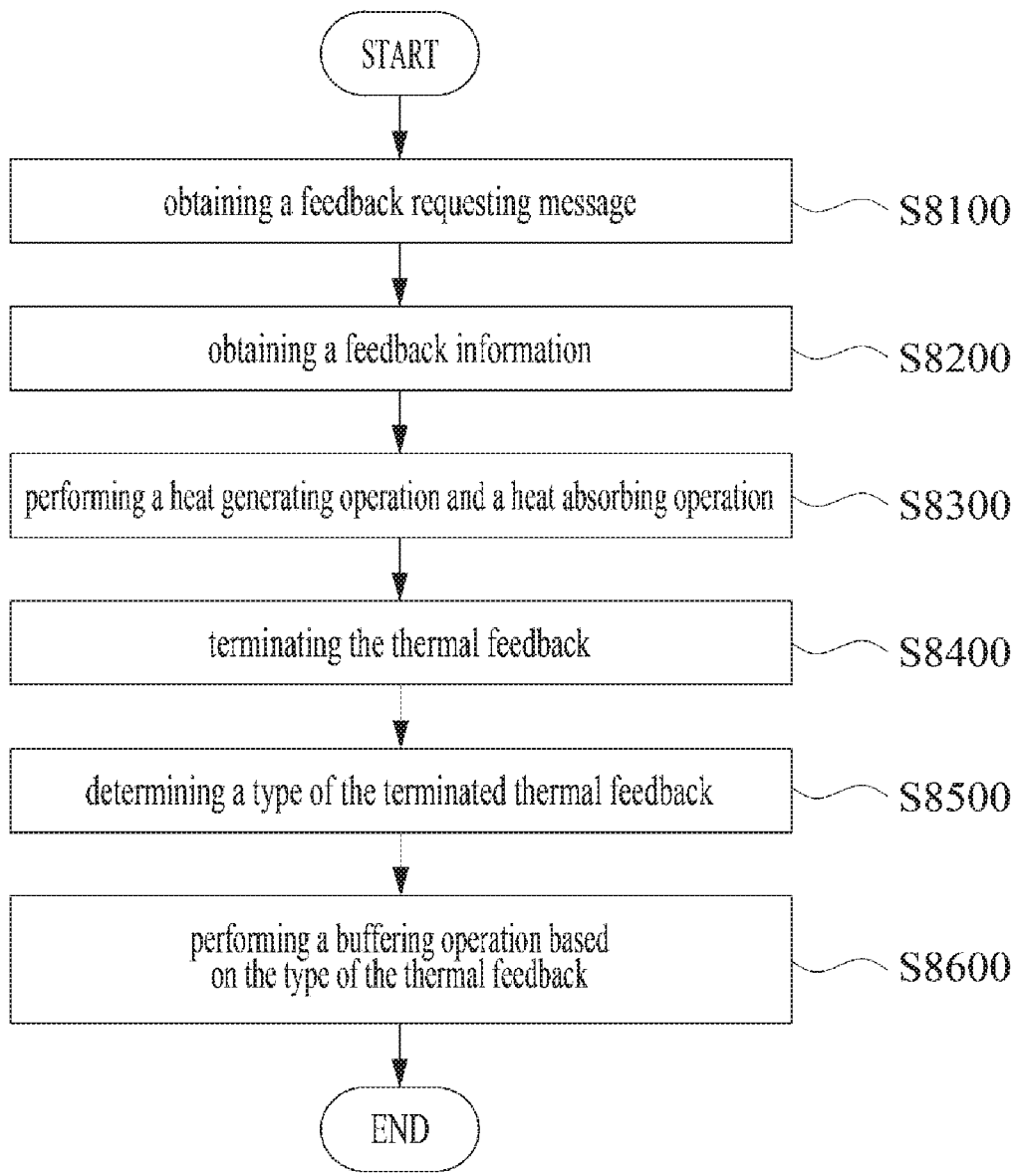
FIG. 64 is a flowchart illustrating an eighth example of a method for providing the thermal feedback according to an embodiment of the present disclosure.

FIG. 64 is a flowchart related to an eighth example of the method for providing the thermal feedback according to an embodiment of the present disclosure.

Here, the eighth example of the method for providing the thermal feedback is related to preventing the thermal inversion illusion. Specifically, the eighth example of the method for providing the thermal feedback is related to preventing the thermal inversion illusion considering the type of the terminated thermal feedback.

Referring to FIG. 64, the method for providing the thermal feedback may comprise: obtaining a feedback request message (S8100), obtaining feedback information (S8200), performing the heat generating operation or the heat absorbing operation based on the feedback information (Step S8300), terminating the thermal feedback (S8400), determining the type of the thermal feedback (S8500), and operating the buffering operations differently according to the determined type of thermal feedback (S8600).

Hereinafter, each of the above-described steps will be described in more detail.

First, a feedback request message is acquired (S8100), feedback information is obtained (S8200), and the heat generating operation or the heat absorbing operation is performed based on the feedback information (S8300). These steps may be similar to steps S7100, S7200, S7300 and S7400 described above.

The type of the thermal feedback is determined (S8500).

As the thermoelectric operation is terminated, the feedback controller 1400 may determine the type of the thermal feedback that has been terminated. The type of the thermal feedback may include the hot feedback and the cold feedback. The feedback controller 1400 may determine the type of the thermal feedback based on the feedback information or the current direction of the operating power.

The buffering operation is performed differently according to the type of the thermal feedback (S8600).

As described above, since the temperature change rate at the end of cold feedback is steeper than the temperature change rate at the end of the hot feedback, it may perform the buffering operation differently between the two feedbacks.

The feedback controller 1400 may perform the buffering operation using the first buffering voltage for the first buffering duration for the hot feedback, and may perform the buffering operation using the second buffering voltage during the second buffering duration for the cold feedback.

For one example, the second buffering duration may be greater than the first buffering duration. This is because the temperature change rate on the contact surface 1600 from the saturation temperature toward the initial temperature at the end of cold feedback is faster than at the end of hot feedback when the temperature difference between the initial temperature and the saturation temperature is same in both the hot feedback and the cold feedback.

As another example, the first buffering time may be greater than the second buffering time. This is because the temperature difference induced at the contact surface 1600 by the hot feedback is greater than the temperature difference induced at the contact surface 1600 by the cold feedback when the operating voltage applied for both the hot feedback and the cold feedback is same.

The feedback controller 1400 may generate the buffering power for the buffering operation related to the end of the hot feedback and the buffering power for the buffering operation related to the end of the cold feedback, which have different voltage value.

For one example, the first buffering voltage for the hot feedback may be less than the second buffering voltage for the cold feedback. This is because the temperature return speed of the cold feedback is faster than that of the hot feedback when the temperature difference between the initial temperature and the saturation temperature is the same.

As another example, the first buffering voltage for the hot feedback may be greater than the second buffering for the cold feedback. This is because the temperature difference is greater in the hot feedback than in the cold feedback when the same operating voltage is used for both feedbacks. The buffering power for the hot feedback and the cold feedback may have different current values or duty rates instead of different voltage values.

The voltage magnitude ratio, current magnitude ratio or duty rate ratio of the buffering power to the operating power may be less than 1 respectively. Those ratios may be set differently for the buffering operation for the cold feedback and the buffering operation for the hot feedback.

Here, the ratio value used in the buffering operation performed at the end of the cold feedback may be larger than the ratio value used in the buffering operation performed at the end of the hot feedback. This is because the temperature return speed in cold feedback may be faster.

Specifically, when the operating power for hot feedback has a first voltage, a first current and a first duty rate and the operating power for cold feedback has a second voltage, a second current and a second duty rate, the buffering power related to the hot feedback has a third voltage, a third current and a third duty rate, and the buffering power related to the cold feedback has a fourth voltage, a fourth current and a fourth duty rate, the ratio of the third voltage to the first voltage, the third current to the first current or the third duty rate to the first duty rate may be smaller than the ratio of the fourth voltage to the second voltage, the fourth current to the second current or the fourth duty rate to the second duty rate, respectively. This is because the temperature change speed from the saturation temperature toward the initial temperature is greater at the end of cold feedback than at the end of the hot feedback when the temperature difference between the initial temperature and the saturation temperature is same in the hot feedback and the cold feedback.

Or the ratio value related to the cold feedback may be smaller than the ratio value related to the hot feedback. This is because the temperature difference between the initial temperature and the saturation temperature is greater in the hot feedback than in the cold feedback when the operating voltage is same in the hot feedback and the cold feedback.

For yet another example, the feedback controller 1400 may determine the number of the thermoelectric couple groups to be included in the buffering groups performing the buffering operation, based on the type of the thermal feedback to be terminated.

Specifically, the number of the thermoelectric couple groups in the buffering group performing the buffering operation at the end of the hot feedback may be smaller than the number of the thermoelectric couple groups in the buffering groups performing the buffering operation at the end of the cold feedback. This is because the temperature change speed may be greater at the end of the cold feedback than at the end of the hot feedback. Similarly, the number ratio of the thermoelectric couple groups in the buffering group to the thermoelectric couple groups in the operating group may be smaller for the hot feedback than for the cold feedback.

Conversely, the number of the thermoelectric couple groups in the buffering group performing the buffering operation at the end of the hot feedback may be greater than the number of thermoelectric couple groups in the buffering groups performing the buffering operation at the end of the cold feedback. This is because the temperature difference due to the hot feedback may be greater than the temperature difference due to the cold feedback. Similarly, the ratio of the number of the thermoelectric couple group in the buffering group to the operating group may be smaller for the cold feedback than for the hot feedback.

Here, the buffering power and the operating power may be the same power. In this case, the buffering operation may be interpreted as an operation of gradually reducing the number of operating groups to which operating power is applied.

3.4.5. Method for Preventing Thermal Inversion Illusion Related to Successive Thermal Feedback FIG. 65 is a flowchart illustrating a ninth example of a method for providing thermal feedback according to an embodiment of the present disclosure.

Here, the ninth example of the method for providing the thermal feedback is related to preventing the thermal inversion illusion. Specifically, the ninth example of the method for providing the thermal feedback is related to preventing the thermal inversion illusion when the successive thermal feedback is outputted.

Figure 65:
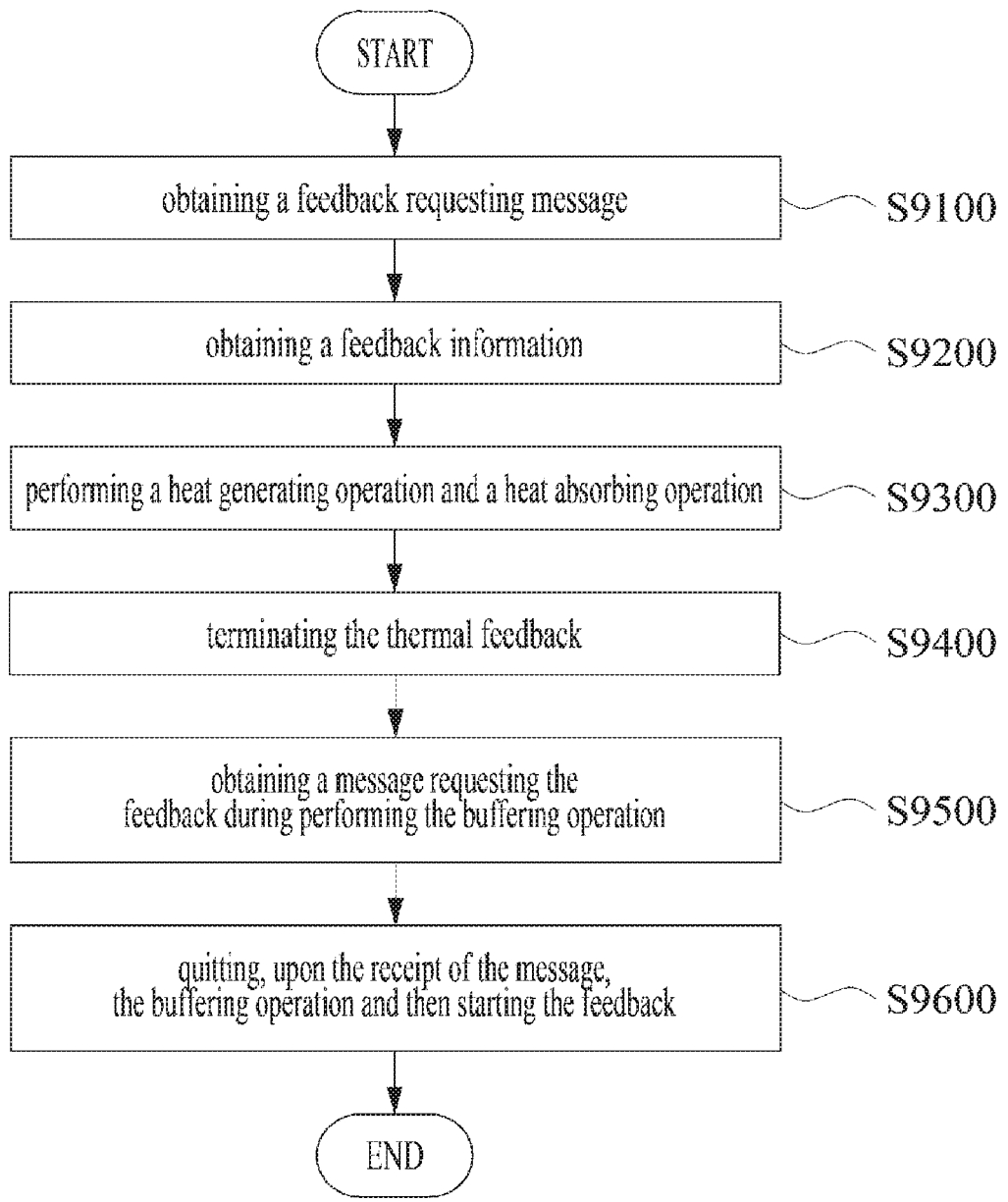
FIG. 65 is a flowchart illustrating a ninth example of a method for providing the thermal feedback according to an embodiment of the present disclosure.

Referring to FIG. 65, the method for providing the thermal feedback may comprise: obtaining a first feedback request message (S9100), acquiring feedback information from the first feedback request message (S9200), performing the heat generating operation or the heat absorbing operation based on the feedback information (S9300), terminating the thermal feedback (S9400), obtaining a second feedback request message during a buffering period (S9500), and stopping the buffering operation upon acquiring the second feedback request message and initiating the feedback operation based on the second feedback request message (S9600).

Hereinafter, each of the above-described steps will be described in more detail.

First, a first feedback request message is acquired (S9100), feedback information is obtained (S9200), the heat generating operation or the heat absorbing operation is performed based on the feedback information (S9300), thermal feedback is terminated, and the buffering operation is performed (S9400). These steps may be similar to steps S6100, S6200, S6300, and S6400 described above.

Here, a second feedback request message may be obtained at the time when the buffering operation is being performed (S9500). The feedback controller 1400 may confirm whether the second feedback request message is acquired similarly to the step S9100 during the buffering operation.

Upon the receipt of the second feedback request message, the buffering operation is stopped and the feedback operation related to the second feedback request message is started (S9600). The feedback controller 1400 may stop the buffering operation immediately upon the receipt of the second feedback request message, and directly start to the thermoelectric operation for outputting the thermal feedback related to the second feedback request message.

3.4.6. Method for Preventing Thermal Inversion Illusion at Termination of Thermal Grill Feedback FIG. 66 is a flowchart illustrating a tenth example of a method for providing the thermal feedback according to an embodiment of the present disclosure.

Here, the tenth example of the method for providing the thermal feedback is related to preventing the thermal inversion illusion. Specifically, the tenth example of the method for providing the thermal feedback is related to preventing the thermal inversion illusion when the thermal grill feedback is terminated.

Figure 66:
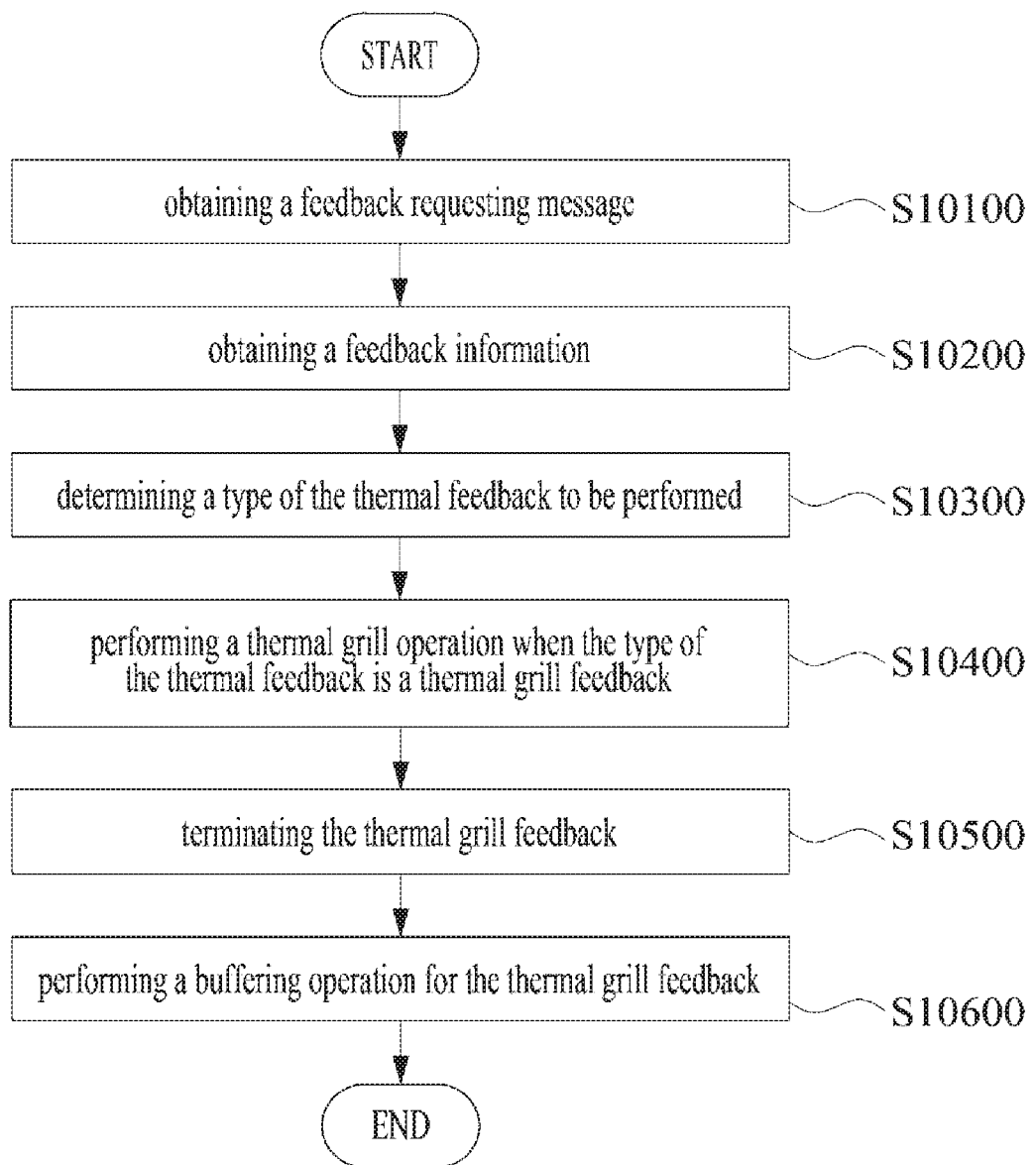
FIG. 66 is a flowchart illustrating a tenth example of a method for providing the thermal feedback according to an embodiment of the present disclosure.

Referring to FIG. 66, the method for providing the thermal feedback may comprise: obtaining a feedback request message (S10100), obtaining feedback information (S10200), determining a type of the thermal feedback to be performed based on the feedback information (S10300), when the determined type of thermal feedback is a thermal grill feedback, performing the thermal grill feedback (S10400), finishing the thermal grill feedback (S10500), and performing the buffering operation for the thermal grill feedback (S10600).

Hereinafter, each of the above-described steps will be described in more detail.

First, a feedback request message is acquired (S10100), feedback information is obtained (S10200), and the type of the thermal feedback to be performed is determined based on the feedback information (S10300). These steps may be similar to steps S2100, S2200, S2300, and S2400 described above.

If the type of the thermal feedback is thermal grill feedback, the thermal grill feedback may be performed (S10400). This step may be similar to performing the thermal grill operation according to the second to fifth examples of the method of providing thermal feedback.

And, the thermal grill feedback may be terminated (S10500). This step may be similar to S6400.

When the thermal grill feedback is terminated, the buffering operation for thermal grill feedback is performed (S10600).

Here, the buffering operation is intended to prevent the thermal inversion illusion. However, the main purpose of the buffering operation related to the termination of the thermal grill feedback is to prevent a hot feeling or a cold feeling temporarily felt by the user after the termination of the operating power for the thermal grill feedback. Here, the hot feeling and cold feeling is caused because the when the heat generating operation and the heat absorbing operation is stopped at the same time, one of the hot region performing the heat generating operation and the cold region performing the heat absorbing operation of the contact surface 1600 may reach the temperature equilibrium at the different time or reach the temperature equilibrium at a temperature different from the initial temperature.

Generally, in the thermal grill feedback, the cold feedback is performed with a greater intensity than the hot feedback, and the temperature change rate after the end of the thermal grill operation is faster at the cold area than the hot area. Accordingly, the feedback controller 1400 may prevent the thermal inversion illusion phenomenon occurring at the hot area or total area by applying the reverse voltage for a predetermined time at the end of the thermal grill feedback. That is, the first operation.

On the other hand, since the intensity of the cold feedback is greater than the intensity of the hot feedback, the time to reach the initial temperature of the cold feedback may be prior to the time to reach the initial temperature of the hot feedback. Accordingly, the feedback controller 1400 may adjust the thermal balance by applying the forward voltage to the heating area or the entire area for a predetermined time after a certain time has passed after the end of the thermal grill feedback. That is, the second operation.

The power, which is applied at the end of the thermal grill feedback and used in the first operation and the second operation, may be referred to as the buffering power, but may also be referred to as a supplemental power. This is because the power has the purpose of making the thermal equilibrium of the contact surface 1600 at the initial temperature at the end of the thermal feedback output.

Here, the supplemental power may be applied to at least one of the heat generating area and the heat absorbing area.

The current direction of the supplemental power may be determined to be a forward direction so that the heat generating portion and heat absorbing portion of the contact surface 1600 is thermally balanced at the initial temperature, since the intensity of the cold feedback for the thermal grill feedback is greater than the intensity of the hot feedback.

Alternatively, the reverse power and the forward power are used together as the supplemental power, but at least one of the current, voltage, application time of the forward power may be adjusted to be larger than those of the reverse power, respectively. Here, when the forward power and the reverse power are applied together with the supplemental power, it is preferable that the reverse power may be applied to the heat absorbing portion and the forward power may be applied to the heat generating portion.

Alternatively, the current direction of the supplemental power may be determined to be a reverse direction to prevent that the contact surface 1600 reaches thermal equilibrium at a temperature greater than the initial temperature by the residual heat due to the thermoelectric operation for the thermal grill feedback.

Alternatively, the reverse power and the forward power are used together as the supplemental power, but at least one of the current, voltage, application time of the forward power may be adjusted to be smaller than those of the reverse power, respectively. Here, when the forward power and the reverse power are applied together with the supplemental power, it is preferable that the forward power is applied to the heat generating portion and the reverse power is applied to the heat absorbing portion.

On the other hand, instead of using the supplemental power as described above, the end timing of the hot feedback and the cold feedback related to the thermal grill feedback may be set to be different from each other.

The heating region first reaches the thermal equilibrium and the heat absorbing region reaches the thermal equilibrium when the heat generating operation and the heat absorbing operation is terminated at the same time, since the cold feedback is performed at a greater intensity than the hot feedback, and thus the coldness may be felt in the process of reaching the thermal equilibrium.

To prevent this, the heat generating operation among the thermoelectric operation for the thermal grill feedback may be first terminated and the heat absorbing operation may be terminated later. Accordingly, the heat generating portion and the heat absorbing portion may reach the thermal equilibrium at the same time.

If the temperature difference amount at the absorbing portion is larger than the temperature change amount at the heat generating portion, the contact surface 1600 may reach the thermal equilibrium at a temperature lower than the initial temperature at the end of the thermal grill feedback output. To prevent this, the heat absorbing operation may be stopped first and stop the heat generating operation later so that the thermal equilibrium is achieved at the initial temperature.

When the thermoelectric element performs thermoelectric operation using electric energy, residual heat may be generated. Such residual heat may cause thermal equilibrium at a temperature higher than the initial temperature at the end of the thermal grill feedback output. To prevent this, the heat absorbing operation may be stopped later and the heat generating operation stopped first so that the thermal equilibrium is achieved at the initial temperature.

In the present embodiment, the first operation, the second operation, and the method of adjusting the stopping point of the end of the heat generating operation/heat absorbing operation may all be performed individually or in combination.

Figure 67:
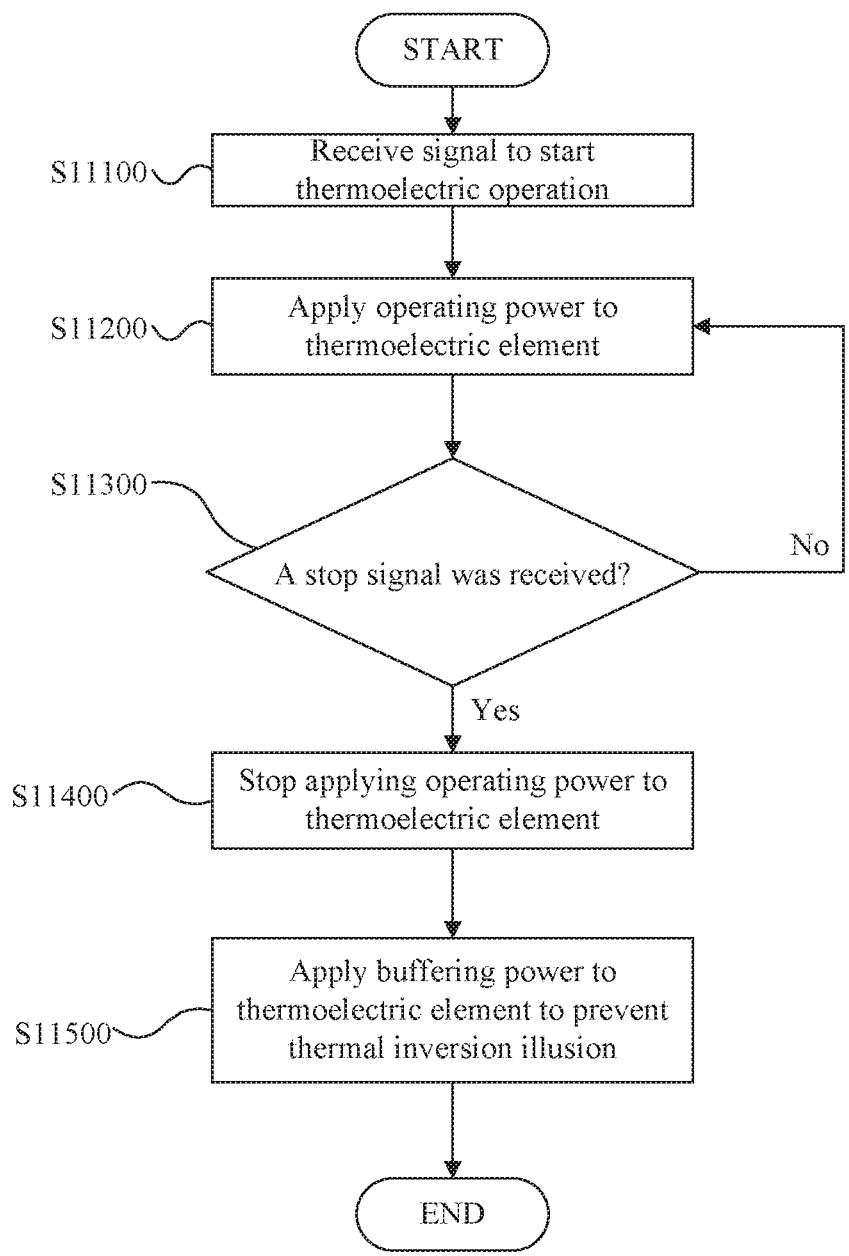
FIG. 67 is a flowchart illustrating an example of a thermoelectric operation according to an embodiment of the present disclosure.

FIG. 67 is a flowchart illustrating an example of a thermoelectric operation according to an embodiment of the present disclosure.

In step S11100, feedback device 100 may receive a signal to start a thermoelectric operation.

In step S11200, feedback device 100 may apply an operating power. For example, feedback device 100 may apply an operating power to the thermoelectric element of the heat outputting module 1200.

In step S11300, feedback device 100 may wait for a stop signal. If in step S11300, feedback device 100 does not receive a stop signal (S11300: No), it may continue to step S11200 and continue applying the operating power. However, if in step S11300, feedback device 100 receives a stop signal (S11300: Yes), it may continue to step S11400.

In step S11400, feedback device 100 may stop applying operating power. For example, feedback device 100 may stop applying an operating power to the thermoelectric element of the heat outputting module 1200.

In step S11500, feedback device 100 may apply a buffering power. In some embodiments, feedback 100 may apply a buffering power to the thermoelectric element of the heat outputting module 1200 instead of shutting off all power. In such embodiments, the buffering power may be selected to prevent a thermal inversion illusion.

The methods of providing thermal feedback according to the embodiments of the present disclosure described above can be used alone or in combination with each other. In addition, since each of the steps described in each thermal feedback providing method is not essential, the method of providing thermal feedback can be performed by including all or part of the steps. Also, since the order in which the steps are described is merely to facilitate explanations, the steps in the method of providing thermal feedback are not necessarily performed in the order described. Non-dependent steps may be performed in any order or in parallel.

Further, in the method of providing thermal feedback according to an embodiment of the present disclosure described above, any steps not described as being executed by a specific controller may be performed by one or both of the application controller 2700 and the feedback controller 1400 of the feedback device 100. In addition, in the above description, the matters described as being performed by the application controller 2700 may be performed by the feedback controller 1400 as needed or, conversely, by the feedback controller 1400. In addition, steps described as being executed by the application controller 2700 may be executed by the feedback controller 1400, or by the collaborative operation of the application controller 2700 and the feedback controller 1400. Again, it should be noted that the application controller 2700 and the feedback controller 1400 may be implemented as a single controller.

The foregoing description is merely illustrative of the technical idea of the present disclosure and various changes and modifications may be made without departing from the essential characteristics of the present disclosure by those skilled in the art. Therefore, the embodiments of the present disclosure described above may be implemented separately or in combination.

Therefore, the embodiments disclosed in the present disclosure are intended to illustrate rather than limit the scope of the present disclosure, and the scope of the technical idea of the present disclosure is not limited by these embodiments. The scope of protection of the present disclosure should be construed according to the following claims, and all technical ideas within the scope of equivalents thereof should be construed as being included in the scope of the present disclosure.

The invention claimed is:

1. A method for providing thermal feedback, performed by a feedback device, wherein the feedback device outputs the thermal feedback, by transmitting a heat generated by a thermoelectric element, to a user via a contact surface contacting with a body part of the user, comprising:
 applying a first power corresponding to first thermal feedback for providing the first thermal feedback;
 receiving a message indicating provision of second thermal feedback different from the first thermal feedback;
 before applying a second power corresponding to the second thermal feedback according to the message, applying a buffering power having a magnitude between the first power and the second power; and
 after applying the buffering power, applying the second power for providing the second thermal feedback.

2. The method of claim 1, wherein the magnitude of the buffering power is determined to reduce or prevent a thermal inversion illusion.

3. The method of claim 1, wherein the applying the buffering power comprises applying the buffering power for a predetermined time duration.

4. The method of claim 3, wherein the predetermined time duration when the first thermal feedback and the second thermal feedback are cold feedback is longer than the predetermined time duration when the first thermal feedback and the second thermal feedback are hot feedback.

5. The method of claim 3, further comprising:
determining whether the first thermal feedback and the second thermal feedback are cold feedback or hot feedback;
when the first thermal feedback and the second thermal feedback are cold feedback, determining the predetermined time duration as a first time duration; and
when the first thermal feedback and the second thermal feedback are hot feedback, determining the predetermined time duration as a second time duration shorter than the first time duration.

6. The method of claim 1, further comprising:
determining whether an intensity difference between the first thermal feedback and the second thermal feedback is equal to or greater than a predetermined level;
when the intensity difference is equal to or greater than the predetermined level, applying the buffering power before applying the second power; and
when the intensity difference is smaller than the predetermined level, after applying the first power, applying the second power without applying the buffering power.

7. The method of claim 1, wherein the first power, the second power and the buffering power have the same polarity.

8. The method of claim 1, wherein the applying the buffering power comprises:
applying a first buffering power having a magnitude between the first power and the second power; and
applying a second buffering power having a magnitude between the first buffering power and the second power.

9. The method of claim 1, wherein the magnitude of the first power is greater than the magnitude of the second power.

10. A method for providing thermal feedback, performed by a feedback device, wherein the feedback device outputs the thermal feedback, by transmitting a heat generated by a thermoelectric element, to a user via a contact surface contacting with a body part of the user, comprising:
applying a first power corresponding to first thermal feedback for providing the first thermal feedback;
receiving a message indicating provision of second thermal feedback different from the first thermal feedback;
before applying a second power corresponding to the second thermal feedback according to the message, applying a buffering power having a duty ratio between the first power and the second power; and
after applying the buffering power, applying the second power for providing the second thermal feedback.

11. The method of claim 10, wherein the duty ratio of the buffering power is determined to reduce or prevent a thermal inversion illusion.

12. The method of claim 10, wherein the applying the buffering power comprises applying the buffering power for a predetermined time duration.

13. The method of claim 12, wherein the predetermined time duration when the first thermal feedback and the second thermal feedback are cold feedback is longer than the predetermined time duration when the first thermal feedback and the second thermal feedback are hot feedback.

14. The method of claim 12, further comprising:
determining whether the first thermal feedback and the second thermal feedback are cold feedback or hot feedback;
when the first thermal feedback and the second thermal feedback are cold feedback, determining the predetermined time duration as a first time duration; and
when the first thermal feedback and the second thermal feedback are hot feedback, determining the predetermined time duration as a second time duration shorter than the first time duration.

15. The method of claim 10, further comprising:
determining whether an intensity difference between the first thermal feedback and the second thermal feedback is equal to or greater than a predetermined level;
when the intensity difference is equal to or greater than the predetermined level, applying the buffering power before applying the second power; and
when the intensity difference is smaller than the predetermined level, after applying the first power, applying the second power without applying the buffering power.

16. The method of claim 10, wherein the first power, the second power and the buffering power have the same polarity.

17. The method of claim 10, wherein the applying the buffering power comprises:
applying a first buffering power having a duty ratio between the first power and the second power; and
applying a second buffering power having a duty ratio between the first buffering power and the second power.

18. The method of claim 10, wherein the duty ratio of the first power is greater than the duty ratio of the second power.

* * * * *